US009175002B2

(12) United States Patent
Cushman et al.

(10) Patent No.: US 9,175,002 B2
(45) Date of Patent: Nov. 3, 2015

(54) SYNTHESIS AND USE OF DUAL TYROSYL-DNA PHOSPHODIESTERASE I (TDP1)—TOPOISOMERASE I (TOP1) INHIBITORS

(71) Applicant: Purdue Research Foundation, West Lafayette, IN (US)

(72) Inventors: Mark S. Cushman, West Lafayette, IN (US); Trung X. Nguyen, West Lafayette, IN (US); Martin M. Conda-Sheridan, Evanston, IL (US); Yves George Pommier, Bethesda, MD (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 14/537,630

(22) Filed: Nov. 10, 2014

(65) Prior Publication Data

US 2015/0133445 A1 May 14, 2015

Related U.S. Application Data

(62) Division of application No. 13/834,652, filed on Mar. 15, 2013, now Pat. No. 8,912,213.

(60) Provisional application No. 61/624,239, filed on Apr. 13, 2012.

(51) Int. Cl.
| | | |
|---|---|---|
| C07D 221/22 | (2006.01) | |
| A61K 31/44 | (2006.01) | |
| C07D 491/056 | (2006.01) | |
| C07D 221/18 | (2006.01) | |
| C07D 401/06 | (2006.01) | |

(52) U.S. Cl.
CPC .......... *C07D 491/056* (2013.01); *C07D 221/18* (2013.01); *C07D 401/06* (2013.01)

(58) Field of Classification Search
None
See application file for complete search history.

(56) References Cited

U.S. PATENT DOCUMENTS

| | | | |
|---|---|---|---|
| 5,597,831 A | 1/1997 | Michalsky et al. |
| 6,509,344 B1 | 1/2003 | Cushman et al. |
| 7,312,228 B2 | 12/2007 | Cushman et al. |
| 7,495,100 B2 | 2/2009 | Cushman et al. |
| 7,781,445 B2 | 8/2010 | Cushman et al. |
| 8,053,443 B2 | 11/2011 | Cushman et al. |
| 2004/0229895 A1 | 11/2004 | Jagtap et al. |
| 2008/0262016 A1 | 10/2008 | Jagtap et al. |
| 2012/0302563 A1 | 11/2012 | Cushman et al. |
| 2013/0143878 A1 | 6/2013 | Cushman |
| 2014/0018360 A1 | 1/2014 | Cushman |

FOREIGN PATENT DOCUMENTS

| | | |
|---|---|---|
| WO | WO 2004/014862 | 2/2004 |
| WO | WO 2012/024437 | 2/2012 |

OTHER PUBLICATIONS

Morrell, A. J Med Chem 2006 vol. 49 pp. 7740-7753.*
Staker, B.L.; Hjerrild, K.; Feese, M.D.; Behnke, C.A.; Burgin Jr., A.B.; Stewart, L. "The Mechanism of Topoisomerase I Poisoning by a Camptothecin Analog," Proc. Natl. Acad. Sci. U.S.A., 15387- ,99 , 2002.15392.
Pommier, Y.; Pourquier, P.; Fan, Y.; Strumberg, D. "Mechanism of Action of Eukaryotic DNA Topoisomerase I and Drugs Targeted to the Enzyme," Biochim. Biophys. Acta, .83-106 ,1400 ,1998.
Kohlhagen, G.; Paull, K.; Cushman, M.; Nagafuji, P.; Pommier, Y., "Protein-Linked DNA Strand Breaks Induced by NSC 314622, a Novel Noncamptothecin Topoisomerase I Poison," Mol. Pharmacol., 1998, 54, 50-58.
Jaxel, C.; Kohn, K. W.; Wani, M. C.; Wa.., M.C.; Pommier, Y., "Structure-Activity Study of the Actions of Camptothecin Derivatives on Mammalian Topoisomerase I: Evidence for a Specific Receptor Site and a Relation to Antitumor Activity," Cancer. Rev., .1465-1469 ,49 ,1989.
Minami, H.; Beijnen, J.H.; Verweij, J.; Ratain, M.J., "Limited Sampling Model for the Area under the Concentration Time Curve of Total Topotecan," Clin. Cancer Res., .43-46 ,2 ,1996.
Danks, M.K.; Pawlik, C.A.; Whipple, D.O.; Wolverton, J.S., "Intermittant Exposure of Medulloblastoma Cells to Topotecan Produces Growth Inhibition equivalent to Continuous Exposure," Clinical Cancer Research, .1731-1738 ,3 ,1997.
Haas, N.B.; LaCreta, F.P.; Walczak, J.; Hudes, G.R.; Brennan, J.M.; Ozols, R.F.; O'Dwyer, P.J. "Phase 1/Pharmacokinetic Study of Topotecan by 24-Hour Continuous Infusion Weekly," Cancer Res., 54 ,1994 .1226-1220.
Shapiro, S.L.; Geiger, K.; Youlus, J.; Freedman, L., "Indandiones. II. A Modified Dieckmann Reaction," J. Org. Chem., .3580-3582 ,26 , 1961.
Pailer, M.; Worther, H.; Meller, A., "Some reactions of 2-aryl-1,3-indandiones," Monatsh Chem. ,1961 .1037-1047 ,92.
Freireich, E.J., et al., "Quantitative Comparison to Toxicity of Anticancer Agents in Mouse, Rat, Hamster, Dog, Monkey, and Man," Cancer Chemother. Rep., .219-244 ,(4) 50 ,1966.
Nagarajan, M.; Xiao, X.; Antony, S.; Kohlhagen, G.; Pommier, Y.; Cushman, M., "Design, Synthesis, and Biological Evaluation of Indenoisoquinoline Topoisomerase I Inhibitors Featuring Polyamine Side Chains on the Lactam Nitrogen," J. Med. Chem,. .5712-5724 , 46 ,2003.
Hollingshead, M.; Plowman, J.; Alley, M.; Mayo, J.; Sausville, E "The Hollow Fiber Assay," Contrib. Oncol,. .109-120 ,54 ,1999.
Plowman, J.; Camalier, R.; Alley, ML; Sausville, E.; Schepartz, S., "US NCI Testing Procedures," Contrib. Onco.l. .121-135 ,54 ,1999.

(Continued)

*Primary Examiner* — Heidi Reese
(74) *Attorney, Agent, or Firm* — Mark S. Cohen; Pearl Cohen; Zedek Latzer Baratz LLP

(57) ABSTRACT

The invention described herein pertains to the synthesis and use of certain N-substituted indenoisoquinoline compounds which inhibit the activity Tyrosyl-DNA Phosphodiesterase I (Tdp1) or Topoisomerase I (Top1) or both, or otherwise demonstrate anticancer activity. Also disclosed are novel N-substituted indenoisoquinoline compounds and pharmaceutical compositions comprising the novel N-substituted indenoisoquinoline compounds.

6 Claims, 19 Drawing Sheets

(56) References Cited

OTHER PUBLICATIONS

Antony et al., "Differential Induction of Topoisomerase I-DNA Cleavage Complexes by the Indenoisoquinoline MJ-III-65 (NSC 706744) and Camptothecin: Base Sequence Analysis and Activity against Camptothecin-Resistant Topoisomerase I," Cancer Res., 2003, 63, 7428-7435.

West, Anthony R., "Solid State Chemistry and its Applications," Wiley, New York, 1988, pp. & 358 .365.

Kucerova, T et al., "Solovolysis of 0-acyl-10-hydroxy-10-dihydro-indeno[1,2-c]Isoquinolin- -5,11 diones,",1979Database CA, Chemical Abstracts Service, Database Accession No. 1980:22814.

Cushman, Mark, et al., "Synthesis of a New Indeno[1,2-c]Isoquinolines: Cytotoxic Non-Camptothecin Topoisomerase I Inhibitors,", 2000Journal of Medicinal Chemistry, vol. 43No. 20 pp. 3688-3698.

Jayaraman, Muthusamy, et al., "Synthesis of New Dihydroindeno[1-2-c]Isoquinolone and Indenoisoquinolinium Chloride Topoisomerase I Inhibitors Having High In Vivo Anticancer Activity in the Hollow Fiber Animal Model,",2002 Journal of Medicinal Chemistry, vol. 45, No. 1, pp. 242-249.

Morrell, Andrew, et al., "Synthesis, of Nitrated Indenoisoquinolines As Topoisomerase I Inhibitors," ,2004Bioorganic &Medicinal Chemistry Letters, vol. 14 , pp. 3659-3663.

Nagarajan, Muthukaman, et al., "Synthesis and Anticancer Activity of Simplified Indenoisoquinoline Topoisomerase I Inhibitors Lacking Substituents on the Aromatic Ring," 2004, Journal of Medicinal Chemistry, vol. 47 No. 23 pp. 5651-5661.

Strumberg, Dirk, et al., "Synthesis of Cytotoxic Indenoisoquinoline Topoisomerase I Poisons,", 1999 Journal of Medicinal Chemistry, vol. 42No. 3, pp. 446-457.

Wawzonek, Stanley, "Novel Formation of 11-Ketoindeno[1,2-c]Isocoumarin,",1968The Journal of Organic Chemistry, vol. 33 No. 2 pp. 896-897.

Wawzonek, Stanley, "Synthesis of 6-Substituted-6H-Indeno[1,2-c] Isoquinoline-5,11-diones,",1982 Database CA, Chemical Abstracts Service, Database Accession No. 1982:199485.

Cushman, Mark, and Prem Mohan. "Synthesis and antitumor activity of structural analogs of the anticancer benzophenanthridine alkaloid fagaronine chloride." Journal of medicinal chemistry :(1985) 28.8 .1031-1036.

Wawzonek, S., J. K. Stowell, and R. E. Karll. "The Synthesis and Reactions of 1-Carbamyl-1 1-ketoindeno ,1]2-c] isoquinoline1." The Journal of Organic Chemistry .1004-1006 :(1966) 31.4.

Cushman, Mark, Prem Mohan, and Edward CR Smith. "Synthesis and biological activity of structural analogs of the anticancer benzophenanthridine alkaloid nitidine chloride." Journal of medicinal chemistry .544-547 :(1984) 27.4.

Staker et al., "Structures of Three Classes of Anticancer Agents Bound to the Human Topoisomerase I-DNA Covalent Complex," J. Med. Chem., 2005vol. 48No. 2336-2345 ,7.

Ioanoviciu et al., "Synthesis and Mechanism of Action Studies of a Series of Norindenoisoquinoline Topoisomerase I Poisons Reveal an Inhibitor with a Flipped Orientation in the Ternary DNA-Enzyme-Inhibitor Complex As Determined by X-ray Crystallographic Analysis," J. Med. Chem., 2005, vol. 48, No. 15, 4803-4814.

Xiao et al., "On the Binding of Indeno[1,2-c]isoquinolines in the DNA-Topoisomerase I Cleavage Complex," J. Med. Chem. 2005vol. 48No. 3231-3238 ,9.

Antony et al., "Cellular Topoisomerase I Inhibition and Antiproliferative Activity by MJ-III-65 (NSC ,(706744an Indenoisoquinoline Topoisomerase I Poison," Molecular Pharmacology, 2005vol. 67No. 2 523-530.

Peterson, !Catherine E., et al. "Alcohol-, Diol-, and Carbohydrate-Substituted Indenoisoquinolines as Topoisomerase I Inhibitors: Investigating the Relationships Involving Stereochemistry, Hydrogen Bonding, and Biological Activity." Journal of medicinal chemistry .4937-4953 :(2011) 54.14.

Kiselev, Evgeny, et al. "7-azaindenoisoquinolines as topoisomerase I inhibitors and potential anticancer agents." Journal of medicinal chemistry .6106-6116 :(2011) 54.17.

Kiselev, Evgeny, et al. "Azaindenoisoquinolines as Topoisomerase I Inhibitors and Potential Anticancer Agents: A Systematic Study of Structure-Activity Relationships." Journal of medicinal chemistry 55.4.1682-1697 :(2012).

Nguyen, Trung Xuan, et al. "Synthesis and Biological Evaluation of the First Dual Tyrosyl-DNA Phosphodiesterase I (Tdp1)-Topoisomerase I (Topi) Inhibitors." Journal of Medicinal Chemistry 55.9 .4457-4478 :(2012).

Conda-Sheridan, Martin, et al. "Synthesis and Biological Evaluation of Indenoisoquinolines That Inhibit Both Tyrosyl-DNA Phosphodiesterase I (Tdp1) and Topoisomerase I (Topi)." Journal of medicinal chemistry .180-200 :(2013).

Morreil, A. et al., Bioorg. Med. Chem Lett. ,2006vol. 16, pp. 4395-4399.

Nagarajan, M. et al., J. Med. Chem. ,2006vol. 49, pp. 5129-5140.

* cited by examiner

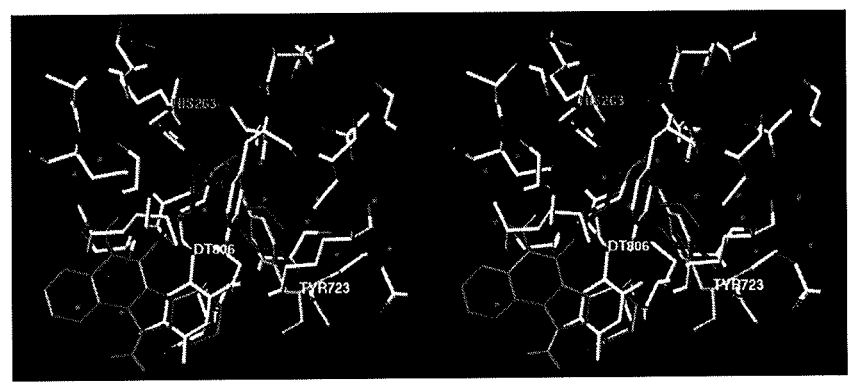
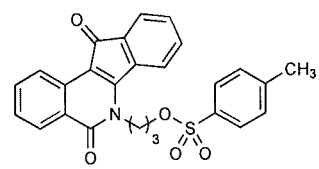
Compound 25
FIG 3

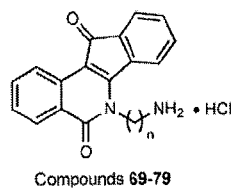

Compounds 69-79

Compound 18-23
(n = 2-7)

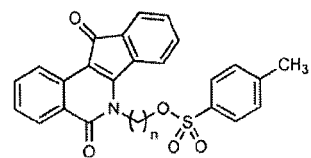

Compound 25-29
(n = 3-7)

All were inactive against Tdp1 (IC$_{50}$ > 111 μM).

| Comp. | n | IC$_{50}$ (μM) Tdp1 | | Top1 |
|---|---|---|---|---|
| | | rec. | WCE | |
| 69 | 2 | 55.3±11.4 | 78 | +++ |
| 70 | 3 | 29.5 | 29.5 | +++ |
| 71 | 4 | 22.3 | 23.4 | +++ |
| 72 | 5 | 17.5±4.5 | 28 | 0 |
| 73 | 6 | 25±5.5 | 35 | ++ |
| 74 | 7 | 28.8±6.8 | 31 | 0 |
| 75 | 8 | 48 | 49 | + |
| 76 | 9 | 47 | 48 | 0 |
| 77 | 10 | 14.1 | 21.3 | 0 |
| 78 | 11 | 12.8 | 14.1 | + |
| 79 | 12 | 15.1 | 33 | 0/+ |

Rec. = Recombinant Tdp1
WCE = Whole Cell Extract Tdp1

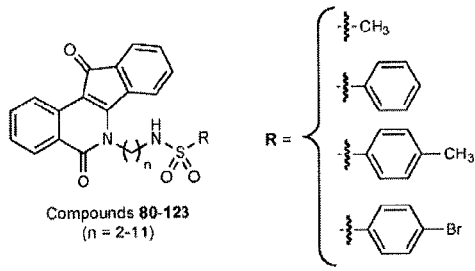

Compounds 80-123
(n = 2-11)

All were inactive against Tdp1 (IC$_{50}$ > 111 μM) and inactive against Top1 (0 or 0/+).

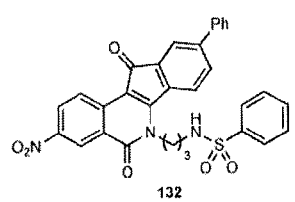

132

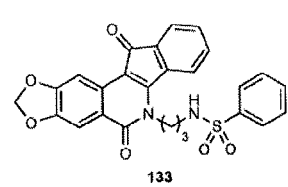

133

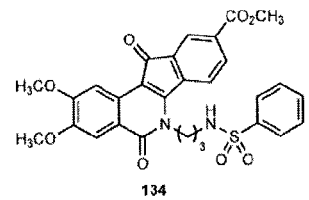

134

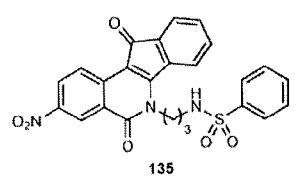

135

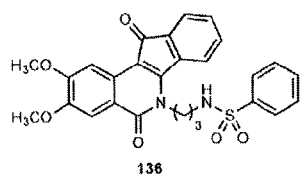

136

All were inactive against Tdp1
(IC$_{50}$ > 111 μM).

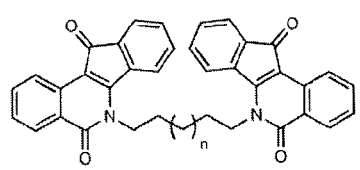

Compounds 140-142
(n = 6-8)

All were inactive against Tdp1
(IC$_{50}$ > 111 μM).

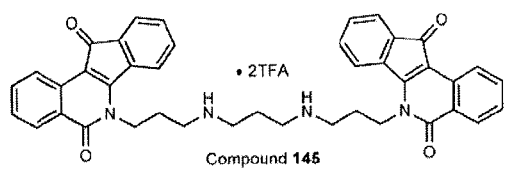

Compound 145

| IC$_{50}$ (μM) Tdp1 | | Top1 |
|---|---|---|
| rec. | WCE | |
| 1.52±0.05 (n=6) | 1.9 | ++++ |

FIG 11

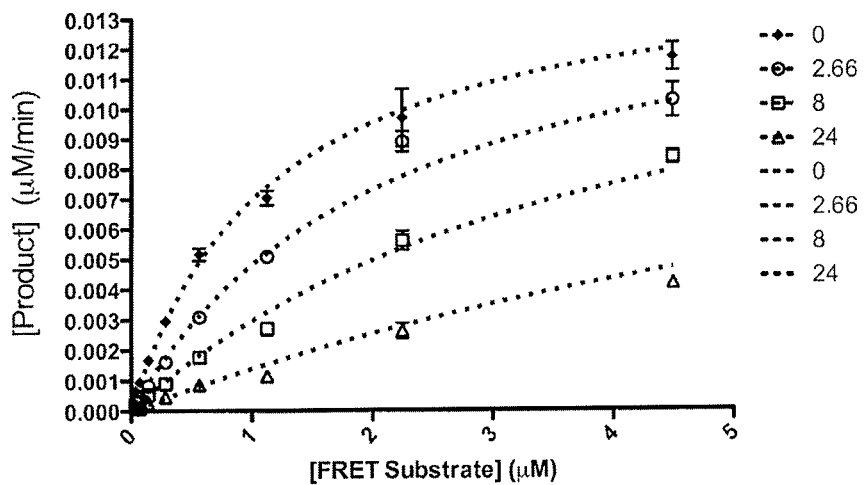
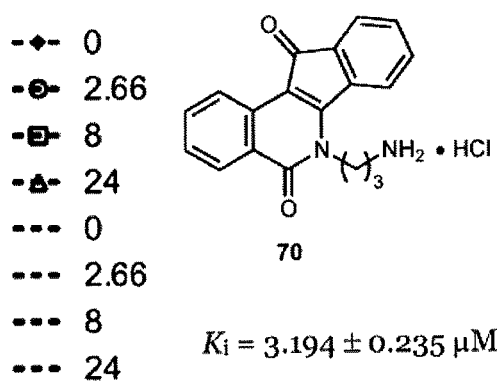
$K_i = 3.194 \pm 0.235\ \mu M$
$K_m = 1.165 \pm 0.088\ \mu M$
FIG 13

A
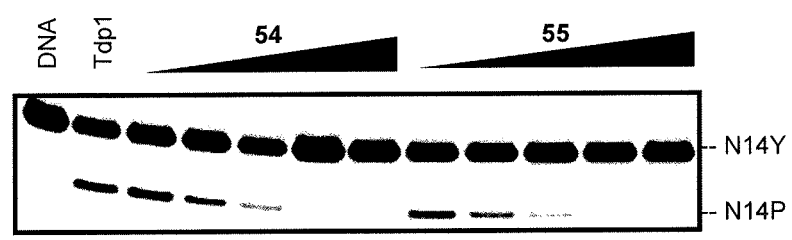
B
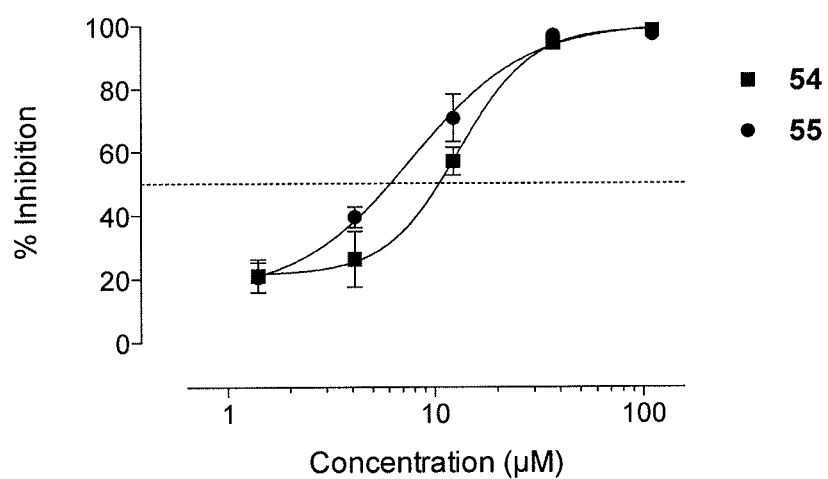
FIG 18

US 9,175,002 B2

SYNTHESIS AND USE OF DUAL TYROSYL-DNA PHOSPHODIESTERASE I (TDP1)—TOPOISOMERASE I (TOP1) INHIBITORS

CROSS-REFERENCE TO RELATED APPLICATIONS

This application is a divisional application of U.S. patent application Ser. No. 13/834,652, filed on Mar. 15, 2013, which claims the benefit of U.S. Provisional Application No. 61/624,239, filed on Apr. 13, 2012, both of which are incorporated by reference in their entirety.

GOVERNMENT RIGHTS

This invention was made with government support under grant number CA089566 awarded by the National Institutes of Health (NIH). The government has certain rights in the invention.

TECHNICAL FIELD

The invention described herein pertains to the synthesis and use of certain N-substituted indenoisoquinoline compounds which inhibit the activity Tyrosyl-DNA Phosphodiesterase I (Tdp1) or Topoisomerase I (Top1) or both, or otherwise demonstrate anticancer activity.

BACKGROUND AND SUMMARY OF THE INVENTION

As is elaborated below, Topoisomerase I (Top1) and Phosphodiesterase I (Tdp1) are involved in DNA replication, transcription and repair; and it appears that inhibition of either enzyme, or both of them, is useful in treatment of disease, particularly in cancer. Certain N-substituted indenoisoquinoline compounds have been reported which inhibit the activity of Top1 and have potential in cancer chemotherapy. See for example US-2008-0318995-A1.

It has been discovered that N-substituted indenoisoquinoline compounds are useful as inhibitors of Tdp1 and that some of them inhibit both Tdp1 and Top1. Further, novel N-substituted indenoisoquinoline compounds which inhibit Top1 and/or show anticancer activity have been discovered.

BRIEF DESCRIPTION OF THE DRAWINGS

FIG. 3 shows overlapped hypothetical structures of the binary complex Tdp1-indenoisoquinoline sulfonate 25 and the crystal structure of the quaternary complex consisting of Tdp1-5'-D(*AP*GP*TP*T)-vanadate-3'-Top1-derived peptide residues 720-727 (mutation L724Y). Red: indenoisoquinoline sulfonate; green, Tyr723; yellow, DT806; vanadate, fuchsia. The figure is programmed for wall-eyed (relaxed) viewing.

[b]Compound-induced DNA cleavage due to Top1 inhibition is graded by the following semiquantitative relative to 1 µM camptothecin (1): 0, no inhibitory activity; +, between 20 and 50%, activity; ++, between 50 and 75% activity; +++, between 75% and 95% activity; ++++, equipotent. The 0/+ ranking is between 0 and +.

Figure 8:
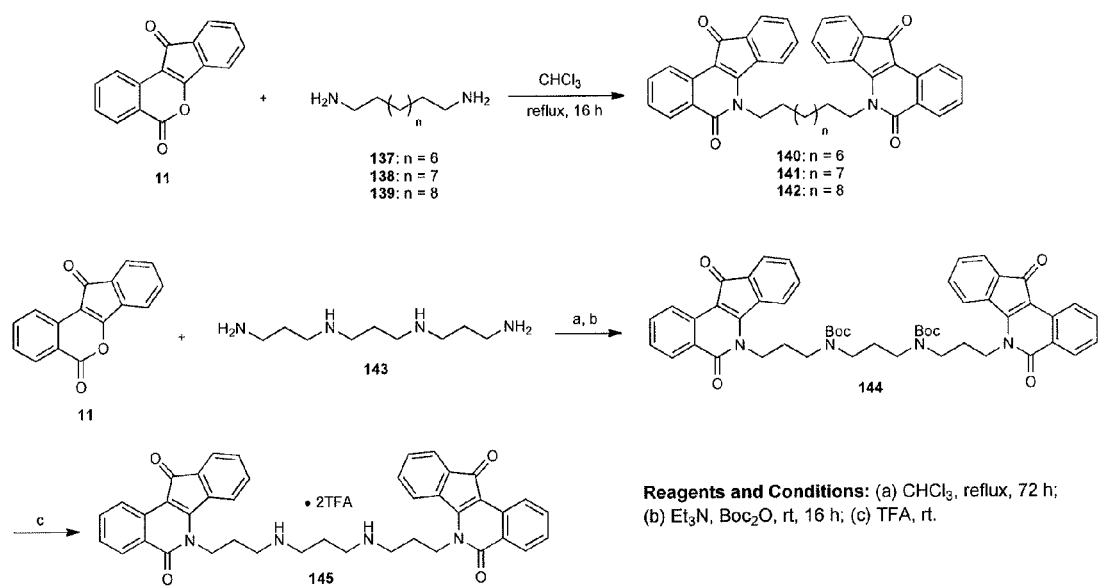

FIG. 8 shows Scheme 9. Preparation of Bisindenoisoquinolines.

Figure 9:
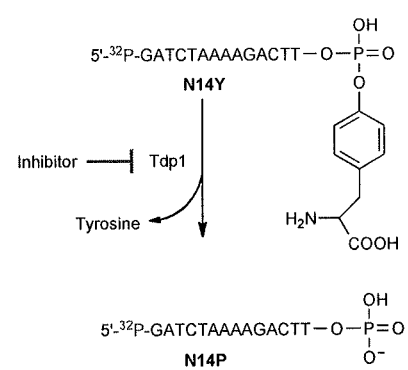

FIG. 9 shows schematic representation of the Tdp1 gel-based assays using recombinant Tdp1. The Figure discloses SEQ ID NOS 2 and 3, respectively, in order of appearance.

Figure 10:
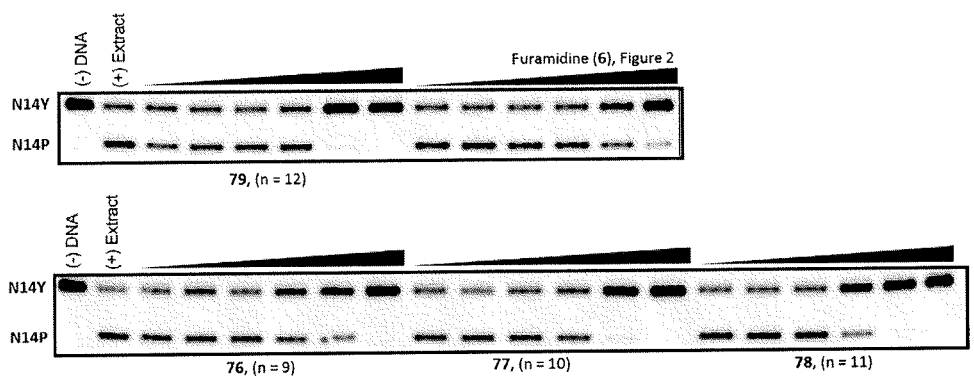

FIG. 10 shows representative gels showing concentration-dependent inhibition of endogenous Tdp1 in whole cell extract by indenoisoquinoline amine hydrochloride inhibitors. Concentrations were 0.5, 1.4, 4.1, 12.3, 37, 111 µM.

FIG. 11 shows inhibitory activities of target compounds against Tdp1 and Top1.

Figure 12:
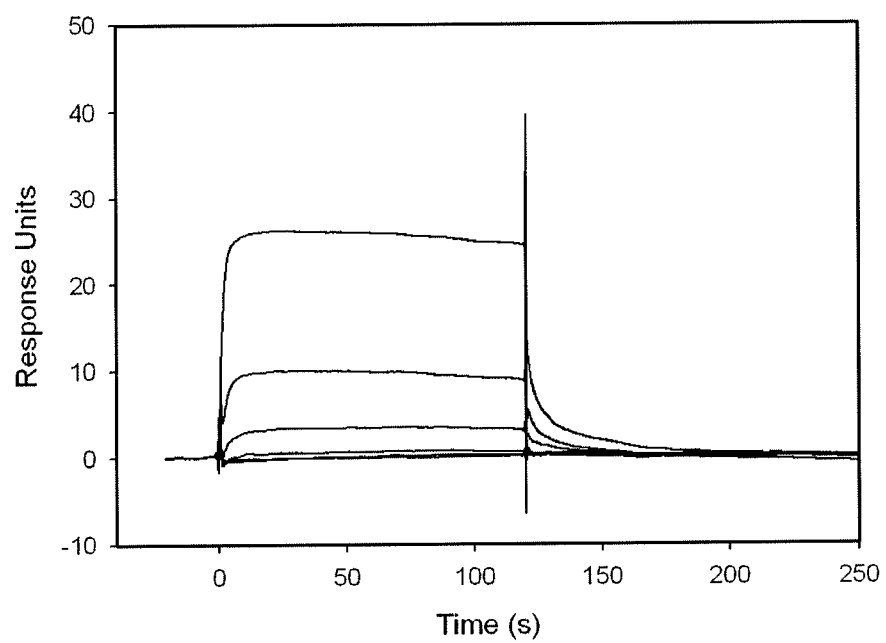

FIG. 12 shows direct binding of 70 to Tdp1 by surface plasmon resonance spectroscopy. Variable concentrations of 70 (33, 11, 3.7, 1.2 and 0.4 µM) were injected over amine coupled Tdp1 protein. The compound rapidly reaches equilibrium and then completely dissociates.

FIG. 13 shows competitive inhibition of 70 against recombinant Tdp1 measured by FRET assay.

Figure 14:
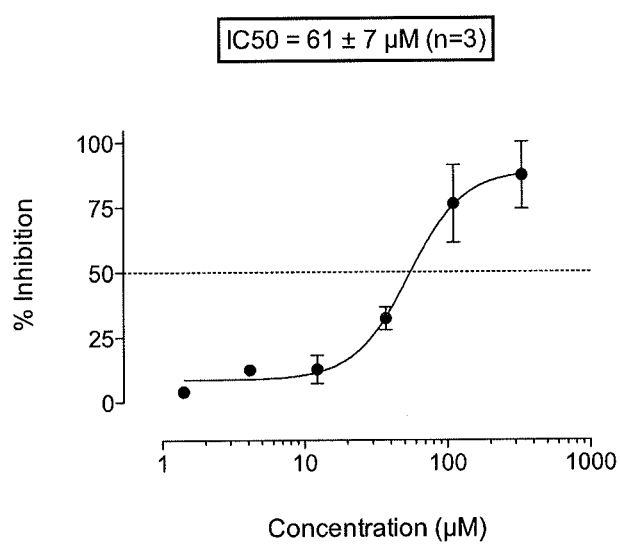

FIG. 14 shows a titration curve of compound 14 of (B) against Tdp1.

Figure 15:
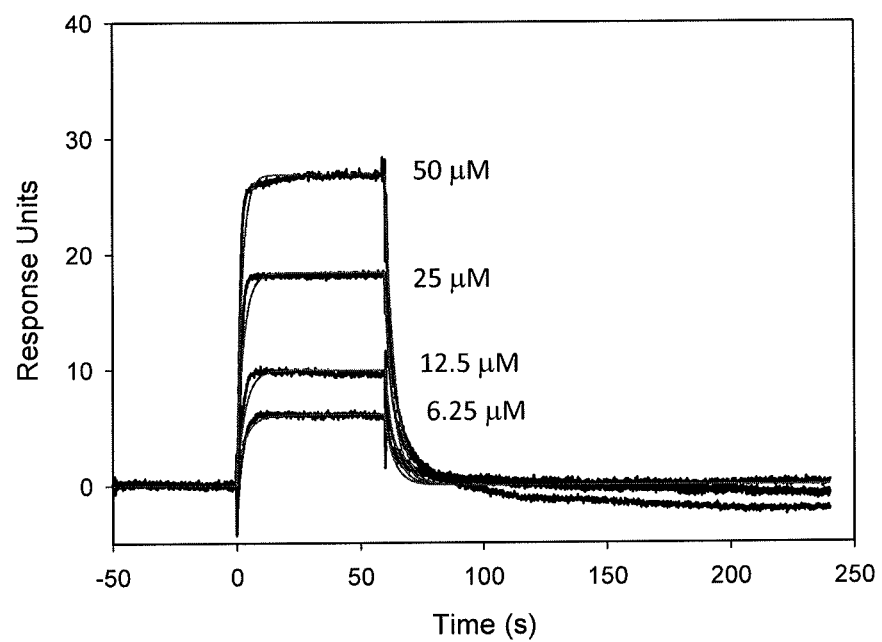

FIG. 15 shows surface plasmon resonance for compound 14 of (B) with Tdp1. The binding of compound 14 to Tdp1 was examined using SPR spectroscopy. Different concentrations of 14 (50, 25, 12.5 and 6.25 µM) were injected over immobilized Tdp1. The kinetics were fit to a 1:1 binding model yielding the following parameters, $k_a$ 7.7 $e_4$ 1/Ms, $k_d$ 0.24 1/s and $K_D$ 31 µM.

Figure 16:
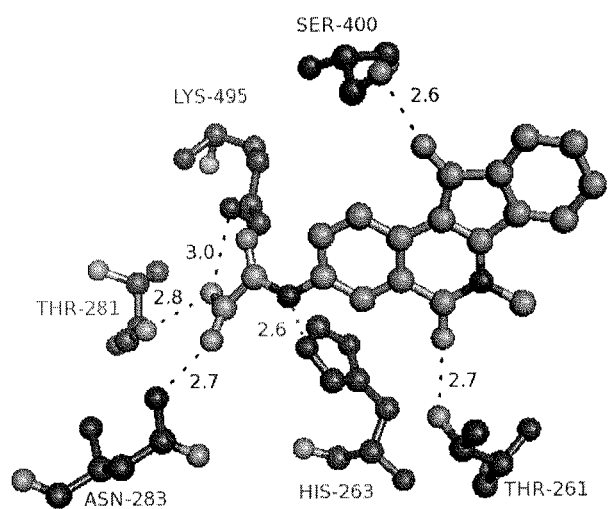

FIG. 16 shows a hypothetical binding model of 14 of (B) in of the binding pocket of Tdp1.

Figure 17:
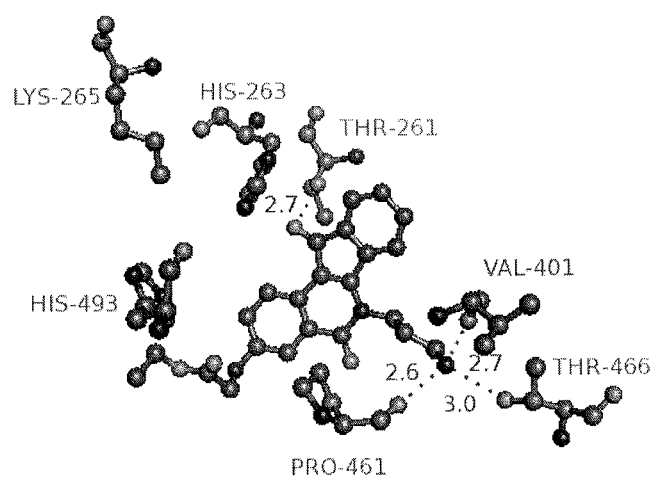

FIG. 17 shows a hypothetical binding model of 40 of (B) in of the binding pocket of Tdp1.

FIG. 18 shows: A. Representative gel showing Tdp1 inhibition for compounds 54 and 55 of (B). B. Titration curves for determination of Tdp1 $IC_{50}$ values for compounds 54 and 55 of (B).

Figure 19:
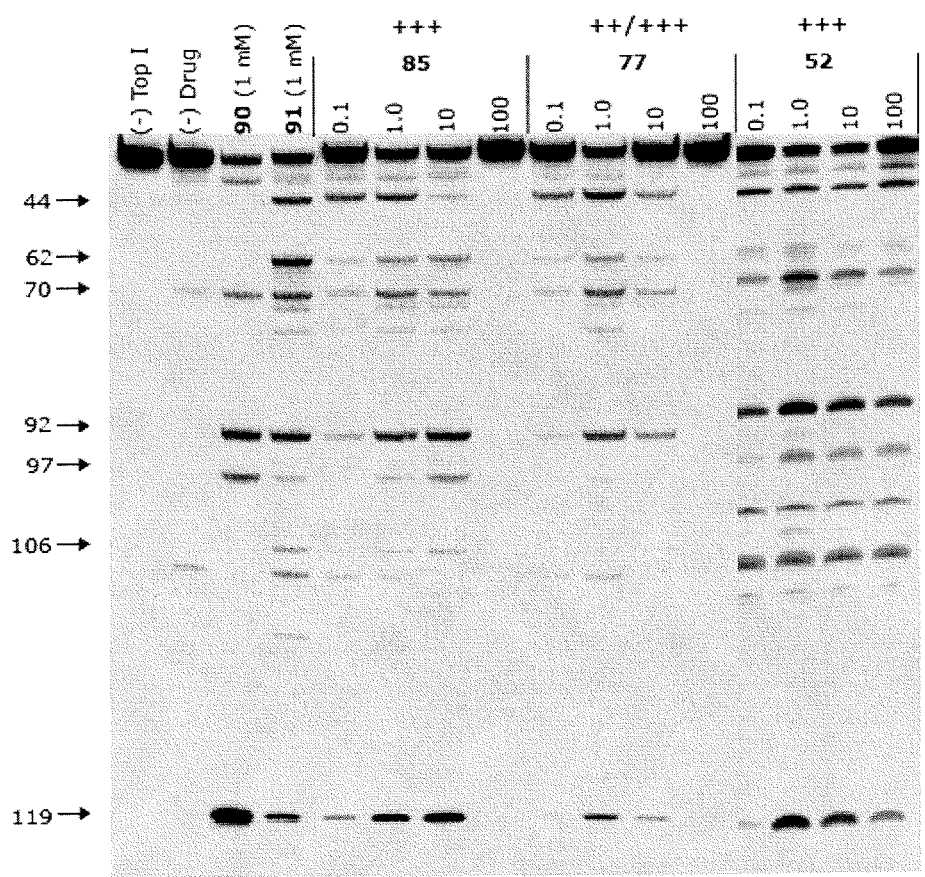

FIG. 19 shows Top1-mediated DNA cleavage induced by 85, 77 and 52 of (B). Lane 1: DNA alone; lane 2: Top1 alone; lane 3: 1, 1 µM; lane 4: 5, 1 µM; lane 5-16: 85, 77 and 52 at 0.1, 1, 10 and 100 µM respectively from left to right. Numbers and arrows on the left indicate arbitrary cleavage site positions. The activity of the compounds to produce Top1-mediated DNA cleavage was expressed semiquantitatively as follows: +, weak activity; ++ and +++, moderate activity; ++++, similar activity as 1 µM camptothecin (90).

DETAILED DESCRIPTION

In one embodiment, there is provided a method for treating a disease or condition responsive to tyrosyl-DNA phosphodiesterase I (Tdp1) inhibition in a host animal, the method comprising the step of administering to the host animal an effective amount of a compound of the formula

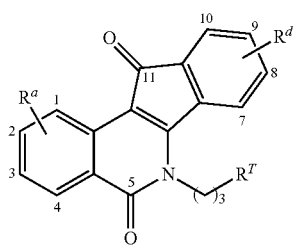

or a pharmaceutically acceptable salt thereof, wherein the compound reduces the activity of Tdp1, when said compound is in contact with Tdp1; and wherein:

n is 1, 2, 3, 4, 5, 6, 7, 8, 9, 11, or 12, $R^T$ is amino, methylamino, or dimethylamino, or —(CH$_2$)$_n$—$R^T$ represents

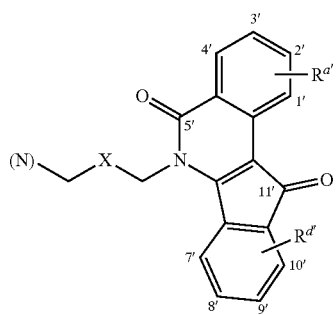

in which:

(N) represents the ring nitrogen;

X is a group having the general structure —(CH$_2$)$_m$-[(CH$_2$)$_x$—NR$^M$—(CH$_2$)$_y$]$_z$—(NR$^N$)$_p$—(CH$_2$)$_q$—, where m is 0 or 1, x and y are integers independently ranging from 1 to about 4, z is an integer ranging from 1 to about 4, p is 0 or 1, q is 0 or an integer ranging from 1 to about 2, and where $R^M$ and $R^N$ are independently selected in each instance from hydrogen and methyl;

$R^a$ and $R^{a'}$ each independently represent 1-4 substituents each of which is independently selected from the group consisting of hydrogen, halo, hydroxy, optionally substituted (1-4C)alkyl, optionally substituted (1-4C)alkoxy, cyano, nitro, amino, carboxymethylamino, optionally substituted alkylthio, optionally substituted alkylsulfonyl, carboxylic acid and derivatives thereof, and sulfonic acid and derivatives thereof; or $R^a$ and $R^{a'}$ each represent 2-4 substituents where 2 of said substituents are adjacent substituents and are taken together with the attached carbons to form an optionally substituted heterocycle, and where any remaining substituents are each independently selected from the group consisting of hydrogen, halo, hydroxy, optionally substituted (1-4C) alkyl, optionally substituted (1-4C)alkoxy, cyano, nitro, optionally substituted (1-4C)alkylthio, optionally substituted (1-4C)alkylsulfonyl, carboxylic acid and derivatives thereof, and sulfonic acid and derivatives thereof; and $R^d$ and $R^{d'}$ each independently represent 1-4 substituents each of which is independently selected from the group consisting of hydrogen, halo, hydroxy, optionally substituted (1-4C)alkyl, optionally substituted (1-4C)alkoxy, cyano, nitro, optionally substituted (1-4C)alkylthio, optionally substituted (1-4C)alkylsulfonyl, phenyl (which may bear one or more amino, hydroxyl, halo, thiol, (1-6C)alkyl or halo(1-6C) alkyl substituents), carboxylic acid and derivatives thereof, and sulfonic acid and derivatives thereof; or $R^d$ and $R^{d'}$ each independently represent 2-4 substituents where 2 of said substituents are adjacent substituents and are taken together with the attached carbons to form an optionally substituted heterocycle, and where any remaining substituents are each independently selected from the group consisting of hydrogen, halo, hydroxy, optionally substituted (1-4C)alkyl, optionally substituted (1-4C)alkoxy, cyano, nitro, optionally substituted (1-4C)alkylthio, optionally substituted (1-4C)alkylsulfonyl, carboxylic acid and derivatives thereof, and sulfonic acid and derivatives thereof.

One embodiment of the above method is one wherein $R^a$, $R^{a'}$, $R^d$, and $R^{d'}$ are independently selected and each includes one or more alkoxy groups or an alkylenedioxy group. One embodiment of the above method is one wherein each of $R^a$, $R^{a'}$, $R^d$, and $R^{d'}$ is hydrogen.

One embodiment of the above method for any of the above is one wherein X is CH$_2$NH(CH$_2$)$_3$NHCH$_2$, CH$_2$CH$_2$NH (CH$_2$)$_3$NHCH$_2$CH$_2$, CH$_2$CH$_2$NH(CH$_2$)$_4$NHCH$_2$CH$_2$, or CH$_2$NH(CH$_2$)$_2$NH(CH$_2$)$_2$NHCH$_2$.

One embodiment of the above method is one wherein the compound is of Formula A:

Formula A

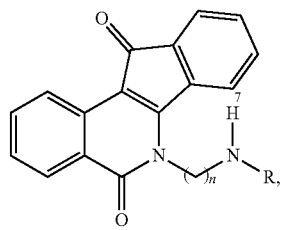

or a pharmaceutically acceptable salt thereof, wherein

R is H or (CH$_2$)$_s$—NH—(CH$_2$)$_t$—NH—(CH$_2$)$_u$-A;

n is 1, 2, 3, 4, 5, 6, 7, 8, 9, 11, or 12, s is 1, 2, or 3;

t is 1, 2, or 3;

u is 1, 2, or 3; and

A is

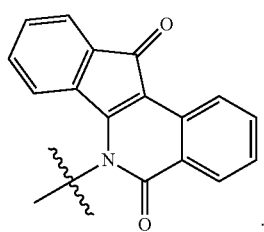 [SMILES: *n1c2c(c3ccccc3c1=O)C(=O)c1ccccc1-2]

One embodiment of the above method is one wherein the compound is

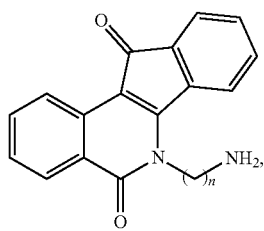

wherein n is 1, 2, 3, 4, 5, 6, 7, 8, 9, 10, 11, or 12, or a pharmaceutically acceptable salt thereof.

One embodiment of the above method is one wherein the compound is

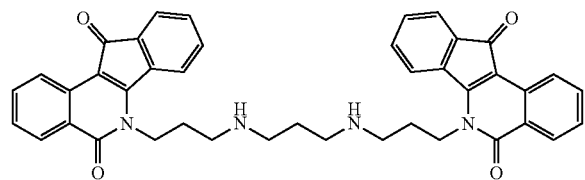 [SMILES: O=C1c2ccccc2-c2c1c1ccccc1c(=O)n2CCCNCCCNCCCn1c2c(c3ccccc3c1=O)C(=O)c1ccccc1-2]

or a pharmaceutically acceptable salt thereof.

One embodiment of the above method is one wherein $R^T$ is amino, methylamino, or dimethylamino. Another embodiment for the above method is one wherein n is 2, 3 or 4. A further embodiment for the above method is one wherein n is 3.

One embodiment of the above method is one wherein the compound is of the formula

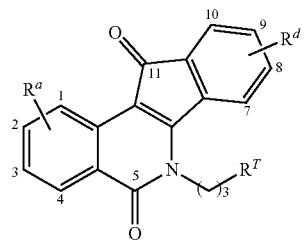

or a pharmaceutically acceptable salt thereof, wherein:
$R^T$ is amino, $R^a$ is 3-amino and $R^d$ is hydrogen; or
$R^T$ is amino, $R^a$ is 3-carboxymethylamino and $R^d$ is hydrogen; or
$R^T$ is amino, $R^a$ is 3-nitro and $R^d$ is 9-methoxy; or
$R^T$ is amino, $R^a$ is 3-amino and $R^d$ is 9-methoxy; or
$R^T$ is amino, $R^a$ is 3-nitro and $R^d$ is 8-methoxy; or
$R^T$ is amino, $R^a$ is 3-nitro and $R^d$ is 7-methoxy; or
$R^T$ is amino, $R^a$ is 3-iodo and $R^d$ is 9-methoxy; or
$R^T$ is dimethylamino, $R^a$ is 3-iodo and $R^d$ is 9-methoxy; or
$R^T$ is dimethylamino, $R^a$ is 3-cyano and $R^d$ is hydrogen.

For any of the above in one embodiment the method is one wherein the disease or condition responsive to tyrosyl-DNA phosphodiesterase I (Tdp1) inhibition is a cancer.

For any of the above in one embodiment the method is one wherein the host animal is a human.

In another embodiment of the invention, there is provided a novel compound of the formula

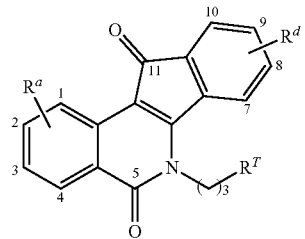

or a pharmaceutically acceptable salt thereof, wherein:
$R^T$ is amino, $R^a$ is 3-carboxymethylamino and $R^d$ is hydrogen; or
$R^T$ is amino, $R^a$ is 3-amino and $R^d$ is 9-methoxy; or
$R^T$ is amino, $R^a$ is 3-nitro and $R^d$ is 8-methoxy; or
$R^T$ is amino, $R^a$ is 3-nitro and $R^d$ is 7-methoxy; or
$R^T$ is amino, $R^a$ is 3-iodo and $R^d$ is hydrogen; or
$R^T$ is dimethylamino, $R^a$ is 3-iodo and $R^d$ is 9-methoxy; or
$R^T$ is dimethylamino, $R^a$ is 3-cyano and $R^d$ is hydrogen.

Another embodiment is a pharmaceutical composition comprising a novel compound as described above and one or more carriers, diluents, or excipients, or a combination thereof. A further embodiment is a method for treating cancer comprising the step of administering a therapeutically effective amount of a novel compound as described above to a patient in need of relief from said cancer.

Another embodiment of the invention is a novel sufonamide compound of the formula

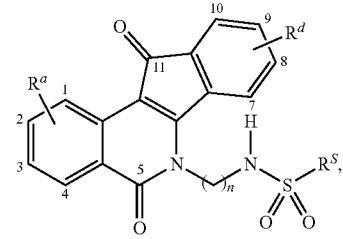

or a pharmaceutically acceptable salt thereof, wherein:
n is 1, 2, 3, 4, 5, 6, 7, 8, 9, 11, or 12,
$R^a$ represents 1-4 substituents each of which is independently selected from the group consisting of hydrogen, halo, hydroxy, optionally substituted (1-4C)alkyl, optionally substituted (1-4C)alkoxy, cyano, nitro, optionally substituted alkylthio, optionally substituted alkylsulfonyl, carboxylic acid and derivatives thereof, and sulfonic acid and derivatives thereof; or $R^a$ represents 2-4 substituents where 2 of said substituents are adjacent substituents and are taken together with the attached carbons to form an optionally substituted heterocycle, and where any remaining substituents are each independently selected from the group consisting of hydrogen, halo, hydroxy, optionally substituted (1-4C)alkyl, optionally substituted (1-4C)alkoxy, cyano, nitro, optionally substituted (1-4C)alkylthio, optionally substituted (1-4C)alkylsulfonyl, carboxylic acid and derivatives thereof, and sulfonic acid and derivatives thereof; and
$R^d$ represents 1-4 substituents each of which is independently selected from the group consisting of hydrogen, halo, hydroxy, optionally substituted (1-4C)alkyl, optionally substituted (1-4C)alkoxy, cyano, nitro, optionally substituted (1-4C)alkylthio, optionally substituted (1-4C)alkylsulfonyl, phenyl (which may bear one or more amino, hydroxyl, halo, thiol, (1-6C)alkyl or halo(1-6C)alkyl substituents), carboxylic acid and derivatives thereof, and sulfonic acid and derivatives thereof; or $R^d$ represents 2-4 substituents where 2 of said substituents are adjacent substituents and are taken together with the attached carbons to form an optionally substituted heterocycle, and where any remaining substituents are each independently selected from the group consisting of hydrogen, halo, hydroxy, optionally substituted (1-4C)alkyl, optionally substituted (1-4C)alkoxy, cyano, nitro, optionally substituted (1-4C)alkylthio, optionally substituted (1-4C) alkylsulfonyl, carboxylic acid and derivatives thereof, and sulfonic acid and derivatives thereof;
$R^S$ is (1-6C)alkyl, (3-7C)cycloalkyl or phenyl, which phenyl may bear one or more amino, hydroxyl, halo, thiol, (1-6C) alkyl or halo(1-6C)alkyl substituents.

A further embodiment of the above novel sufonamide compound is one wherein:
n is 3;
$R^a$ represents 1-2 substituents at the 2-, 3- or 2,3-positions each of which is independently selected from the group consisting of hydrogen, halo, hydroxy, methoxy, cyano and nitro; or $R^a$ represents 2 substituents where said substituents are adjacent 2,3-substituents and are taken together to form (1-2C)alkylenedioxy; and $R^d$ represents 1-2 substituents at the 8-, 9- or 8,9-positions, each of which is independently selected from the group consisting of hydrogen, halo, hydroxy, methoxy and cyano; or $R^d$ represents 2 substituents where said substituents are adjacent substituents and are taken together with the attached carbons to form (1-2C)alkylenedioxy; and $R^S$ is methyl or phenyl, which phenyl may bear a 4-bromo or 4-methyl substituent.

Another embodiment of the above novel sufonamide is the compound of the formula

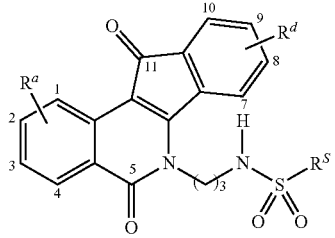

wherein:
$R^a$ represents 3-nitro, 2,3-dimethoxy, or 2,3-methylenedioxy substituents; $R^d$ is hydrogen; and $R^S$ is phenyl. In a further embodiment $R^a$ represents 3-nitro.

Another embodiment of the above novel sufonamide is the compound of the formula

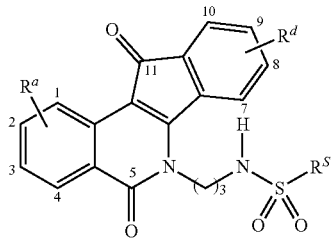

wherein $R^a$ is 2-nitro; $R^d$ is 9-phenyl; and $R^S$ is phenyl.

Another embodiment of the invention is a pharmaceutical composition comprising a novel sufonamide compound as described above and one or more carriers, diluents, or excipients, or a combination thereof. A further embodiment of the invention is a method for treating cancer comprising the step of administering a therapeutically effective amount of a novel sufonamide compound as described above to a patient in need of relief from said cancer.

Another embodiment of the invention is a novel compound of the formula

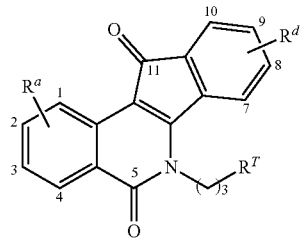

or a pharmaceutically acceptable salt thereof, wherein:
$R^T$ is dimethylamino, $R^a$ is 3-cyano and $R^d$ is 8,9-methylenedioxy; or $R^T$ is 4-morpholinyl, $R^a$ is 3-cyano and $R^d$ is hydrogen; or
$R^T$ is imidazolyl, $R^a$ is 3-cyano and $R^d$ is hydrogen.

Another embodiment of the invention is a pharmaceutical composition comprising a novel compound as described above and one or more carriers, diluents, or excipients, or a combination thereof. A further embodiment of the invention is a method for treating cancer comprising the step of administering a therapeutically effective amount of a novel compound as described above to a patient in need of relief from said cancer.

In addition, various genera and subgenera of each of $R^a$, $R_d$, $R^{a'}$, $R^{d'}$, $R^M$, $R^N$, $R^S$, and $R^T$, X, and n are described herein. It is to be understood that all possible combinations of the various genera and subgenera of each of $R^a$, $R^d$, $R^{a'}$, $R^{d'}$, $R^M$, $R^N$, $R^S$, and $R^S$, X, and n described herein represent additional illustrative embodiments of compounds of the invention described herein. It is to be further understood that each of those additional illustrative embodiments of compounds may be used in any of the compositions, methods, and/or uses described herein. In another embodiment, pharmaceutical compositions containing one or more of the compounds are also described herein. In one aspect, the compositions include a therapeutically effective amount of the one or more compounds for treating a patient with cancer. It is to be understood that the compositions may include other component and/or ingredients, including, but not limited to, other therapeutically active compounds, and/or one or more carriers, diluents, excipients, and the like. In another embodiment, methods for using the compounds and pharmaceutical compositions for treating patients with a cancer are also described herein. In one aspect, the methods include the step of administering one or more of the compounds and/or compositions described herein to a patient with a cancer. In another aspect, the methods include administering a therapeutically effective amount of the one or more compounds and/or compositions described herein for treating patients with a cancer.

It is appreciated herein that the compounds described herein may be used alone or in combination with other compounds useful for treating a cancer, including those compounds that may be therapeutically effective by the same or different modes of action.

In each of the foregoing and each of the following embodiments, it is to be understood that the formulae include and represent not only all pharmaceutically acceptable salts of the compounds, but also include any and all hydrates and/or solvates of the compound formulae. It is appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates.

In each of the foregoing and each of the following embodiments, it is also to be understood that the formulae include and represent each possible isomer, such as stereoisomers and geometric isomers, both individually and in any and all possible mixtures. In each of the foregoing and each of the following embodiments, it is also to be understood that the formulae include and represent any and all crystalline forms, partially crystalline forms, and non crystalline and/or amorphous forms of the compounds.

The compounds described herein may contain one or more chiral centers, or may otherwise be capable of existing as multiple stereoisomers. It is to be understood that in one embodiment, the invention described herein is not limited to any particular sterochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, halo includes fluoro, chloro, bromo and iodo.

As used herein, the term "alkyl" includes a chain of carbon atoms, which is optionally branched. It is to be further understood that in certain embodiments, alkyl is advantageously of limited length, including $C_1$-$C_8$, $C_1$-$C_6$, and $C_1$-$C_4$. Illustratively, such particularly limited length alkyl groups, including $C_1$-$C_8$, $C_1$-$C_6$, and $C_1$-$C_4$ may be referred to as lower alkyl. In embodiments of the invention described herein, it is to be understood, in each case, that the recitation of alkyl refers to alkyl as defined herein, and optionally lower alkyl. Illustrative alkyl, groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, and the like.

As used herein, the term "carboxylic acid and derivatives thereof" includes the group $CO_2H$ and salts thereof, and esters and amides thereof, and CN.

As used herein, the term "sulfonic acid or a derivative thereof" includes $SO_3H$ and salts thereof, and esters and amides thereof.

As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, ($21^{st}$ ed., 2005)).

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

It is also appreciated that the therapeutically effective amount, whether referring to monotherapy or combination therapy, is advantageously selected with reference to any toxicity, or other undesirable side effect, that might occur during administration of one or more of the compounds described herein. Further, it is appreciated that the co-therapies described herein may allow for the administration of lower doses of compounds that show such toxicity, or other undesirable side effect, where those lower doses are below thresholds of toxicity or lower in the therapeutic window than would otherwise be administered in the absence of a cotherapy.

In addition to the illustrative dosages and dosing protocols described herein, it is to be understood that an effective amount of any one or a mixture of the compounds described herein can be readily determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

The term "administering" as used herein includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically-acceptable carriers, adjuvants, and/or vehicles.

Illustrative formats for oral administration include tablets, capsules, elixirs, syrups, and the like.

Illustrative routes for parenteral administration include intravenous, intraarterial, intraperitoneal, epidurial, intraurethral, intrasternal, intramuscular and subcutaneous, as well as any other art recognized route of parenteral administration.

Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

When given systemically, such as parenterally, illustrative doses include those in the range from about 0.01 mg/kg to about 100 mg/kg, or about 0.01 mg/kg to about 10 mg/kg, or about 0.1 mg/kg to about 100 mg/kg, or about 0.1 mg/kg to about 10 mg/kg.

When given systemically, such as orally, illustrative doses include those in the range from about 0.1 mg/kg to about 1000 mg/kg, or about 0.1 mg/kg to about 100 mg/kg, or about 0.1 mg/kg to about 10 mg/kg, or about 1 mg/kg to about 1000 mg/kg, or about 1 mg/kg to about 100 mg/kg, or about 1 mg/kg to about 10 mg/kg.

In another illustrative embodiment, the compound is administered parenterally systemically q.d. at a dose of about 0.1 mg/kg, or about 0.5 mg/kg, or about 1 mg/kg, or about 5 mg/kg, or about 10 mg/kg, or about 50 mg/kg of body weight of the patient.

In making the pharmaceutical compositions of the compounds described herein, a therapeutically effective amount of one or more compounds in any of the various forms described herein may be mixed with one or more excipients, diluted by one or more excipients, or enclosed within such a carrier which can be in the form of a capsule, sachet, paper, or other container. Excipients may serve as a diluent, and can be solid, semi-solid, or liquid materials, which act as a vehicle, carrier or medium for the active ingredient. Thus, the formulation compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders. The compositions may contain anywhere from about 0.1% to about 99.9% active ingredients, depending upon the selected dose and dosage form.

Illustrative examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions can be formulated so as to provide quick, sustained or delayed release of the active ingredient after administration to the patient by employing procedures known in the art. It is to be understood that one or more carriers, one or more diluents, one or more excipients, and combinations of the foregoing may be used in making the pharmaceutical compositions described herein. It is appreciated that the carriers, diluents, and excipients used to prepare the compositions described herein are advantageously GRAS (generally regarded as safe) compounds.

Illustrative examples of emulsifying agents include naturally occurring gums (e.g., gum acacia or gum tragacanth) and naturally occurring phosphatides (e.g., soybean lecithin and sorbitan monooleate derivatives). Examples of antioxidants are butylated hydroxy anisole (BHA), ascorbic acid and derivatives thereof, tocopherol and derivatives thereof, butylated hydroxy anisole, and cysteine. Examples of preservatives are parabens, such as methyl or propyl p-hydroxybenzoate, and benzalkonium chloride. Examples of humectants are glycerin, propylene glycol, sorbitol, and urea. Examples of penetration enhancers are propylene glycol, DMSO, triethanolamine, N,N-dimethylacetamide, N,N-dimethylformamide, 2-pyrrolidone and derivatives thereof, tetrahydrofurfuryl alcohol, and AZONE. Examples of chelating agents are sodium EDTA, citric acid, and phosphoric acid. Examples of gel forming agents are CARBOPOL, cellulose derivatives, bentonite, alginates, gelatin and polyvinylpyrrolidone. Examples of ointment bases are beeswax, paraffin, cetyl palmitate, vegetable oils, sorbitan esters of fatty acids (Span), polyethylene glycols, and condensation products between sorbitan esters of fatty acids and ethylene oxide (e.g., polyoxyethylene sorbitan monooleate (TWEEN)).

Solid Dosage Forms for Oral Use. Formulations for oral use include tablets containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug substance in a predetermined pattern (e.g., in order to achieve a controlled release formulation) or it may be adapted not to release the active drug substance until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material such as, e.g., glyceryl monostearate or glyceryl distearate may be employed.

The solid tablet compositions may include a coating adapted to protect the composition from unwanted chemical changes, (e.g., chemical degradation prior to the release of the active drug substance). The coating may be applied on the solid dosage form in a similar manner as that described in Encyclopedia of Pharmaceutical Technology.

Controlled Release Oral Dosage Forms. Controlled release compositions for oral use may, e.g., be constructed to release the active drug by controlling the dissolution and/or the diffusion of the active drug substance.

Parenteral Compositions. The pharmaceutical composition may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

As indicated above, the pharmaceutical compositions described herein may be in the form suitable for sterile injection. To prepare such a composition, the suitable active drug(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

The examples in the following disclosures further illustrate specific embodiments of the invention; however, the following illustrative examples should not be interpreted in any way to limit the invention.

Further aspects and embodiments of the invention are set out in the following descriptions, published at (A) J. Med. Chem. 2012, 55, 4457-4478 and (B) J. Med. Chem. 2013, 56, 182-200, each of which is incorporated by reference.

Abbreviations used herein include the following: APCI-MS, atmospheric-pressure chemical ionization mass spectrometry; BBO, multinuclear broadband observe; CI/EIMS, chemical ionization/electron impact mass spectrometry; CPT, camptothecin; DMAP, 4-dimethylaminopyridine; DMSO-$d_6$, dimethyl-$d_6$ sulfoxide; EIMS, electron impact mass spectrometry; ESIMS or ESI-MS, electrospray ionization mass spectrometry; HRMS, high resolution mass spectrometry; PTSA, p-toluenesulfonic acid; QNP, quattro nucleus probe; SCAN1, spinocerebellar ataxia with axonal neuropathy; Tdp1, tyrosyl-DNA phosphodiesterase I; TFA, trifluoroacetic acid; Top1, topoisomerase type I; TsCl, p-toluenesulfonyl chloride.

(A) J. Med. Chem. 2012, 55, 4457-4478

Figure 1:
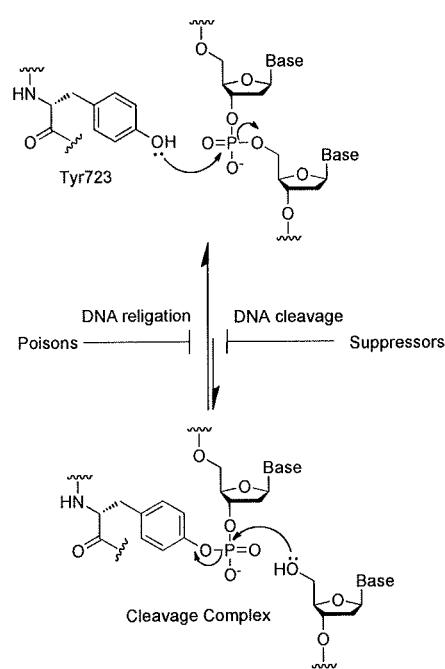
FIG. 1 shows Scheme 1. Tdp1 in Action.

Eukaryotic topoisomerase I (Top1) is an essential enzyme for many critical cellular processes as it relaxes the double helix structure of DNA so that the stored genetic information can be accessed during DNA replication, transcription and repair. The mechanism of action of Top1 starts with the nucleophilic attack of the enzyme Tyr723 hydroxyl group on a phosphodiester linkage in DNA, displacing the 5'-end to become covalently attached to the 3'-end of DNA, thus forming a "cleavage complex." The religation reaction occurs faster than cleavage so the equilibrium favors the uncleaved DNA (FIG. 1, Scheme 1).

Under normal circumstances, the Top1-DNA cleavage complex is a transitory intermediate in the Top1-catalyzed reaction, as the broken DNA strand is quickly religated after a local supercoil has been removed. However, Top1 can become stalled in the DNA cleavage complex under a variety of natural or unnatural conditions in which the rate of religation is inhibited or reduced. For example, Top1 inhibitors, such as camptothecin (CPT, 1) and its clinically used derivatives (topotecan (2), irinotecan (3), and belotecan), as well as other non-CPT Top1 inhibitors like indenoisoquinolines (indotecan (4), and indimitecan (5)), inhibit the religation rate by selectively and reversibly binding to the Top1-DNA interface. This ultimately leads to cell death after collision of the cleavage complex with the replication fork resulting in double-strand breakage. Other naturally occurring DNA lesions, such as strand breaks, abasic sites, base mismatches, and certain oxidized or modified bases, can also induce stalled Top1-DNA complexes via the misalignment of the 5'-hydroxyl with the tyrosyl-DNA phosphodiester linkage, thus physically blocking the Top1 religation reaction. Under these conditions, cellular DNA metabolism results in repair of the stalled Top1-DNA cleavage complex by DNA ligase, which cannot work until the protein adduct is removed, and the broken DNA strand is provided with termini consisting of a 5'-phosphate on one end and a 3'-hydroxyl on the other end for DNA repair. In detail, the overall process involves the following steps:

1) Tdp1 hydrolyzes the phosphotyrosyl linkage between degraded Top1 and DNA;

2) polynucleotide kinase phosphatase (PNKP) hydrolyzes the resulting 3'-phosphate end and catalyzes the phosphorylation of the 5'-hydroxyl end of the broken DNA strand. This results in a broken DNA strand with termini consisting of a 5'-phosphate and 3'-hydroxyl for DNA repair.

3) DNA polymerase β replaces the missing DNA segment; and finally 4) DNA ligase III reseals the broken DNA.

Tyrosyl-DNA phosphodiesterase I (Tdp1) has been shown to be the only enzyme that specifically catalyzes the hydrolysis of the phosphodiester bond between the catalytic Tyr723 of Top1 and DNA-3'-phosphate. Hence, Tdp1 is thought to be associated with the repair of DNA lesions. The cellular importance of Tdp1 also stems from the fact it is ubiquitous in eukaryotes and plays an important physiological role, as the homozygous mutation H493R in its active site is responsible for the rare autosomal recessive neurodegenerative disease called spinocerebellar ataxia with axonal neuropathy (SCAN1). Tdp1 also has the ability to remove the 3'-phosphoglycolate caused by oxidative DNA damage and bleomycin and repair trapped Top2-DNA cleavage complexes. All this evidence suggests that Tdp1 assumes a broader role in the maintenance of genomic stability. Hence, this makes Tdp1 a rational anticancer drug development target.

Figure 2:
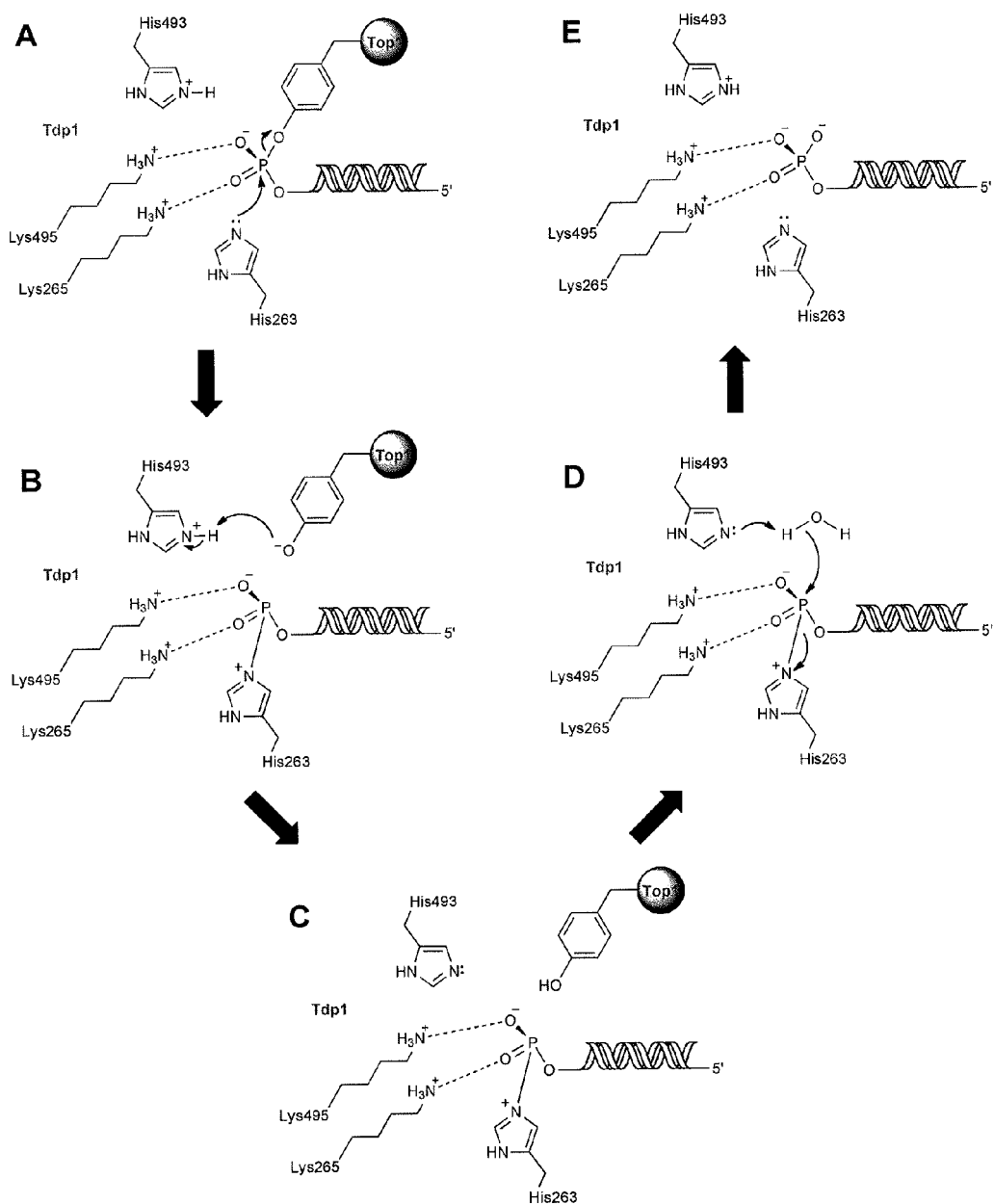
FIG. 2 shows Scheme 2. Tdp1 in Action.

Tdp1 is a member of the phospholipase D superfamily of enzymes that catalyze the hydrolysis of a variety of phosphodiester bonds in many different substrates. Crystallographic studies have revealed that human Tdp1 is composed of two domains related by a pseudo-twofold axis of symmetry. Each domain contributes a histidine and a lysine residue to form an active site that is centrally located at the symmetry axis. Four additional residues N283, Q294, N516, and E538 are also positioned near the active site. The crystal structure of Tdp1 in the quaternary complex with a vanadate ion, a Top1-derived peptide, and a single-stranded DNA oligonucleotide revealed an active site in which the DNA moiety occupies a relatively narrow cleft rich in positive charges, while the peptide moiety binds in another region of the active site characterized by a relatively large, more open cleft that contains a mixed charge distribution. The trigonal bipyramidal geometry exhibited by the vanadate implies an $S_N2$ mechanism for nucleophilic attack on phosphate. Therefore, the mechanism of action of Tdp1 is proposed to start with a nucleophilic attack on the phosphotyrosyl bond by the catalytic H263 residue in the N-terminal domain while the H493 residue in the C-terminal domain acts as a general acid and donates a proton to the tyrosine-containing peptide leaving group (FIG. 2, Scheme 2). The resulting phosphoramide is stabilized by hydrogen-bonding with catalytic K265 and K495. Hydrolysis of this covalent intermediate occurs via a second $S_N2$ reaction by a water molecule with the H493 residue acting as a general base. This proposed reaction step is supported by in vitro studies showing that the SCAN1

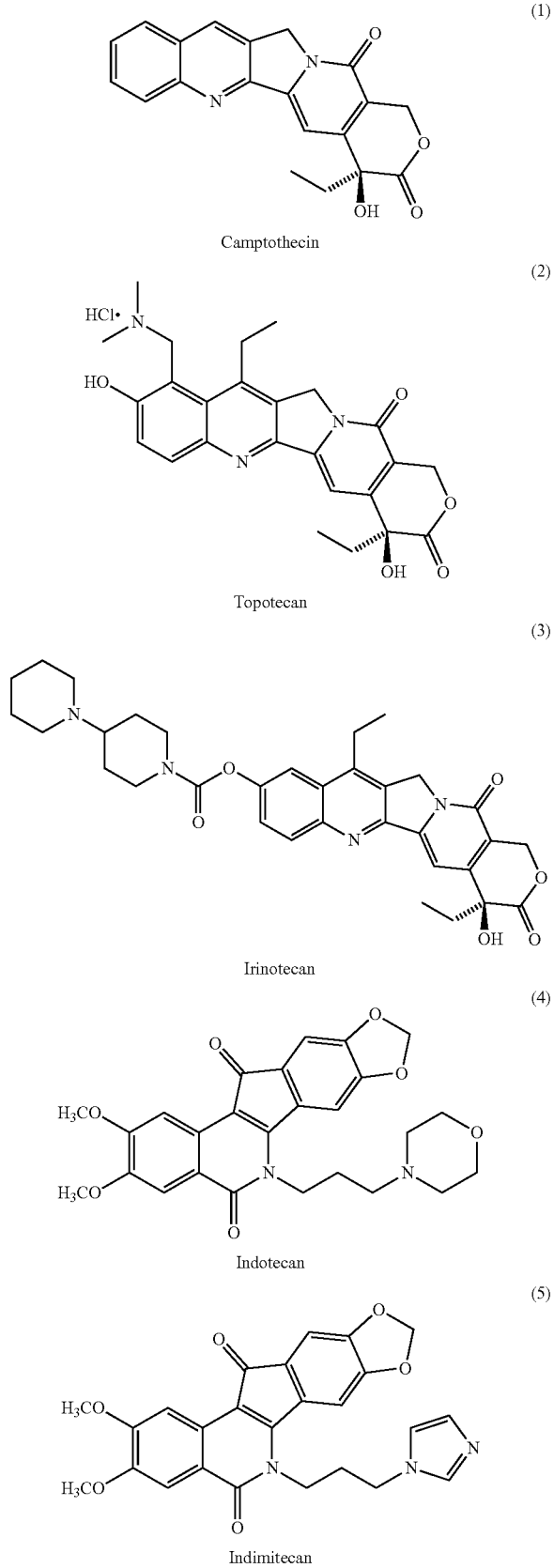

Camptothecin (1)

Topotecan (2)

Irinotecan (3)

Indotecan (4)

Indimitecan (5)

H493R mutation leads to an accumulation of Tdp1-DNA covalent intermediate. The final product in this process is a DNA molecule with a 3'-phosphate end.

Because the Top1-DNA phosphotyrosyl bond is buried deep within the Top1-DNA complex and is inaccessible to Tdp1, prior denaturation of the Top1-DNA complex or proteolytic degradation of Top1 is required for the Tdp1 enzymatic activity. However, Tdp1 seems to be equally effective against many structural variations of DNA, including single-strand, tailed duplex, and gapped duplex, though the activity decreases as the oligonucleotide length is shortened. These observations have implied that the enzymatic activity of Tdp1 is influenced by the length of Top1-derived polypeptide chain and the structure of the DNA segment bound to Top1. Moreover, studies from SCAN1 cells provided evidence for Tdp1 participation in the repair of Top1-mediated DNA damage and for the hypersensitivity to camptothecin in human cells with a single defect in Tdp1 activity. These observations suggest the possibility of developing Tdp1 inhibitors that can potentiate the cytotoxic effects of Top1 inhibitors in anticancer drug therapy.

To date, there are very few known Tdp1 inhibitors, and their potencies and specificities leave much room for improvement. For example, both vanadate and tungstate can mimic the phosphate in the transition state, thus expressing inhibition at millimolar concentrations. However, due to poor specificity and hypersensitivity to all phosphoryl transfer reactions, they cannot serve as pharmacological inhibitors. Other Tdp1 inhibitors are the aminoglycoside neomycin, which has very low potency at $IC_{50}=8$ mM, or furamidine (6), which produces reversible and competitive inhibition of Tdp1 with an $IC_{50} \approx 30$ µM. However, 6 has additional targets because of its DNA binding activities, which also makes experimental data difficult to interpret. The steroid NSC 88915 (7) was recently identified via high-throughput screening as a potent and specific Tdp1 inhibitor with an $IC_{50}=7.7$ µM.

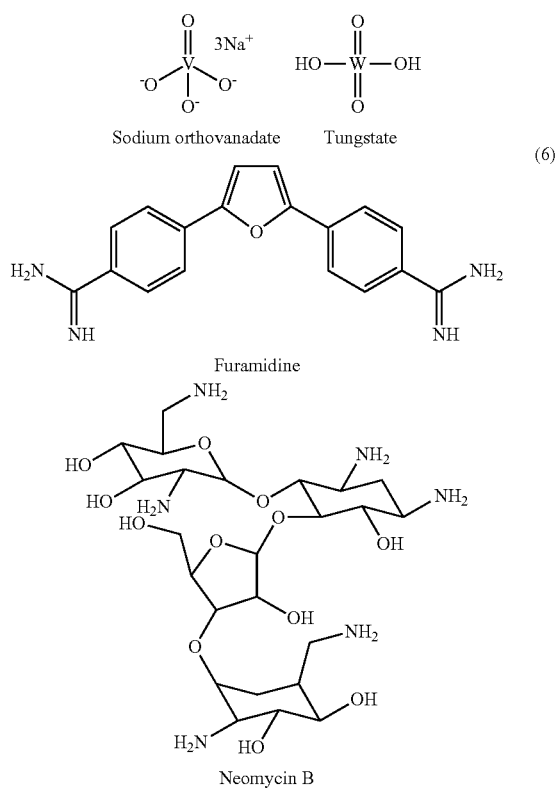

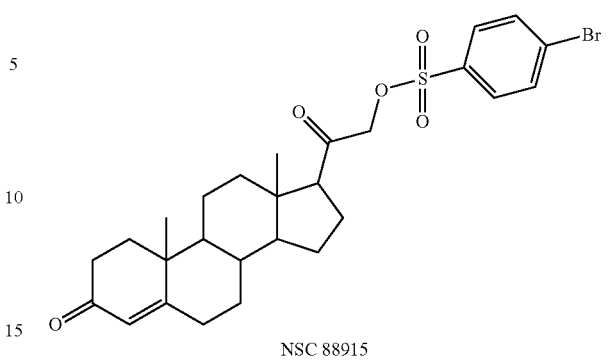

However, this compound expressed some common pharmacokinetic problems in cellular systems such as limited drug uptake, poor cytotoxicity, and off-target effects. Therefore, there is an urgent need to design and develop potent Tdp1 inhibitors that can overcome these drawbacks. Furthermore, potential anticancer agents that would possess both Tdp1 and Top1 inhibitory activities are attractive because the two types of activities could act synergistically.

Screening of a focused library of indenoisoquinolines led to the discovery of three potent Tdp1 inhibitors (Table 1). These Tdp1-active n-alkylamino-containing indenoisoquinolines 77-79 (n=10-12), which had been synthesized previously by Morrell et al., did not display Top1 inhibition or were very weak inhibitors, although other homologous compounds with shorter linkers (69-71, n=2-4) were good Top1 inhibitors. This led to the idea that Tdp1 inhibition may potentially be present in Top1 inhibitors with a shorter side chain.

TABLE 1

Tdp1 Inhibitory Activities of n-Alkylamino Indenoisoquinolines

Compound 77-79

| n | $IC_{50}$ (µM) recombinant $Tdp_1$ | $^a Top_1$ |
|---|---|---|
| 10 | 14 | 0 |
| 11 | 13 | + |
| 19 | 15 | 0/+ |

$^a$Compound-induced DNA cleavage due to Top1 inhibition is graded by the following semiquantitative relative to 1 µM camptothecin (1): 0, no inhibitory activity; +, between 20 and 50%, activity; ++, between 50 and 75% activity; +++, between 75% and 95% activity; ++++, equipotent. The 0/+ ranking is between 0 and +.

Figure 4:
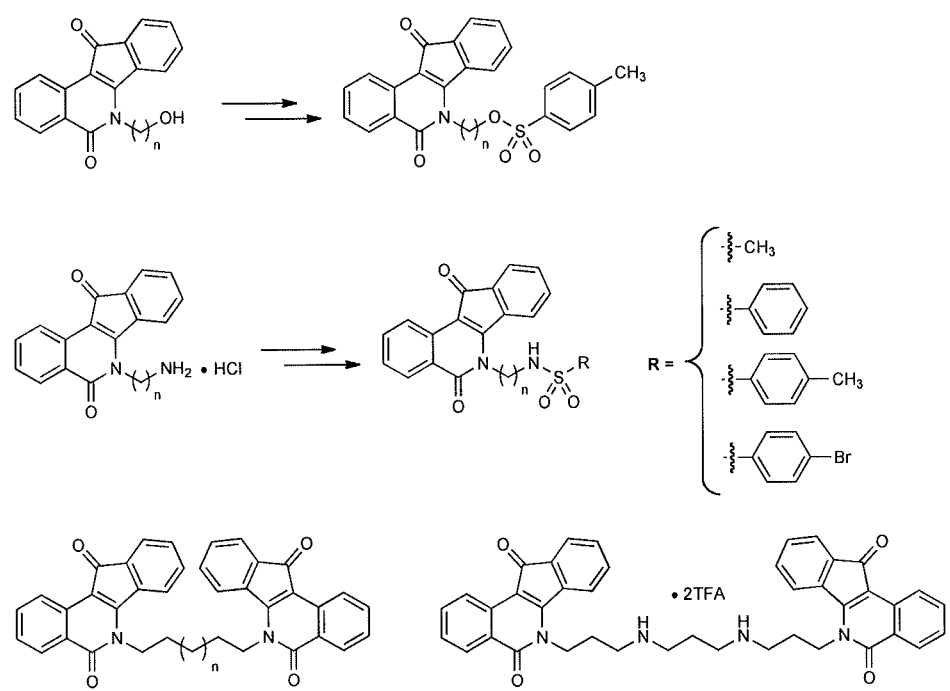
FIG. 4 shows compounds proposed for synthesis.

In addition, previous studies reported the importance of the sulfonate functional group in conferring the Tdp1 inhibitory activity of steroid 7 since this group mimics the phosphotyrosyl bond in the Top1-DNA complex. This led to the hypothesis that sulfonate analogues of the indenoisoquinolines in Table 1 might function as Tdp1 inhibitors. This hypothesis was also supported by GOLD docking and energy minimization of one hypothetical sulfonate (25, n=3) in the crystal structure of Tdp1 (1RFF) after deleting the polydeoxyribonucleotide 5'-D(*AP*GP*TP*T)-3', vanadate (VO₄³⁻), and the Top1-derived peptide residues 720-727 (mutation L724Y). The docking results revealed a structure that resembles the original structure: the tosylate moiety matched the phosphotyrosine the sulfonate was in place of the vanadate, the alkyl chain played the "spacer" role of the deoxyribose, and the indenoisoquinoline system overlapped with a thymine of DNA (FIG. 3). This result is in agreement with those reported for steroid 7. Since a sulfonamide bond is well known to be more metabolically stable than sulfonate, and the current compounds possess a structural handle (amino group) that can be used to install a sulfonyl linkage, a series of indenoisoquinoline sulfonates and sulfonamides with different linker lengths (n=2-12) were synthesized in order to investigate how the structures of these indenoisoquinolines resemble the substrate of the Tdp1-catalyzed reaction. Moreover, a previous study on steroid 7 indicated that different substituents on the phenyl ring may have positive effects on Tdp1 inhibitory activity. Therefore, four different groups were placed at the sulfonamide position (FIG. 4).

Synthesis of Indenoisoquinoline Sulfonates

The key starting material in the synthesis of all of the desired compounds is lactone 11, which was synthesized based on the procedure reported by Morrell et al. The reaction of 2-carboxybenzaldehyde (8) and phthalide (9) in the presence of sodium methoxide in methanol yielded the intermediate 10, which formed lactone 11 upon cyclization under acidic conditions in a one-pot synthesis carried out with the aid of a Dean-Stark trap. The synthetic route to indenoisoquinoline sulfonates 24-29 involved the preparation of n-hydroxyalkyl indenoisoquinolines 18-23 from the reaction of lactone 11 and n-aminoalcohols 12-17 for 3-6 hours. The sulfonylation of compounds 19-23 to afford indenoisoquinoline sulfonates 25-29 was achieved in dichloromethane (Scheme 3).

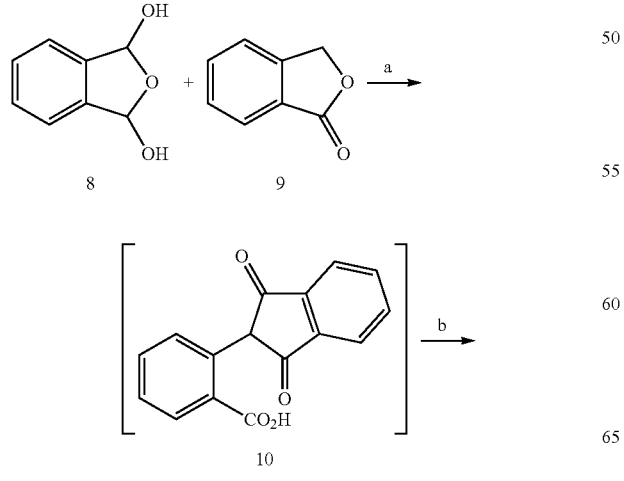

Scheme 3. Synthesis of Indenoisoquinoline Sulfonates

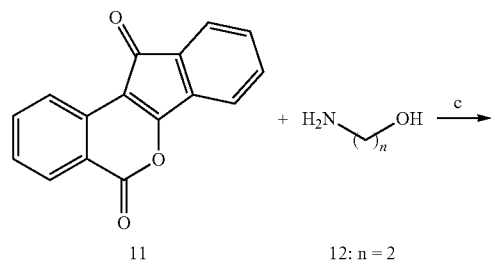

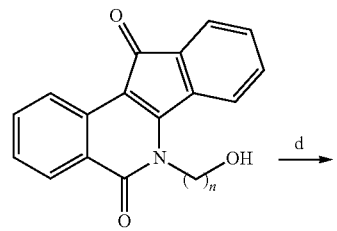

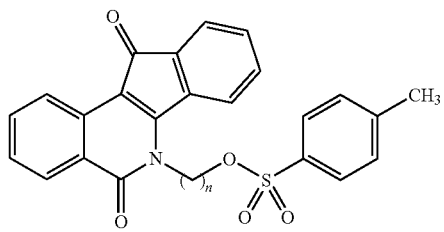

Reagents and conditions: (a) NaOMe, MeOH, EtOAc, 65° C.;
(b) HCl, PTSA, benzene, reflux; (c) CHCl₃, reflux;
(d) TsCl, DMAP, CH₂Cl₂, Et₃N, rt.

However, the sulfonylation of 2-hydroxyethyl indenoisoquinoline 18 under the same conditions failed to yield the desired sulfonate product 24, but instead gave the chloride analogue 30 or, in the presence of silver acetate, the acetate analogue 31 (Scheme 4). Silver acetate was initially meant to quench the nucleophilic attack of the chloride ions in the hope of obtaining the sulfonate 24, and the side product 31 was unexpected.

Scheme 4. Formation of the Undesired Chloride (30) and Acetate (31) Analogues

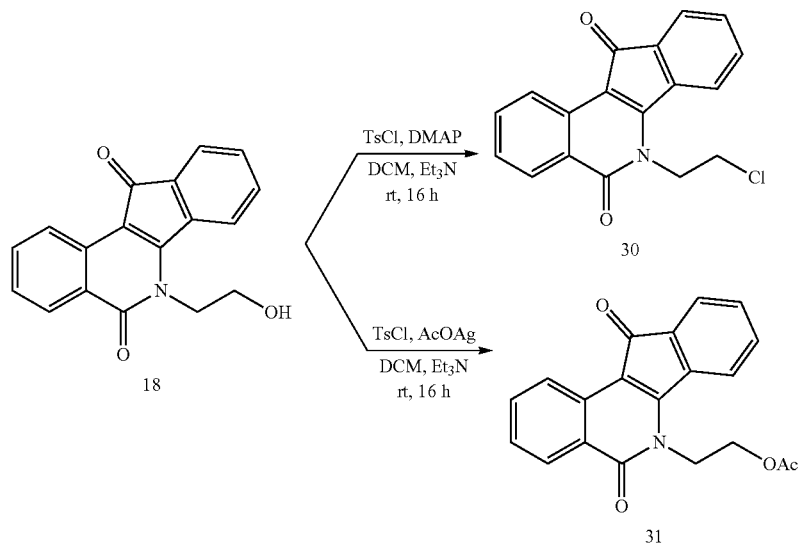

Two mechanisms are proposed for this transformation with the sulfonate 24 assumed to be the first intermediate (Scheme 5). In the first proposed mechanism, 24 undergoes intramolecular cyclization and elimination of the tosylate group to yield a 4,5-dihydro-3-oxazolium intermediate 32. Nucleophilic attack of the chloride anion yields the substituted 2-chloroethyl indenoisoquinoline 30. The presence of silver ion facilitates the displacement of chloride by acetate to form 31. In the second mechanism, chloride displaces the tosylate directly to form 31. This mechanism does not explain why the alcohol 18 undergoes a unique reaction pathway.

Scheme 5. Proposed Mechanisms for the Formation of Chloride 30 and Acetate 31.

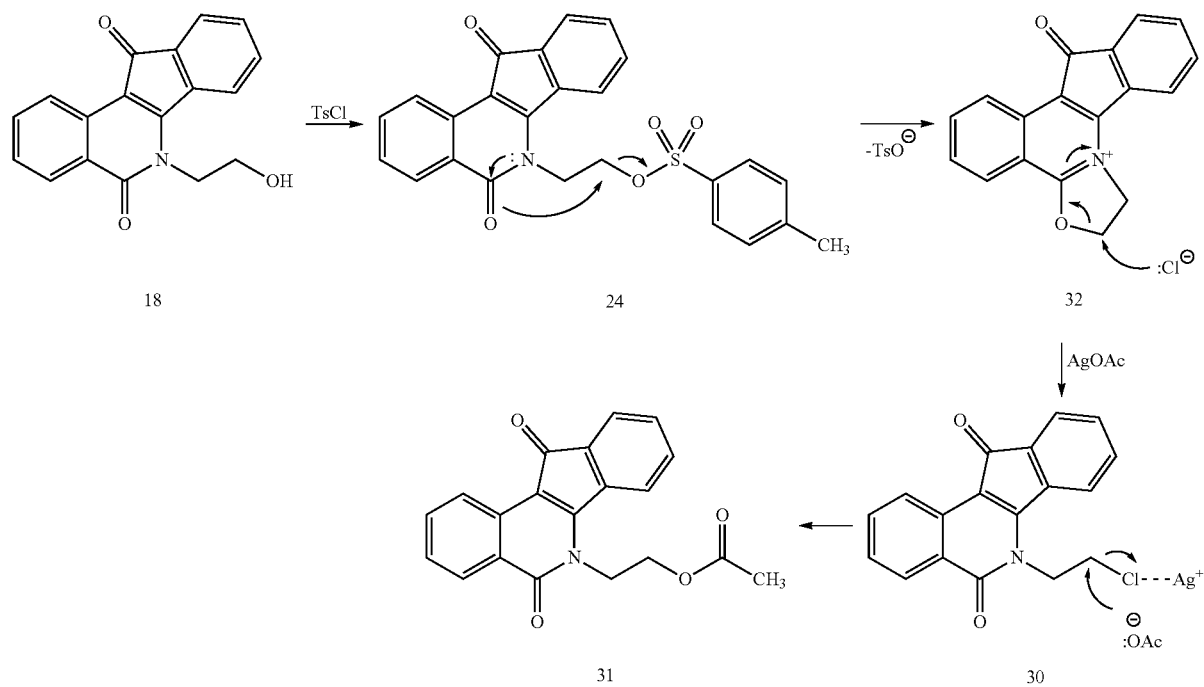

Mechanism 2:

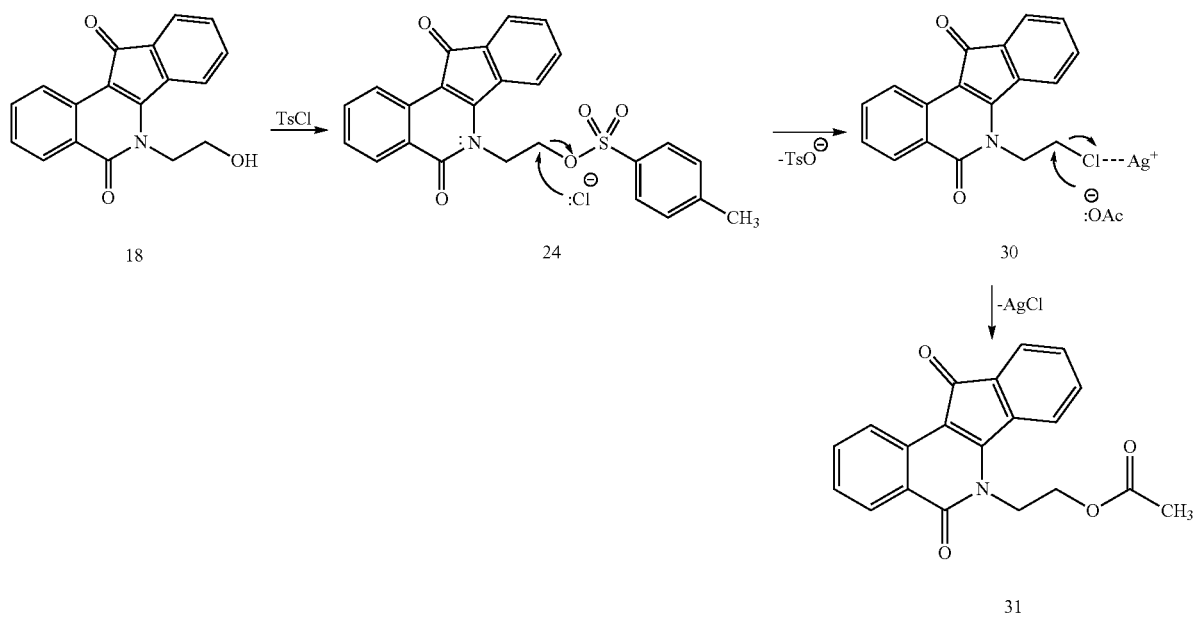

An independent study of the feasibility of displacing the chloride by acetate was done by mixing and stirring chloride 30 and silver acetate in dichloromethane without the presence of any base at room temperature for 24 hours. The result showed that 30 was incompletely converted to the acetate 31 and, surprisingly, to alcohol 18. This result implied the sensitivity of acetate 31 to hydrolysis and its instability in solution.

7-Hydroxyheptyl indenoisoquinoline 23 could be prepared from lactone 11 and the commercially available 7-amino-1-heptanol (17) as depicted in Scheme 3. However, due to the very high cost of 17 (and any n-aminoalcohol with more than 6 methylene units) several alternative routes were considered for making 23. Aminoalcohol 17 can be readily prepared from the reaction of its low-cost 7-bromo analogue 33 with sodium azide in $CHCl_3$ to afford an azido intermediate, which yields 17 upon reduction with Fe in aqueous ammonia (Scheme 6A). However, since this route poses an explosion hazard because of the instability of the azido compound and the possible formation of the very explosive di- and triazidomethane (from $CHCl_3$) during work-up, an alternative route was utilized to make 17 under safer and milder conditions using the classical Delépine reaction (Scheme 6B). In this method, urotropine 34 was alkylated by the 7-bromoalcohol 33 to produce a quaternary hexamethylenetetramine salt 35, which produced the 7-aminoalcohol 17 in good yield upon acidic hydrolysis in ethanol. Another advantage of this method is that intermediate 17 requires no purification and can react with lactone 11 to afford 23 in very high purity.

Scheme 6. Alternative Routes to Synthesize 17

A. POTENTIALLY MORE EXPLOSIVE!

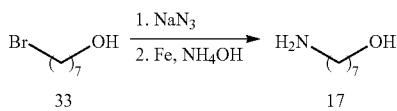

B. SAFER & GREENER

Synthesis of Indenoisoquinoline Sulfonamides

Figure 5:
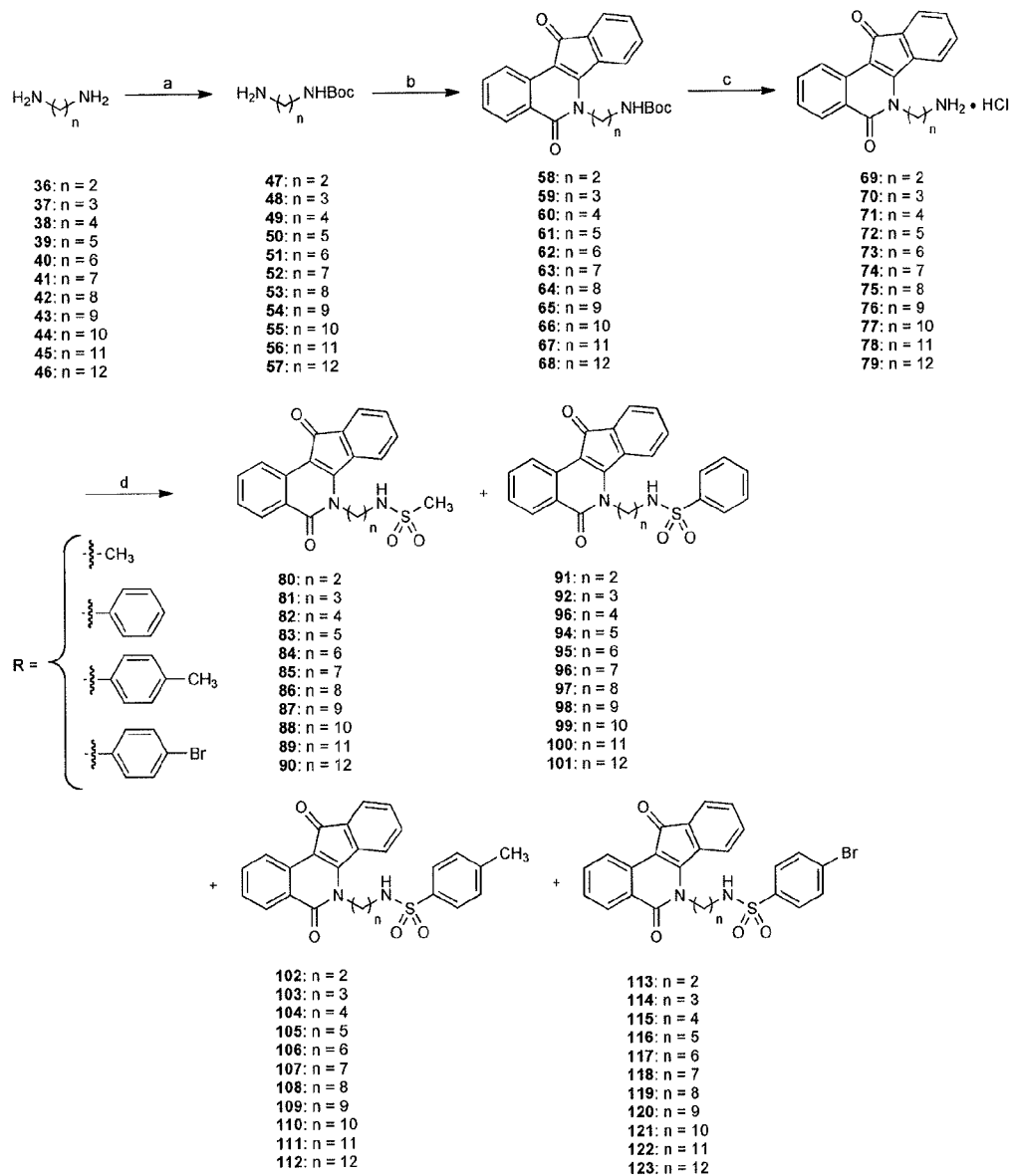
FIG. 5 shows Scheme 7. Synthesis of Indenoisoquinoline Sulfonamides.

All the desired n-alkylamino indenoisoquinoline hydrochloride salts 69-79 were synthesized based on the procedures reported by Morrell et al. as follows: the diamines 36-46 were Boc protected at one end by using a 5:1 diamine:$Boc_2O$ ratio. The mono-Boc-protected products 47-57 were treated with lactone 11 in a 1:1 ratio to give the Boc-protected indenoisoquinolines 58-68 in high yields, which, upon deprotection of the amines in methanolic HCl, provided the indenoisoquinoline hydrochloride salts 69-79. All of the indenoisoquinoline sulfonamides with methyl (80-90), phenyl (91-101), p-methylphenyl (102-112), and p-bromophenyl (113-123) substituents were synthesized in good to excellent yields by gently heating each hydrochloride salt at 70° C. with a corresponding sulfonating reagent (mesyl, benzenesulfonyl, tosyl, or p-bromobenzenesulfonyl chloride) in 1:2 ratio in the presence of triethylamine (2 equiv) for 16 h (FIG. 5, Scheme 7).

Figure 6:
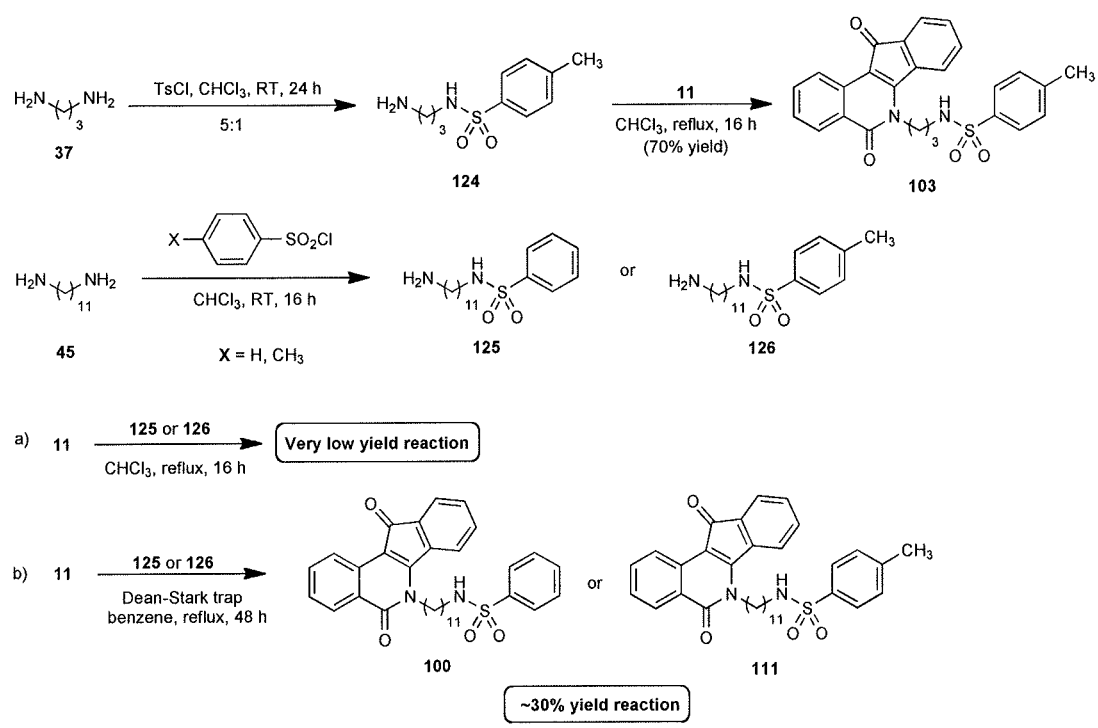
FIG. 6 shows Scheme 8. Alternative Synthetic Route to Indenoisoquinoline Sulfonamides.

A different synthetic route to the indenoisoquinoline sulfonamides was investigated as follows: 1) the sulfonamide group was incorporated into the linker chain by having the sulfonating reagents (mesyl, benzenesulfonyl, tosyl, or p-bromobenzenesulfonyl chloride) react with diamines in a 1:5 molar ratio, with the procedure for these reactions being similar to that of making mono-Boc-protected diamines; 2) heating the mono-sulfonated diamines with lactone 11 in a 1:1 molar ratio under reflux to obtain the desired sulfonamides (FIG. 6, Scheme 8). The advantage of this approach is that the introduction and removal of the protecting Boc group were skipped, thus providing a shorter route to make sulfonamides with hypothetically higher overall yields. However, the apparent weakness is that derivatization of side chains at the sulfonamide end would be impossible. Nevertheless, this idea was first tested by the reaction of N-(3-aminopropyl)-4-methylbenzenesulfonamide (124) with lactone 11 to give sulfonamide 103 in 70% yield. Following this success, N-(11-aminoundecyl)-4-methylbenzenesulfonamide (125) and N-(11-aminoundecyl)benzenesulfonamide (126) were synthesized to use in the next reaction with lactone 11. However, the condensation occurred very slowly in $CHCl_3$ and a significant amount of starting materials was observed even after 48 h of heating at reflux. Then benzene was employed to help remove $H_2O$ from the reaction mixture in order to force the equilibrium to the product side, but the reaction provided only about 30% yield of crude product after 2 days of heating, and starting materials were still present in the mixture. Hence, the original method was utilized to make all of the desired sulfonamides 80-123.

Synthesis of Bisindenoisoquinolines and Other Compounds

Figure 7:
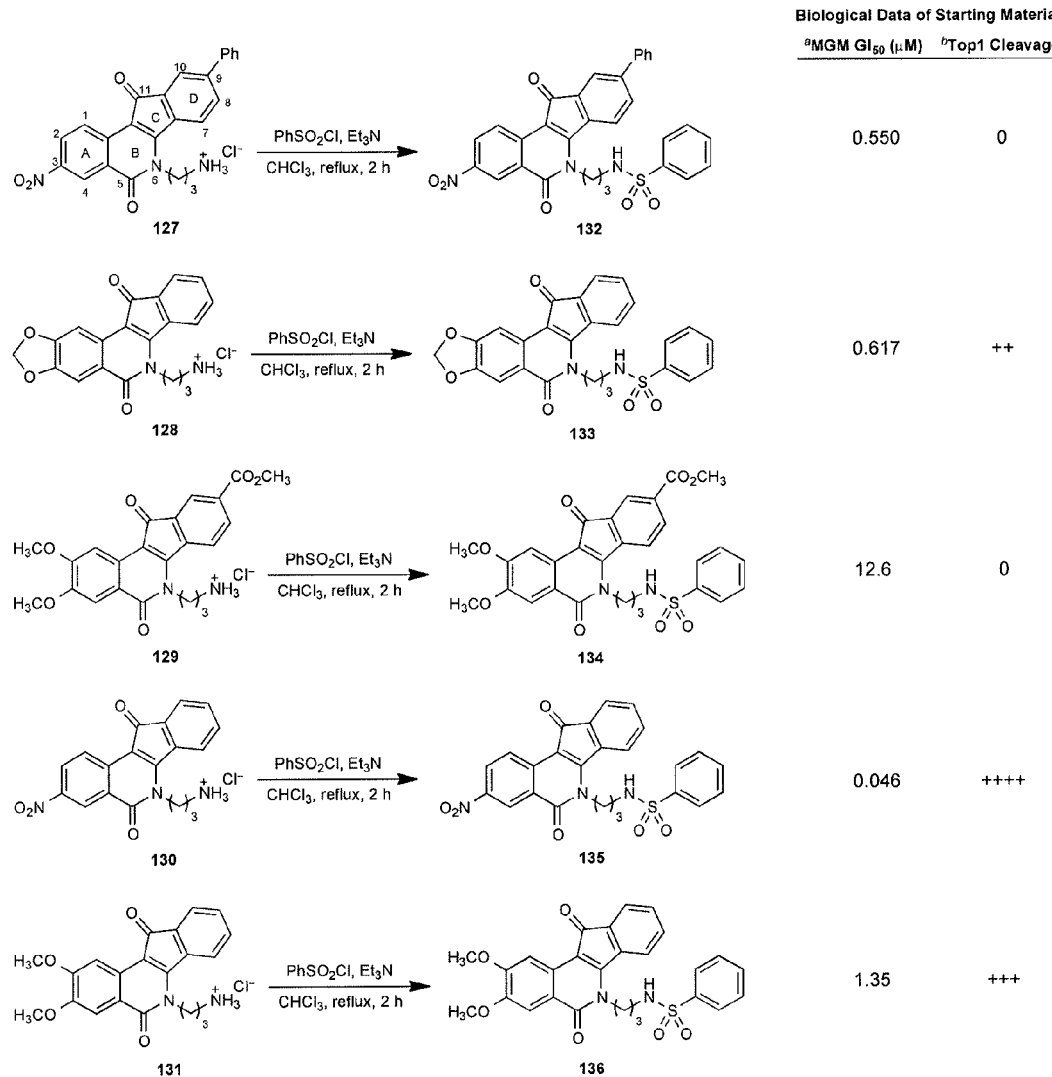
FIG. 7 shows Ring-substituted Indenoisoquinoline Sulfonamides. [a]The cytotoxicity $GI_{50}$ values are the concentrations corresponding to 50% growth inhibition. The MGM is the mean graph midpoint for growth inhibition of all 60 human cancer cell lines successfully tested, ranging from $10^{-8}$ to $10^{-4}$ molar, where values that fall outside the range were taken as $10^{-8}$ and $10^{-4}$ molar.

The goal of this project was to achieve dual Top1-Tdp1 inhibition, and this was attempted by making sulfonamides from substrates that have been shown to be active against Top1 by previous biological assays (FIG. 7). The presence of a bulky substituent at position 9 on the D-ring of the indenoisoquinoline system attenuates Top1 inhibition, as seen in compounds 127 and 129 (see structure 127 in FIG. 7 for indenoisoquinoline numbering). Nevertheless, in order to gain a quick look into the effects of various substituents on the A- and D-rings of the indenoisoquinoline system to Tdp1 inhibitory activity, all the starting materials 127-131 were subjected to similar reaction conditions to obtain the corresponding sulfonamides 132-136 (FIG. 7). In addition, three bis(indenoisoquinlines) 140-142 were prepared by heating two equivalents of lactone 11 with diamines 137-139 at reflux for 16 h. Polyamino bis(indenoisoquinline) 145 was synthesized based on the procedure reported by Morrell et al. (FIG. 8, Scheme 9).

Biological Results

Tdp1 inhibitory activity was measured by the drug's ability to inhibit the hydrolysis of the phosphodiester linkage between tyrosine and the 3'-end of the DNA substrate, and to prevent the generation of an oligonucleotide with a free 3'-phosphate (N14P). Therefore, the disappearance of the gel band for N14P indicated Tdp1 inhibition. The Tdp1 catalytic gel-based assay is represented in FIG. 9, and representative gels demonstrating dose-dependent Tdp1 inhibition by some indenoisoquinoline amine hydrochlodrides are depicted in FIG. 10.

Additionally, all indenoisoquinoline sulfonates and sulfonamideas were tested for Top1 cleavage complex poisoning in a Top1-mediated DNA cleavage assay. The potency of a compound against Top1 is correlated to the intensities of the bands corresponding to DNA fragments in this assay, and is graded by the following semiquantitative scale relative to 1 µM camptothecin: 0, no inhibitory activity; +, between 20% and 50% activity; ++, between 50% and 75% activity; +++, between 75% and 95% activity; ++++, equipotent. The Tdp1 and Top1 activities of all target compounds are represented in FIG. 11.

The indenoisoquinoline amine hydrochlorides 69-79 were shown to be Tdp1 inhibitors ($IC_{50}$=13 to 55 µM). Despite being less active than steroid 7 ($IC_{50}$=7.7 µM), their potencies were retained in whole cell extract (WCE), while the steroid expressed off-target effects and lost its potency in cellular environments. Notably, compounds with longer linkers (n=10-12) showed higher Tdp1 inhibition than those with shorter side chains, while the Top1 inhibition trend was the opposite. It is known that the optimal length of the side chain at the lactam position in Top1 indenoisoquinoline inhibitors is three methylene units (propyl). Molecular modeling indicated that an increase in hydrophobicity as a direct result of increased linker length in these Top1 inhibitors caused negative interactions with the hydrated binding pocket of the Top1-DNA cleavage complex. That explained the decrease in Top1 inhibition of this series as the number of methylene units increase. This is, however, not the case for Tdp1 inhibition. Though the present results for Tdp1 inhibition do not show a linear correlation of chain length and potency, they indicate that the longer chains may gain favorable hydrophobic interactions in the binding site of Tdp1. Additionally, hypothetical models show that the lactam side chain protrudes towards the major groove of DNA and causes minimal steric clashes within the binding pocket in the Top1-DNA cleavage complex. Similar conclusions can be drawn for Tdp1: since no significant reduction in activity was observed in the series with increasing chain length, the lactam side chain must be well accommodated. Indenoisoquinolines with n=3 and 4 (compounds 70 and 71) with $IC_{50}$=22 to 29 µM, MGM $GI_{50}$=0.16 to 0.32 µM, Top1 inhibition "+++" are the most potent representatives of the 69-79 series tested for dual Top1-Tdp1 inhibitory activity. These also represent a new chemotype of fully synthetic small-molecule Tdp1 inhibitors.

Surprisingly, the hydroxyl analogues (compound 18-23) were inactive against Tdp1. Despite being similar in ability to form hydrogen bonds, the discrepancy in Tdp1 potency when going from the amino group to the hydroxyl group in this series lends support to the hypothesis that hydrogen bonding may not be a predominant factor that determines Tdp1 inhibitory activity. Moreover, it seems reasonable to consider these amino inhibitors to be protonated at physiological pH, and this positively charged state, which is not possible in the hydroxyl series 18-23, seems to be an important requirement for Tdp1 inhibition. This rationale is in agreement with a previous report that the terminal amino group in this series is important for cellular cytotoxicity, though not absolutely necessary for Top1 inhibition.

One member of this amino series (70, n=3) was subjected to Surface Plasmon Resonance (SPR) assays based on reported procedures in order to gain a more detailed understanding of the Tdp1-inhibitor interaction and to measure the affinity of 70 to Tdp1 (FIG. 12). The binding of the inhibitor to the surface-bound Tdp1 induces an increase in resonance units from the initial baseline until a steady-state phase of this interaction is achieved as depicted by a plateau. The decrease in resonance units corresponds to the dissociation or reversibility of the interaction. This result demonstrates direct binding of 70 to Tdp1. This compound was also evaluated using a Fluorescence Resonance Energy Transfer (FRET) assay and was found to be a competitive inhibitor with $K_i$=3.19 μM (FIG. 13). Steroid 7, which binds Tdp1 directly, is also competitive with the DNA substrate for the Tdp1 active site.

All indenoisoquinoline sulfonates and sulfonamides (compounds 80-123) were inactive against Tdp1 ($IC_{50}$>111 μM). This result was unexpected since extensive studies on steroid 7 clearly emphasized the importance of the sulfonyl ester moiety for Tdp1 inhibition, and our initial modeling (FIG. 3) also suggested a good mimic of the phosphotyrosine linkage by the sulfonate group, which is similar to how steroid 7 resembles this group. As the sulfonate or sulfonamide moiety was attached to the terminal amino group, the activity was completely abolished independently of the linker length (n=2-12). Similarly, sulfonamides 132-136 were also inactive against Tdp1. Although steric clashes between the sulfonate or sulfonamide group with components of the binding pocket might be responsible for this result, this explanation is not satisfactory because even when a short side chain is present such as in compound 80, which bears a relatively small mesylate group on an ethyl linker, the activity drops drastically. In the case of the amino series (compounds 69-79), the ligand-binding site seems to accommodate a long side chain quite well. Therefore, steric clashes could only explain the inactivity of compounds with very long and bulky side chains. A different factor must have been the cause of the significant attenuation of Tdp1 inhibition upon sulfonylation of the amino series even though this was completely different in case of steroid 7. Due to the lack of a crystal structure of Tdp1 in complex with an inhibitor, no firm conclusion can be drawn as to where a ligand binds and how it inhibits Tdp1 activity, and molecular modeling failed to provide an answer to the question of sulfonate and sulfonamide inactivities in the present series.

Among the four bis(indenoisoquinolines) synthesized and tested, only the polyamino bis(indenoisoquinoline) 145 displayed low micromolar Tdp1 inhibition, with an $IC_{50}$=1.5 μM and 1.9 μM against rec. and WCE Tdp1, respectively. Three other bis(indenoisoquinolines) 140-142, which were made because of the initial positive results from the amino series with 10-12 methylene linkers, were inactive. This result provides additional support to the hypothesis that the protonation of the amino groups may give favorable charge-complementary interactions within the Tdp1 binding pocket, thereby conferring Tdp1 inhibition. The polyamino bis(indenoisoquinoline) 145 is currently the most potent dual Top1-Tdp1 inhibitor, displaying Top1 inhibition ("++++") equipotent to campothecin, excellent antiproliferative potency (MGM $GI_{50}$=0.394 μM), and also excellent inhibitory activity against Tdp1 in both human rec. and WCE Tdp1 with $IC_{50}$=1.5 and 1.9 μM, respectively.

A series of bis(indenoisoquinolines) and indenoisoquinolines with amino, sulfonate, and sulfonamide side chains have been synthesized to evaluate the hypothesis that dual Top1-Tdp1 inhibition can be achieved in a single compound. In contrast with the reported importance of the sulfonyl ester moiety to the Tdp1 inhibition, all sulfonates and sulfonamides were inactive, while the free amines at various linker lengths displayed good to excellent inhibition. Among them, two compounds 70 and 71 were potent against both Tdp1 and Top1, representing the first two dual Top1-Tdp1 inhibitors ever reported. Significant insights for future lead optimization were deduced: 1) hypothetical charge-complementary interactions between protonated amino groups within the Tdp1 active site may contribute to high potency, and 2) the hydrophobicity of the polymethylene moiety linking the amino group to the heterocycle may also contribute to activity. The polyamino bis(indenoisoquinoline) 145 is currently the most potent dual Top1-Tdp1 inhibitor. This encouraging result has much significance because: 1) this class of indenoisoquinoline compounds serves as the first evidence that having Top1 and Tdp1 inhibitory activity in one single small molecule is in fact possible; 2) the unique structural features of indenoisoquinolines allow much room for manipulation so the pharmacokinetics (absorption, distribution, and excretion) can be modulated and optimized in ways that are not possible for other types of Tdp1 inhibitors, 3) they represent lead molecules for development of new dual Top1-Tdp1 inhibitory agents, and 4) they provide a set of inhibitory ligands that could possibly be crystallized in complex with Tdp1, which would facilitate the structure-based drug design approach.

Experimental Section

General.

Solvents and reagents were purchased from commercial vendors and were used without any further purification. Melting points were determined using capillary tubes with a Mel-Temp apparatus and were uncorrected. Infrared spectra were obtained using KBr pellets using $CHCl_3$ as the solvent. IR spectra were recorded using a Perkin-Elmer 1600 series or Spectrum One FTIR spectrometer. $^1H$ NMR spectra were recorded at 300 MHz using a Bruker ARX300 spectrometer with a QNP probe. Mass spectral analyses were performed at the Purdue University Campus-Wide Mass Spectrometry Center. ESI-MS studies were performed using a Finnigan-MAT LCQ Classic mass spectrometer. EI/CI-MS studies were performed using a Hewlett-Packard Engine or GCQ FinniganMAT mass spectrometer. APCI-MS studies were carried out using an Agilent 6320 Ion Trap mass spectrometer. Combustion microanalyses were performed at the Purdue University Microanalysis Laboratory using a Perkin-Elmer Series II CHNS/O model 2400 analyzer. All reported values are within 0.4% of the calculated values. Analytical thin layer chromatography was carried out on Baker-flex silica gel IB2-F plates, and compounds were visualized with short wavelength UV light and ninhydrin staining. Silica gel flash chromatography was performed using 230-400 mesh silica gel. HPLC analyses were performed on a Waters 1525 binary HPLC pump/Waters 2487 dual λ absorbance detector system using a 5 μM $C_{18}$ reverse phase column. Purities of biologically important compounds were ≥95%. For purities estimated by HPLC, the major peak accounted for ≥95% of the combined total peak area when monitored by a UV detector at 254 nm. All yields refer to isolated compounds.

Benz[d]indeno[1,2-b]pyran-5,11-dione (11)

Sodium metal (3.678 g, 0.160 mol) was cut into small pieces and added to MeOH (40 mL) to make a 4 M methanolic solution, which was then added to a solution of 2-carboxybenzaldehyde (8) (1.000 g, 6.661 mmol) and phthalide (9)

(0.893 g, 6.661 mmol) in ethyl acetate (20 mL). The mixture was stirred and heated at 70° C. for 16 h to yield an orange solution, which was then concentrated, diluted with H$_2$O (100 mL), acidified with 10% HCl until pH 1, and extracted with EtOAc (50 mL×3). The organic layers were combined and extracted with 1 N NaOH (50 mL×3). The aqueous layers were combined and acidified with concentrated HCl until pH 1 to give a red solution. The acidic mixture was extracted with ethyl acetate (50 mL×3) and washed with brine (50 mL). The organic layers were dried over anhydrous MgSO$_4$, filtered, and concentrated to yield the intermediate 10. The crude intermediate 10 was dissolved in benzene (125 mL), followed by an addition of TsOH.H$_2$O (100 mg). The resulting mixture was heated for 7 h at reflux in a flask affixed with a Dean-Stark trap. The solution was cooled to room temperature, concentrated, diluted with CHCl$_3$ (150 mL), and washed with sat NaHCO$_3$ (50 mL×3) and brine (50 mL). The organic layer was dried over anhydrous Na$_2$SO$_4$, and concentrated to yield the desired product as an orange solid (1.69 g, 93%): mp 254-256° C. (lit. 257° C.). $^1$H NMR (300 MHz, CDCl$_3$) δ 8.39 (d, J=7.8 Hz, 1H), 8.31 (d, J=8.2 Hz, 1H), 7.84 (t, J=7.5 Hz, 1H), 7.61 (d, J=6.9 Hz, 1H), 7.55-7.39 (m, 4H).

General Procedure for the Preparation of n-Hydroxyalkyl Indenoisoquinolines 18-22 n-Aminoalcohols 12-16 (0.50 g) in CHCl$_3$ (10 mL) were added to a solution of lactone 11 (1.0 equiv) in CHCl$_3$ (50 mL). The reaction mixtures were heated at reflux for 3-6 h with stirring, and then washed with H$_2$O (50 mL×2) and brine (50 mL). The organic layers were dried over anhydrous Na$_2$SO$_4$, filtered and concentrated, adsorbed onto SiO$_2$, and purified by flash column chromatography (SiO$_2$), eluting with 5% MeOH in CHCl$_3$, to provide the products 18-22 in high purity.

6-(2-Hydroxyethyl)-5H-indeno[1,2-c]isoquinoline-5,11(6H)-dione (18)

The general procedure provided the desired product as a red solid (1.10 g, 62%): mp 201-204° C. (lit. 200-201° C.). $^1$H NMR (300 MHz, CDCl$_3$) δ 8.68 (d, J=8.1 Hz, 1H), 8.32 (d, J=8.3 Hz, 1H), 7.74 (dt, J=1.2 and 7.1 Hz, 1H), 7.62 (dd, J=1.2 and 7.0 Hz, 2H), 7.48-7.37 (m, 3H), 4.76 (t, J=5.8 Hz, 2H), 4.21 (q, J=5.6 Hz, 2H), 2.60 (m, J=5.3 Hz, 1H); ESI-MS m/z (rel intensity) 292 (MH$^+$, 100); HRMS (+ESI) calcd for MH$^+$: 292.0974. found: 292.0978; HPLC purity: 96.6% (MeOH, 100%), 96.2% (MeOH—H$_2$O, 90:10).

6-(3-Hydroxypropyl)-5H-indeno[1,2-c]isoquinoline-5,11(6H)-dione (19)

The general procedure provided the desired product as a red solid (1.20 g, 98%): mp 173-175° C. (lit. 170-171° C.). $_1$H NMR (300 MHz, CDCl$_3$) δ 8.75 (d, J=8.2 Hz, 1H), 8.38 (d, J=8.1 Hz, 1H), 7.79-7.65 (m, 3H), 7.53-7.41 (m, 3H), 4.76 (t, J=6.4 Hz, 2H), 3.75 (q, J=6.0 Hz, 2H), 3.26 (t, J=6.3 Hz, 1H), 2.20 (m, 2H); ESI-MS m/z (rel intensity) 328 (MNa$^+$, 61); HRMS (+ESI) calcd for MH$^+$: 306.1130. found: 306.1127; HPLC purity: 99.5% (MeOH, 100%), 98.6% (MeOH—H$_2$O, 90:10).

6-(4-Hydroxybutyl)-5H-indeno[1,2-c]isoquinoline-5,11(6H)-dione (20)

The general procedure provided the desired product as a red solid (1.23 g, 95%): mp 165-166° C. (lit. 160-162° C.). $^1$H NMR (300 MHz, CDCl$_3$) δ 8.73 (d, J=8.1 Hz, 1H), 8.36 (d, J=8.3 Hz, 1H), 7.76 (dt, J=1.2 and 8.2 Hz, 1H), 7.65 (dd, J=1.4 and 6.7 Hz, 1H), 7.59 (d, J=7.6 Hz, 1H), 7.50-7.38 (m, 3H), 4.62 (t, J=7.7 Hz, 2H), 3.84 (q, J=6.0 Hz, 2H), 2.07 (m, 2H), 1.86 (m, 2H), 1.70 (t, J=5.3 Hz, 1H); ESI-MS m/z (rel intensity) 320 (MH$^+$, 42); HRMS (+ESI) calcd for MH$^+$: 320.1287. found: 320.1289; HPLC purity: 99.1% (MeOH, 100%), 96.2% (MeOH—H$_2$O, 90:10).

6-(5-Hydroxypentyl)-5H-indeno[1,2-c]isoquinoline-5,11(6H)dione (21)

The general procedure provided the desired product as an orange solid (1.45 g, 90%): mp 144-146° C. (lit. 146-148° C.). $^1$H NMR (300 MHz, CDCl$_3$) δ 8.72 (d, J=8.1 Hz, 1H), 8.35 (d, J=8.4 Hz, 1H), 7.75 (dt, J=1.2 and 7.0 Hz, 1H), 7.65 (dd, J=1.4 and 4.9 Hz, 1H), 7.49-7.38 (m, 4H), 4.56 (t, J=7.7 Hz, 2H), 3.74 (q, J=5.3 Hz, 2H), 1.98 (m, 2H), 1.74-1.60 (m, 4H), 1.42 (t, J=4.8 Hz, 1H); ESI-MS m/z (rel intensity) 334 (MH$^+$, 100); HRMS (+ESI) calcd for MH$^+$: 334.1443. found: 334.1445; HPLC purity: 97.9% (MeOH, 100%), 95.4% (MeOH—H$_2$O, 90:10).

6-(6-Hydroxyhexyl)-5H-indeno[1,2-c]isoquinoline-5,11(6H)-dione (22)

The general procedure provided the desired product as a red solid (1.24 g, 84%): mp 139-141° C. IR (film) 3425, 1765, 1698, 1663, 1611, 1550, 1504, 1427, 1317, 758 cm$^{-1}$; $^1$H NMR (300 MHz, CDCl$_3$) δ 8.72 (d, J=8.1 Hz, 1H), 8.36 (d, J=8.2 Hz, 1H), 7.75 (dt, J=1.3 and 7.4 Hz, 1H), 7.65 (dd, J=1.0 and 7.2 Hz, 1H), 7.50-7.37 (m, 4H), 4.56 (t, J=7.7 Hz, 2H), 3.70 (q, J=5.7 Hz, 2H), 3.50 (d, J=4.9 Hz, 1H), 1.96 (m, 2H), 1.66-1.45 (m, 6H); ESI-MS m/z (rel intensity) 370 (MNa$^+$, 100); HRMS (+ESI) calcd for MNa$^+$: 370.1419. found: 370.1424; HPLC purity: 97.6% (MeOH, 100%), 99.0% (MeOH—H$_2$O, 90:10).

6-(7-Hydroxyheptyl)-5H-indeno[1,2-c]isoquinoline-5,11(6H)-dione (23)

Bromoalcohol 33 (0.975 g, 5.0 mmol) and urotropine (34, 0.771 g, 5.5 mmol) dissolved in CHCl$_3$ (20 mL). The mixture was stirred at reflux for 5 h, and allowed to stand overnight to induce the formation of quaternary salt 35. The salt was filtered and added to a 2 M ethanolic HCl solution (15 mL). The reaction mixture was warmed up gently with a heat gun, and swirled to produce white NH$_4$Cl precipitate, which was removed by filtration. The mother liquor was concentrated in vacuo and diluted in H$_2$O (20 mL), followed by cooling in an ice bath. The solution was made strongly alkaline (pH 13) with 6 M NaOH, extracted with diethyl ether (25 mL×3), and washed with brine (25 mL). The ethereal layers were combined, dried over anhydrous Na$_2$SO$_4$, and concentrated to afford a yellowish oil of crude 17. The crude 17 was dissolved in CHCl$_3$ (20 mL) and added to a solution of lactone 11 (1 equiv of 33) in CHCl$_3$ (50 mL). The reaction mixture was heated at reflux for 18 h, concentrated, adsorbed onto SiO$_2$, and purified by flash column chromatography (SiO$_2$), eluting with EtOAc-hexane in a gradient of concentration ratios from 5:3 to 7:3 to provide the desired product as a fine red powdery solid (0.95 g, 52%): mp 132-135° C. IR (film) 3468, 1776, 1698, 1663, 1611, 1550, 1504, 1427, 1318, 756 cm$^{-1}$; $^1$H NMR (300 MHz, CDCl$_3$) δ 8.72 (d, J=8.0 Hz, 1H), 8.36 (d, J=8.1 Hz, 1H), 7.72 (t, J=7.0 Hz, 1H), 7.65 (d, J=6.4 Hz, 1H), 7.49-7.40 (m, 4H), 4.54 (t, J=7.8 Hz, 2H), 3.67 (d, J=3.4H, 2H), 1.94-1.86 (m, 2H), 1.62-1.43 (m, 8H), 1.30 (m, 1H);

ESI-MS m/z (rel intensity) 362 (MH$^+$, 17); HRMS (+ESI) calcd for MH$^+$: 362.1756. found: 362.1760. Anal. calcd for C$_{23}$H$_{23}$NO$_3$.0.2H$_2$O: C, 75.68; H, 6.46; N, 3.84. Found: C, 75.51; H, 6.32; N, 3.62.

General Procedure for the Preparation of Indenoisoquinoline Sulfonates 25-29 and Chloride 30

A solution of Et$_3$N (2 equiv) in CH$_2$Cl$_2$ (1 mL) and DMAP (0.2 equiv) was added to solutions of the n-alkylhydroxy indenoisoquinolines 19-23 (100 mg) in CH$_2$Cl$_2$ (10 mL). The solutions were stirred at room temperature for 5 min, and tosyl chloride (2 equiv) was added. The reaction mixtures were stirred at room temperature for 16 h, quenched with aq 3 M HCl (50 mL), and washed with H$_2$O (50 mL), sat. NaHCO$_3$ (50 mL) and brine (50 mL). The organic layers were dried over anhydrous Na$_2$SO$_4$, filtered and concentrated, purified by flash column chromatography (SiO$_2$), eluting with EtOAc (3-5%) in CHCl$_3$, to provide the indenoisoquinoline sulfonates 25-29 in high purity after trituration with diethyl ether (20 mL).

3-(5,11-Dioxo-5H-indeno[1,2-c]isoquinolin-6(11H)-yl)propyl-4-methyl-benzenesulfonate (25)

The general procedure provided the desired product as a red solid (132.5 mg, 88%): mp 177-179° C. (lit. 180-182° C.). $^1$H NMR (300 MHz, CDCl$_3$) δ 8.72 (d, J=8.1 Hz, 1H), 8.31 (d, J=7.5 Hz, 1H), 7.83 (d, J=8.3 Hz, 2H), 7.73-7.63 (m, 3H), 7.49-7.34 (m, 5H), 4.62 (t, J=7.9 Hz, 2H), 4.31 (t, J=5.7 Hz, 2H), 2.46 (s, 3H), 2.34 (m, 2H); ESI-MS m/z (rel intensity) 482 (MNa$^+$, 100); HRMS (+ESI) calcd for MNa$^+$: 482.1038. found: 482.1041; HPLC purity: 98.6% (MeOH, 100%), 99.4% (MeOH—H$_2$O, 90:10).

4-(5,11-Dioxo-5H-indeno[1,2-c]isoquinolin-6(11H)-yl)butyl-4-methyl-benzenesulfonate (26)

The general procedure provided the desired product as an orange solid (129 mg, 87%): mp 160-163° C. IR (film) 1757, 1695, 1667, 1612, 1550, 1504, 1428, 1348, 1174, 753 cm$^{-1}$; $^1$H NMR (300 MHz, CDCl$_3$) δ 8.72 (d, J=8.0 Hz, 1H), 8.32 (d, J=7.4 Hz, 1H), 7.78-7.70 (m, 3H), 7.66 (d, J=7.0 Hz, 1H), 7.50-7.42 (m, 4H), 7.33 (d, J=8.2 Hz, 2H), 4.55 (t, J=6.8 Hz, 2H), 4.16 (t, J=5.9 Hz, 2H), 2.42 (s, 3H), 1.98-1.88 (m, 4H); ESIMS m/z (rel intensity) 496 (MNa$^+$, 100); HRMS (+ESI) calcd for MNa$^+$: 496.1195. found: 496.1201; HPLC purity: 98.4% (MeOH, 100%), 99.2% (MeOH—H$_2$O, 90:10).

5-(5,11-Dioxo-5H-indeno[1,2-c]isoquinolin-6(11H)-yl)pentyl-4-methyl-benzenesulfonate (27)

The general procedure provided the desired product as an orange solid (119 mg, 81%): mp 163-165° C. IR (film) 1697, 1661, 1609, 1549, 1503, 1427, 1355, 1174, 755 cm$^{-1}$; $^1$H NMR (300 MHz, CDCl$_3$) δ 8.73 (d, J=8.1 Hz, 1H), 8.34 (d, J=7.8 Hz, 1H), 7.79-7.70 (m, 3H), 7.66 (d, J=6.8 Hz, 1H), 7.50-7.39 (m, 4H), 7.34 (d, J=8.1 Hz, 2H), 4.51 (t, J=7.8 Hz, 2H), 4.09 (t, J=6.1 Hz, 2H), 2.43 (s, 3H), 1.91-1.75 (m, 4H), 1.65-1.57 (m, 2H); ESI-MS m/z (rel intensity) 488 (MH$^+$, 100); HRMS (+ESI) calcd for MH$^+$: 488.1532. found: 488.1539; HPLC purity: 97.1% (MeOH, 100%), 98.0% (MeOH—H$_2$O, 90:10).

6-(5,11-Dioxo-5H-indeno[1,2-c]isoquinolin-6(11H)-yl)hexyl-4-methyl-benzenesulfonate (28)

The general procedure provided the desired product as an orange solid (123 mg, 85%): mp 146-149° C. IR (film) 1767, 1693, 1662, 1610, 1550, 1503, 1428, 1357, 1176, 757 cm$^{-1}$; $^1$H NMR (300 MHz, CDCl$_3$) δ 8.72 (d, J=8.2 Hz, 1H), 8.34 (d, J=7.9 Hz, 1H), 7.80-7.70 (m, 3H), 7.65 (d, J=6.8 Hz, 1H), 7.49-7.38 (m, 4H), 7.36 (d, J=8.0 Hz, 2H), 4.51 (t, J=7.6 Hz, 2H), 4.07 (t, J=6.3 Hz, 2H), 2.44 (s, 3H), 1.88 (m, 2H), 1.73 (m, 2H), 1.57 (m, 4H); ESI-MS m/z (rel intensity) 502 (MH$^+$, 100); HRMS (+ESI) calcd for MH$^+$: 502.1688. found: 502.1694; HPLC purity: 98.0% (MeOH, 100%), 96.8% (MeOH—H$_2$O, 90:10).

7-(5,11-Dioxo-5H-indeno[1,2-c]isoquinolin-6(11H)-yl)heptyl-4-methyl-benzenesulfonate (29)

The general procedure provided the desired product as a red solid (109 mg, 76%): mp 123-126° C. IR (film) 1775, 1698, 1664, 1611, 1550, 1504, 1428, 1358, 1176, 758 cm$^{-1}$; $^1$H NMR (300 MHz, CDCl$_3$) δ 8.72 (d, J=8.0 Hz, 1H), 8.35 (d, J=7.6 Hz, 1H), 7.80-7.70 (m, 3H), 7.65 (d, J=6.8 Hz, 1H), 7.49-7.39 (m, 4H), 7.35 (d, J=8.1 Hz, 2H), 4.51 (t, J=7.7 Hz, 2H), 4.05 (t, J=6.3 Hz, 2H), 2.44 (s, 3H), 1.90 (m, 2H), 1.67 (m, 2H), 1.49 (m, 2H), 1.40-1.37 (m, 4H); ESI-MS m/z (rel intensity) 516 (MH$^+$, 100); HRMS (+ESI) calcd for MH$^+$: 516.1845. found: 516.1848; HPLC purity: 95.4% (MeOH, 100%), 98.3% (MeOH—H$_2$O, 90:10).

6-(2-Chloroethyl)-5H-indeno[1,2-c]isoquinoline-5,11(6H)-dione (30)

The general procedure provided the chloride product as a purple solid (105 mg, 99%): mp 210-212° C. (lit. 197-199° C.). $^1$H NMR (300 MHz, CDCl$_3$) δ 8.73 (d, J=8.0 Hz, 1H), 8.36 (d, J=8.2 Hz, 1H), 7.78 (dt, J=1.2 and 8.1 Hz, 1H), 7.67 (d, J=6.8 Hz, 1H), 7.59 (d, J=7.4 Hz, 1H), 7.52-7.42 (m, 3H), 4.86 (t, J=7.4 Hz, 2H), 3.97 (t, J=7.7 Hz, 2H); probe-EI/CI-MS m/z (rel intensity) 309 (M$^+$, 33); HRMS (+EI/CI) calcd for M$^+$: 309.0557. found: 309.0560; HPLC purity: 95.3% (MeOH, 100%), 97.3% (MeOH—H$_2$O, 90:10).

2-(5,11-Dioxo-5H-indeno[1,2-c]isoquinolin6(11H)-yl)ethyl Acetate (31)

Et$_3$N (34.7 mg, 0.343 mmol), CH$_3$COOAg (57.2 mg, 0.343 mmol), and TsCl (65.4 mg, 0.343 mmol) were added to the solution of 18 (50 mg, 0.172 mmol) in CH$_2$Cl$_2$ (50 mL). The reaction mixture was stirred at room temperature for 16 h, and then washed with sat. NaHCO$_3$ (50 mL) and brine (50 mL). The organic layer was dried over Na$_2$SO$_4$, filtered and concentrated, adsorbed onto SiO$_2$, and purified by flash column chromatography (SiO$_2$), eluting with EtOAc—CHCl$_3$ (2:8) to afford the desired product as a red solid (38.5 mg, 67%): mp 221-224° C. IR (film) 1738, 1693, 1655, and 1506 cm$^{-1}$; $^1$H NMR (300 MHz, CDCl$_3$) δ 8.75 (d, J=8.0 Hz, 1H), 8.37 (d, J=7.9 Hz, 1H), 7.75 (t, J=5.8 Hz, 2H), 7.67 (dd, J=1.1 and 5.8 Hz, 1H), 7.51-7.41 (m, 3H), 4.84 (t, J=6.2 Hz, 2H), 4.57 (t, J=6.1 Hz, 2H), 1.94 (s, 3H); probe-EI/CI-MS m/z (rel intensity) 334 (MH$^+$, 100); HRMS (+EI/CI) calcd for M$^+$: 333.1001. found: 333.1005; HPLC purity: 97.3% (MeOH, 100%), 98.0% (MeOH—H$_2$O, 90:10).

Compounds 47-79 were synthesized based on the procedures reported by Morrell at al. Purities of biologically tested indenoisoquinoline amine hydrochlorides 69-79 were ≥95% by HPLC.

TABLE 2

Purities of Indenoisoquinoline Amine Hydrochlorides 69-79 by HPLC

| Comp. | Purity by HPLC | |
|---|---|---|
| | MeOH, 100% | MeOH—H$_2$O, 90:10 |
| 69 | 97.8 | 97.6 |
| 70 | 96.7 | 98.0 |
| 71 | 98.5 | 100 |
| 72 | 98.3 | 100 |
| 73 | 98.1 | 97.8 |
| 74 | 95.7 | 100 |
| 75 | 96.9 | 98.5 |
| 76 | 95.5 | 95.8 |
| 77 | 99.4 | 98.8 |
| 78 | 98.7 | 96.6 |
| 79 | 99.2 | 98.5 |

General Procedure for the Preparation of Indenoisoquinoline Sulfonamides 80-123

Indenoisoquinoline salts 69-79 (50 mg, 0.107-0.153 mmol) were dissolved in CHCl$_3$ (15 mL), followed by the addition of Et$_3$N (2 equiv) in CHCl$_3$ (1 mL). The solutions were stirred at room temperature for 5 min. Mesyl, benzenesulfonyl, tosyl, or p-bromobenzenesulfonyl chloride (2 equiv) were then added. The mixtures were heated at reflux for 16 h, and then washed with sat. NaHCO$_3$ (50 mL) and brine (50 mL). The organic layers were dried over anhydrous Na$_2$SO$_4$, filtered and concentrated, and purified by flash column chromatography (SiO$_2$), eluting with EtOAc—CHCl$_3$ to provide the indenoisoquinoline sulfonamide products in high purity.

N-(2-(5,11-Dioxo-5H-indeno[1,2-c]isoquinolin-6 (11H)ethyl)-methanesulfonamide (80)

The crude product was eluted with EtOAc—CHCl$_3$ (4:6) to afford the desired product as an orange solid (38.7 mg, 69%): mp 250-255° C. IR (film) 3313, 1705, 1653, 1609, 1549, 1502, 1418, 1321, 1129, 758 cm$^{-1}$; $^1$H NMR (300 MHz, DMSO-d$_6$) δ 8.59 (d, J=8.0 Hz, 1H), 8.23 (d, J=8.0 Hz, 1H), 7.89-7.82 (m, 2H), 7.58-7.47 (m, 5H), 4.61 (t, J=6.7 Hz, 2H), 3.42 (m, 2H), 2.91 (s, 3H); probe-EI/CI-MS m/z (rel intensity) 369 (M$^+$, 100); HRMS (EI/CI) calcd for M$^+$: 368.0831. found: 368.0835; HPLC purity: 96.0% (MeOH, 100%), 96.3% (MeOH—H$_2$O, 90:10).

N-(3-(5,11-Dioxo-5H-indeno[1,2-c]isoquinolin-6 (11H)propyl)-methanesulfonamide (81)

The crude product was eluted with EtOAc—CHCl$_3$ (6:4) to afford the desired product as an orange solid (47.1 mg, 84%): mp 201-203° C. IR (film) 3203, 1696, 1646, 1610, 1549, 1504, 1428, 1317, 1137, 757 cm$^{-1}$; $^1$H NMR (300 MHz, CDCl$_3$) δ 8.72 (d, J=8.1 Hz, 1H), 8.32 (d, J=8.1 Hz, 1H), 7.77 (t, J=7.0 Hz, 1H), 7.65 (d, J=6.5 Hz, 1H), 7.55-7.38 (m, 4H), 5.73 (t, J=6.8 Hz, 1H), 4.70 (t, J=6.0 Hz, 2H), 3.25 (q, J=6.5 Hz, 2H), 3.00 (s, 3H), 2.23-2.23 (m, 2H); APCI-MS m/z (rel intensity) 383 (MH$^+$, 100); HRMS (+ESI) calcd for MH$^+$: 383.1066. found: 383.1069; HPLC purity: 99.1% (MeOH, 100%), 96.7% (MeOH—H$_2$O, 90:10).

N-(4-(5,11-Dioxo-5H-indeno[1,2-c]isoquinolin-6 (11H)butyl)-methanesulfonamide (82)

The crude product was eluted with EtOAc—CHCl$_3$ (7:3) to afford the desired product as an orange solid (42.2 mg, 81%): mp 193-194° C. IR (film) 3272, 2346, 1694, 1655, 1611, 1549, 1504, 1318, 1152, 756 cm$^{-1}$; $^1$H NMR (300 MHz, CDCl$_3$) δ 8.72 (d, J=7.8 Hz, 1H), 8.34 (d, J=8.3 Hz, 1H), 7.74 (t, J=6.8 Hz, 1H), 7.66 (d, J=6.9 Hz, 1H), 7.50-7.40 (m, 4H), 4.60 (m, 3H), 3.34 (q, J=6.6 Hz, 2H), 3.00 (s, 3H), 2.05 (m, 2H), 1.85 (m, 2H); ESI-MS m/z (rel intensity) 397 (MH$^+$, 100); HRMS (+ESI) calcd for MH$^+$: 397.1222. found: 397.1231; HPLC purity: 98.4% (MeOH, 100%), 97.2% (MeOH—H$_2$O, 90:10).

N-(5-(5,11-Dioxo-5H-indeno[1,2-c]isoquinolin-6 (11H)pentyl)-methanesulfonamide (83)

The crude product was eluted with EtOAc—CHCl$_3$ (6:4) to afford the desired product as an orange solid (44.0 mg, 79%): mp 150-152° C. IR (film) 3275, 1698, 1660, 1611, 1550, 1504, 1318, 1150, 756 cm$^{-1}$; $^1$H NMR (300 MHz, CDCl$_3$) δ 8.72 (d, J=8.0 Hz, 1H), 8.34 (d, J=8.0 Hz, 1H), 7.76 (td, J=7.1 and 1.1 Hz, 1H), 7.65 (d, J=6.9 Hz, 1H), 7.50-7.41 (m, 4H), 4.57 (t, J=7.4 Hz, 2H), 4.48 (t, J=5.9 Hz, 1H), 3.24 (q, J=6.4 Hz, 2H), 2.97 (s, 3H), 2.00 (m, 2H), 1.76 (m, 2H), 1.65 (m, 2H); ESI-MS m/z (rel intensity) 411 (MH$^+$, 100); HRMS (+ESI) calcd for MH$^+$: 411.1379. found: 411.1381; HPLC purity: 99.7% (MeOH, 100%), 98.5% (MeOH—H$_2$O, 90:10).

N-(6-(5,11-Dioxo-5H-indeno[1,2-c]isoquinolin-6 (11H)hexyl)-methanesulfonamide (84)

The crude product was eluted with EtOAc—CHCl$_3$ (5:5) to afford the desired product as an orange solid (42.7 mg, 77%): mp 160-161° C. IR (film) 3355, 1697, 1646, 1608, 1548, 1504, 1452, 1364, 1258, 764 cm$^{-1}$; $^1$H NMR (300 MHz, CDCl$_3$) δ 8.72 (d, J=8.2 Hz, 1H), 8.36 (d, J=7.6 Hz, 1H), 7.76 (dd, J=7.0 and 1.2 Hz, 1H), 7.65 (d, J=6.8 Hz, 1H), 7.50-7.41 (m, 4H), 4.56 (t, J=7.6 Hz, 1H), 4.44 (m, 1H), 3.20 (q, J=6.5 Hz, 2H), 2.97 (s, 3H), 1.93 (m, 2H), 1.67 (m, 2H), 1.54 (m, 4H); ESI-MS m/z (rel intensity) 425 (MH$^+$, 100); HRMS (+ESI) calcd for MH$^+$: 425.1538. found: 425.1532; HPLC purity: 99.8% (MeOH, 100%), 98.3% (MeOH—H$_2$O, 90:10).

N-(7-(5,11-Dioxo-5H-indeno[1,2-c]isoquinolin-6 (11H)heptyl)-methanesulfonamide (85)

The crude product was eluted with EtOAc—CHCl$_3$ (6:4) to afford the desired product as an orange solid (33 mg, 60%): mp 159-162° C. IR (film) 3227, 1687, 1646, 1609, 1547, 1505, 1429, 1308, 1144, 754 cm$^{-1}$; $^1$H NMR (300 MHz, CDCl$_3$) δ 8.72 (d, J=8.1 Hz, 1H), 8.36 (d, J=8.2 Hz, 1H), 7.73 (dd, J=1.3 and 6.9 Hz, 1H), 7.65 (d, J=6.7 Hz, 1H), 7.50-7.39 (m, 4H), 4.54 (t, J=7.8 Hz, 2H), 4.24 (m, 1H), 3.19 (q, J=6.8 Hz, 2H), 2.97 (s, 3H), 1.91 (m, 2H), 1.63-1.43 (m, 8H); ESI-MS m/z (rel intensity) 461 (MNa$^+$, 100); HRMS (+ESI) calcd for MNa$^+$: 461.1511. found: 461.1518. Anal. calcd for C$_{24}$H$_{26}$N$_2$O$_4$S.0.75H$_2$O: C, 63.77; H, 6.13; N, 6.20. Found: C, 63.73; H, 6.06; N, 5.86.

N-(8-(5,11-Dioxo-5H-indeno[1,2-c]isoquinolin-6 (11H)octyl)-methanesulfonamide (86)

The crude product was eluted with EtOAc—CHCl$_3$ (6:4) to afford the desired product as an orange solid (41.3 mg, 75%): mp 151-155° C. IR (film) 3214, 1767, 1699, 1645, 1612, 1551, 1504, 1426, 1315, 1142, 760 cm$^{-1}$; $^1$H NMR (300 MHz, CDCl$_3$) δ 8.73 (d, J=8.0 Hz, 1H), 8.36 (d, J=8.0 Hz, 1H), 7.75 (t, J=7.1 Hz, 1H), 7.66 (d, J=6.8 Hz, 1H), 7.50-7.39

(m, 4H), 4.54 (t, J=8.2 Hz, 2H), 4.24 (m, 1H), 3.17 (q, J=6.9 Hz, 2H), 2.96 (s, 3H), 1.90 (m, 2H), 1.57-1.26 (m, 10H); ESI-MS m/z (rel intensity) 453 (MH$^+$, 100); HRMS (+ESI) calcd for MH$^+$: 453.1848. found: 453.1853. Anal. calcd for $C_{25}H_{28}N_2O_4S$: C, 66.35; H, 6.24; N, 6.19. Found: C, 66.34; H, 6.31; N, 5.81.

N-(9-(5,11-Dioxo-5H-indeno[1,2-c]isoquinolin-6 (11H)-yl)nonyl)-methanesulfonamide (87)

The crude product was eluted with EtOAc—CHCl$_3$ (5:5) to afford the desired product as an orange solid (54.2 mg, 82%): mp 154-156° C. IR (film) 3211, 1700, 1645, 1550, 1506, 1426, 1314, 1142, 759 cm$^{-1}$; $^1$H NMR (300 MHz, CDCl$_3$) δ 8.73 (d, J=8.1 Hz, 1H), 8.36 (d, J=7.7 Hz, 1H), 7.73 (t, J=8.2 Hz, 1H), 7.66 (d, J=6.2 Hz, 1H), 7.50-7.40 (m, 4H), 4.54 (t, J=8.0 Hz, 2H), 4.21 (m, 1H), 3.17 (q, J=6.9 Hz, 2H), 2.96 (s, 3H), 1.90 (m, 2H), 1.63-1.23 (m, 12H); ESI-MS m/z (rel intensity) 467 (MH$^+$, 50); HRMS (+ESI) calcd for MH$^+$: 467.2005. found: 467.2007. Anal. calcd for $C_{26}H_{30}N_2O_4S.0.2H_2O$: C, 66.41; H, 6.52; N, 5.96. Found: C, 66.18; H, 6.39; N, 5.70.

N-(10-(5,11-Dioxo-5H-indeno[1,2-c]isoquinolin-6 (11H)decyl)-methanesulfonamide (88)

The crude product was eluted with EtOAc—CHCl$_3$ (3:7) to afford the desired product as an orange solid (45.3 mg, 83%): mp 115-117° C. IR (film) 3297, 1697, 1663, 1611, 1551, 1505, 1428, 1351, 1175, 759 cm$^{-1}$; $^1$H NMR (300 MHz, CDCl$_3$) δ 8.72 (d, J=8.1 Hz, 1H), 8.35 (d, J=7.5 Hz, 1H), 7.72 (t, J=6.9 Hz, 1H), 7.65 (d, J=6.3 Hz, 1H), 7.49-7.40 (m, 4H), 4.53 (t, J=7.9 Hz, 2H), 4.20 (br s, 1H), 3.16 (q, J=6.8 Hz, 2H), 2.95 (s, 3H), 1.93 (m, 2H), 1.56-1.18 (m, 14H); ESI-MS m/z (rel intensity) 481 (MH$^+$, 100); HRMS (+ESI) calcd for MH$^+$: 481.2161. found: 481.2165; HPLC purity: 95.7% (MeOH, 100%), 96.2% (MeOH—H$_2$O, 90:10).

N-(11-(5,11-Dioxo-5H-indeno[1,2-c]isoquinolin-6 (11H)-yl)undecyl)-methanesulfonamide (89)

The crude product was eluted with EtOAc—CHCl$_3$ (5:5) to afford the desired product as an orange solid (48.7 mg, 89%): mp 136-137° C. IR (film) 3299, 1699, 1658, 1612, 1577, 1504, 1424, 1312, 1134, 761 cm$^{-1}$; $^1$H-NMR (300 MHz, CDCl$_3$) δ 8.72 (d, J=8.2 Hz, 1H), 8.35 (d, J=8.1 Hz, 1H), 7.75 (t, J=7.3 Hz, 1H), 7.65 (d, J=6.3 Hz, 1H), 7.49-7.40 (m, 4H), 4.53 (t, J=7.8 Hz, 2H), 4.25 (br s, 1H), 3.16 (q, J=6.6 Hz, 2H), 2.96 (s, 3H), 1.90 (m, 2H), 1.61-1.25 (m, 16H); ESI-MS m/z (rel intensity) 495 (MH$^+$, 100); HRMS (+ESI) calcd for MH$^+$: 495.2318. found: 495.2322; HPLC purity: 97.4% (MeOH, 100%), 100% (MeOH—H$_2$O, 90:10).

N-(12-(5,11-Dioxo-5H-indeno[1,2-c]isoquinolin-6 (11H)-yl)dodecyl)-methanesulfonamide (90)

The crude product was eluted with EtOAc—CHCl$_3$ (5:5) to afford the desired product as an orange solid (58.0 mg, 89%): mp 113-117° C. IR (film) 3268, 1698, 1662, 1610, 1550, 1504, 1427, 1318, 1151, 759 cm$^{-1}$; $^1$H NMR (300 MHz, CDCl$_3$) δ 8.71 (d, J=8.0 Hz, 1H), 8.35 (d, J=8.0 Hz, 1H), 7.74 (t, J=7.7 Hz, 1H), 7.64 (d, J=6.5 Hz, 1H), 7.49-7.40 (m, 4H), 4.52 (t, J=7.7 Hz, 2H), 4.26 (m, 1H), 3.16 (dd, J=13 and 6.7 Hz, 2H), 2.95 (s, 3H), 1.89 (m, 14H); APCI-MS m/z (rel intensity) 509 (MH$^+$, 100); HRMS (+ESI) calcd for MNa$^+$: 531.2294. found: 531.2291; HPLC purity: 99.2% (CH$_3$CN, 100%), 98.3% (CH$_3$CN—H$_2$O, 90:10).

N-(2-(5,11-Dioxo-5H-indeno[1,2-c]isoquinolin-6 (11H)ethyl)-benzenesulfonamide (91)

The crude product was eluted with EtOAc—CHCl$_3$ (2:8) to afford the desired product as an orange solid (47.8 mg, 72%): mp 246-249° C. IR (film) 3233, 1702, 1652, 1610, 1551, 1505, 1425, 1342, 1157, 756 cm$^{-1}$; $^1$H NMR (300 MHz, DMSO-d$_6$) δ 8.54 (d, J=8.1 Hz, 1H), 8.18-8.13 (m, 2H), 7.80-7.72 (m, 4H), 7.58-7.48 (m, 7H), 4.55 (t, J=6.9 Hz, 2H), 3.23 (t, J=6.8 Hz, 2H); ESI-MS m/z (rel intensity) 431 (MH$^+$, 13); HRMS (+ESI) calcd for MH$^+$: 431.1066. found: 431.1073; HPLC purity: 95.9% (MeOH, 100%), 98.0% (MeOH—H$_2$O, 90:10).

N-(3-(5,11-Dioxo-5H-indeno[1,2-c]isoquinolin-6 (11H)-yl)propyl)-benzenesulfonamide (92)

The crude product was eluted with EtOAc—CHCl$_3$ (2:8) to afford the desired product as a red solid (57.2 mg, 88%): mp 216-218° C. IR (film) 3282, 1655, 1611, 1550, 1502, 1446, 1317, 1161, 748 cm$^{-1}$; $^1$H NMR (300 MHz, CDCl$_3$) δ 8.72 (d, J=8.0 Hz, 1H), 8.31 (d, J=8.1 Hz, 1H), 7.90-7.88 (m, 2H), 7.78 (d, J=8.3 Hz, 1H), 7.65 (d, J=5.9 Hz, 1H), 7.51-7.38 (m, 7H), 5.96 (t, J=5.0 Hz, 1H), 4.67 (t, J=6.2 Hz, 2H), 3.01 (q, J=4.8 Hz, 2H), 2.15 (m, 2H); APCI-MS m/z (rel intensity) 445 (MH$^+$, 100); HRMS (+ESI) calcd for MNa$^+$: 467.1042. found: 467.1047; HPLC purity: 95.8% (MeOH, 100%), 95.1% (MeOH—H$_2$O, 95:5).

N-(4-(5,11-Dioxo-5H-indeno[1,2-c]isoquinolin-6 (11H)-yl)butyl)-benzenesulfonamide (93)

The crude product was eluted with EtOAc—CHCl$_3$ (3:7) to afford the desired product as a red solid (57.2 mg, 89%): mp 184-186° C. IR (film) 3222, 1700, 1652, 1614, 1551, 1507, 1427, 1324, 1164, 753 cm$^{-1}$; $^1$H NMR (300 MHz, CDCl$_3$) δ 8.71 (d, J=8.0 Hz, 1H), 8.32 (d, J=8.0 Hz, 1H), 7.89 (d, J=6.9 Hz, 2H), 7.75 (t, J=7.1 Hz, 1H), 7.65 (d, J=7.1 Hz, 1H), 7.56-7.39 (m, 7H), 4.83 (t, J=6.2 Hz, 1H), 4.54 (t, J=7.5 Hz, 2H), 3.14 (q, J=6.5 Hz, 2H), 1.98 (m, 2H), 1.78 (m, 2H); ESI-MS m/z (rel intensity) 459 (MH$^+$, 100); HRMS (+ESI) calcd for MH$^+$: 459.1379. found: 459.1375; HPLC purity: 98.5% (MeOH, 100%), 98.3% (MeOH—H$_2$O, 90:10).

N-(5-(5,11-Dioxo-5H-indeno[1,2-c]isoquinolin-6 (11H)-yl)pentyl)-benzenesulfonamide (94)

The crude product was eluted with EtOAc—CHCl$_3$ (2:8) to afford the desired product as an orange solid (55.8 mg, 84%): mp 194-195° C. IR (film) 3284, 1728, 1699, 1662, 1609, 1548, 1504, 1446, 1326, 1261, 1161, 758 cm$^{-1}$; $^1$H NMR (300 MHz, CDCl$_3$) δ 8.72 (d, J=8.1 Hz, 1H), 8.36 (d, J=8.4 Hz, 1H), 7.87 (dd, J=1.5 and 5.4 Hz, 2H), 7.76 (td, J=1.3 and 7.0 Hz, 1H), 7.65 (d, J=6.8 Hz, 1H), 7.57-7.38 (m, 7H), 4.66 (t, J=6.1 Hz, 1H), 4.52 (t, J=7.5 Hz, 2H), 3.05 (q, J=6.3 Hz, 2H), 1.91 (m, 2H), 1.67 (m, 2H), 1.58 (m, 2H); ESI-MS m/z (rel intensity) 473 (MH$^+$, 100); HRMS (+ESI) calcd for MH$^+$: 473.1535. found: 473.1532; HPLC purity: 99.5% (MeOH, 100%), 98.7% (MeOH—H$_2$O, 90:10).

N-(6-(5,11-Dioxo-5H-indeno[1,2-c]isoquinolin-6 (11H)-yl)hexyl)-benzenesulfonamide (95)

The crude product was eluted with EtOAc—CHCl$_3$ (2:8) to afford the desired product as an orange solid (57.8 mg, 91%):

mp 150-152° C. IR (film) 3272, 1698, 1663, 1503, 1427, 1320, 1159, 756 cm$^{-1}$; $^1$H NMR (300 MHz, CDCl$_3$) δ 8.73 (d, J=8.1 Hz, 1H), 8.35 (d, J=7.6 Hz, 1H), 7.89 (dd, J=6.7 and 1.6 Hz, 2H), 7.76 (t, J=8.2 Hz, 1H), 7.66 (d, J=6.9 Hz, 1H), 7.58-7.41 (m, 7H), 4.56-4.48 (m, 3H), 3.03 (q, J=6.3 Hz, 2H), 1.88 (m, 2H), 1.56-1.48 (m, 6H); ESI-MS m/z (rel intensity) 509 (MNa$^+$, 100); HRMS (+ESI) calcd for MNa$^+$: 509.1511. found: 509.1521; HPLC purity: 97.9% (MeOH, 100%), 97.4% (MeOH—H$_2$O, 90:10).

N-(7-(5,11-Dioxo-5H-indeno[1,2-c]isoquinolin-6 (11H)-yl)heptyl)-benzenesulfonamide (96)

The crude product was eluted with EtOAc—CHCl$_3$ (2:8) to afford the desired compound as an orange product (37.8 mg, 75%): mp 178-181° C. IR (film) 3281, 1698, 1669, 1608, 1548, 1504, 1446, 1324, 1160, 759 cm$^{-1}$; $^1$H NMR (300 MHz, CDCl$_3$) δ 8.73 (d, J=8.1 Hz, 1H), 8.37 (d, J=8.0 Hz, 1H), 7.88 (dd, J=0.92 and 6.8 Hz, 2H), 7.66 (t, J=6.7 Hz, 1H), 7.57 (d, J=6.9 Hz, 1H), 7.54-7.43 (m, 7H), 4.52 (t, J=6.8 Hz, 3H), 3.01 (q, J=6.6 Hz, 2H), 1.87 (m, 2H), 1.49-1.25 (m, 8H); ESI-MS m/z (rel intensity) 501 (MH$^+$, 45); HRMS (+ESI) calcd for MNa$^+$: 523.1668. found: 523.1672. Anal. calcd for C$_{29}$H$_{28}$N$_2$O$_4$S.0.7H$_2$O: C, 67.87; H, 5.77; N, 5.46. Found: C, 67.50; H, 5.40; N, 5.37.

N-(8-(5,11-Dioxo-5H-indeno[1,2-c]isoquinolin-6 (11H)-yl)octyl)-benzenesulfonamide (97)

The crude product was eluted with EtOAc—CHCl$_3$ (2:8) to afford the desired compound as an orange product (36.1 mg, 72%): mp 136-140° C. IR (film) 3271, 1698, 1663, 1504, 1427, 1320, 1159, 756 cm$^{-1}$; $^1$H NMR (300 MHz, CDCl$_3$) δ 8.73 (d, J=8.1 Hz, 1H), 8.36 (d, J=8.0 Hz, 1H), 7.88 (d, J=6.9 Hz, 2H), 7.70 (t, J=7.0 Hz, 1H), 7.66 (d, J=6.7 Hz, 1H), 7.61-7.38 (m, 7H), 4.52 (t, J=7.8 Hz, 2H), 4.36 (m, 1H), 3.00 (q, J=6.8 Hz, 2H), 1.91 (m, 2H), 1.47-1.25 (m, 10H); ESI-MS m/z (rel intensity) 1051 (M$_2$Na$^+$, 100); HRMS (+ESI) calcd for MH$^+$: 515.2005. found: 515.2014; HPLC purity: 99.4% (MeOH, 100%), 99.3% (MeOH—H$_2$O, 90:10).

N-(9-(5,11-Dioxo-5H-indeno[1,2-c]isoquinolin-6 (11H)-yl)nonyl)-benzenesulfonamide (98)

The crude product was eluted with EtOAc—CHCl$_3$ (6:4) to afford the desired compound as an orange solid (58.2 mg, 78%): mp 162-164° C. $^1$H NMR (300 MHz, CDCl$_3$) δ 8.73 (d, J=7.9 Hz, 1H), 8.36 (d, J=8.4 Hz, 1H), 7.87 (d, J=7.0 Hz, 2H), 7.84-7.43 (m, 9H), 4.53 (t, J=8.1 Hz, 2H), 4.38 (m, 1H), 2.99 (q, J=6.9 Hz, 2H), 1.89 (m, 2H), 1.57-1.25 (m, 12H); ESI-MS m/z (rel intensity) 551 (MNa$^+$, 100); HRMS (+ESI) calcd for MH$^+$: 529.2161. found: 529.2159; HPLC purity: 100% (MeOH, 100%), 96.0% (MeOH—H$_2$O, 90:10).

N-(10-(5,11-Dioxo-5H-indeno[1,2-c]isoquinolin-6 (11H)-yl)decyl)-benzenesulfonamide (99)

The crude product was eluted with EtOAc—CHCl$_3$ (15:85) to afford the desired product as an orange solid (54.6 mg, 88%): mp 128-130° C. IR (film) 3274, 1698, 1667, 1611, 1550, 1505, 1428, 1320, 1160, 757 cm$^{-1}$; $^1$H NMR (300 MHz, CDCl$_3$) δ 8.72 (d, J=8.1 Hz, 1H), 8.36 (d, J=8.2 Hz, 1H), 7.88 (dd, J=1.5 and 5.3 Hz, 2H), 7.73 (dt, J=1.3 and 7.0 Hz, 1H), 7.66 (d, J=6.2 Hz, 1H), 7.57-7.40 (m, 7H), 4.53 (t, J=7.6 Hz, 2H), 4.37 (t, J=6.1 Hz, 1H), 2.99 (q, J=6.7 Hz, 2H), 1.90 (m, 2H), 1.52-1.24 (m, 14H); APCI-MS m/z (rel intensity) 543 (MH$^+$, 100); HRMS (+APCI) calcd for MNa$^+$: 565.2137. found: 565.2142; HPLC purity: 100% (MeOH, 100%), 99.4% (MeOH—H$_2$O, 90:10).

N-(11-(5,11-Dioxo-5H-indeno[1,2-c]isoquinolin-6 (11H)-yl)undecyl)-benzenesulfonamide (100)

The crude product was eluted with EtOAc—CHCl$_3$ (6:4) to afford the desired compound as a red solid (53.4 mg, 87%): mp 170-172° C. IR (film) 3289, 1698, 1669, 1609, 1548, 1445, 1326, 1160, 760 cm$^{-1}$; $^1$H NMR (300 MHz, CDCl$_3$) δ 8.73 (d, J=8.0 Hz, 1H), 8.36 (d, J=8.4 Hz, 1H), 7.88 (dd, J=1.6 and 6.9 Hz, 2H), 7.76 (dt, J=1.2 and 7.1 Hz, 1H), 7.66 (d, J=6.2 Hz, 1H), 7.61-7.39 (m, 7H), 4.53 (t, J=8.1 Hz, 2H), 4.38 (m, 1H), 2.99 (q, J=6.9 Hz, 2H), 1.89 (m, 2H), 1.57-1.25 (m, 16H); ESI-MS m/z (rel intensity) 557 (MH$^+$, 100); HRMS (+ESI) calcd for MH$^+$: 557.2474. found: 557.2477; HPLC purity: 98.8% (MeOH, 100%), 100% (MeOH—H$_2$O, 90:10).

N-(12-(5,11-Dioxo-5H-indeno[1,2-c]isoquinolin-6 (11H)-yl)dodecyl)-benzenesulfonamide (101)

The crude product was eluted with EtOAc—CHCl$_3$ (7:3) to afford the desired compound as an orange solid (62.8 mg, 86%): mp 128-130° C. IR (film) 3275, 1698, 1662, 1610, 1504, 1426, 1319, 1159, 756 cm$^{-1}$; $^1$H NMR (300 MHz, CDCl$_3$) δ 8.72 (d, J=8.1 Hz, 1H), 8.35 (d, J=8.1 Hz, 1H), 7.87 (d, J=7.0 Hz, 2H), 7.84-7.42 (m, 9H), 4.52 (t, J=7.6 Hz, 2H), 4.39 (m, 1H), 2.98 (q, J=6.7 Hz, 2H), 1.89 (m, 2H), 1.59-1.21 (m, 12H); ESI-MS m/z (rel intensity) 571 (MH$^+$, 100); HRMS (+ESI) calcd for MH$^+$: 571.2631. found: 571.2628. Anal. calcd for C$_{34}$H$_{38}$N$_2$O$_4$S: C, 71.55; H, 6.71; N, 4.91. Found: C, 71.70; H, 6.82; N, 5.09.

N-(2-(5,11-Dioxo-5H-indeno[1,2-c]isoquinolin-6 (11H)ethyl)-4-methylbenzenesulfonamide (102)

The crude product was eluted with EtOAc—CHCl$_3$ (2:8) to afford the desired product as an orange solid (57.4 mg, 84%): mp 272-274° C. IR (film) 3209, 1702, 1646, 1611, 1552, 1506, 1427, 1322, 1147, 763 cm$_{-1}$; $_1$H NMR (300 MHz, DMSO-d$_6$) δ 8.55 (d, J=8.0 Hz, 1H), 8.18 (d, J=7.6 Hz, 1H), 8.01 (m, 1H), 7.83-7.76 (m, 2H), 7.58-7.48 (m, 6H), 7.26 (d, J=8.1 Hz, 2H), 4.53 (t, J=7.0 Hz, 2H), 3.24 (t, J=6.7 Hz, 2H), 2.29 (s, 3H); ESI-MS m/z (rel intensity) 443 ([M-H]$^{-1}$, 100); HRMS (+ESI) calcd for MH$^+$: 445.1222. found: 445.1220; HPLC purity: 98.6% (MeOH, 100%), 96.4% (MeOH—H$_2$O, 90:10).

N-(3-(5,11-Dioxo-5H-indeno[1,2-c]isoquinolin-6 (11H)-yl)propyl)-4-methylbenzenesulfonamide (103)

The crude product was eluted with EtOAc—CHCl$_3$ (3:7) to afford the desired product as an orange solid (58.8 mg, 87%): mp 213-216° C. IR (film) 3294, 1705, 1638, 1609, 1548, 1501, 1422, 1327, 1163, 758 cm$^{-1}$; $^1$H NMR (300 MHz, DMSO-d$_6$) δ 8.58 (d, J=8.1 Hz, 1H), 8.21 (d, J=8.4 Hz, 1H), 7.82-7.74 (m, 3H), 7.65-7.63 (m, 2H), 7.59-7.50 (m, 4H), 7.33-7.31 (m, 2H), 4.49 (t, J=7.5 Hz, 2H), 2.93 (m, 2H), 2.33 (s, 3H), 1.92 (m, 2H); ESI-MS m/z (rel intensity) 459 (MH$^+$, 100); HRMS (+ESI) calcd for MH$^+$: 459.1379. found: 459.1384; HPLC purity: 100% (MeOH, 100%), 99.4% (MeOH—H$_2$O, 90:10).

N-(4-(5,11-Dioxo-5H-indeno[1,2-c]isoquinolin-6 (11H)butyl)-4-methylbenzenesulfonamide (104)

The crude product was eluted with EtOAc—CHCl$_3$ (2:8) to afford the desired product as an orange solid (59.7 mg, 90%):

mp 190-192° C. IR (film) 3272, 1699, 1661, 1606, 1545, 1501, 1424, 1312, 1154, 759 cm$^{-1}$; $^1$H NMR (300 MHz, CDCl$_3$) δ 8.71 (d, J=8.1 Hz, 1H), 8.32 (d, J=7.5 Hz, 1H), 7.76-7.70 (m, 3H), 7.64 (d, J=6.9 Hz, 1H), 7.50-7.41 (m, 4H), 7.30-7.26 (m, 2H), 4.76 (t, J=6.3 Hz, 1H), 4.54 (t, J=7.5 Hz, 2H), 3.11 (q, J=6.5 Hz, 2H), 2.40 (s, 3H), 1.98 (m, 2H), 1.76 (m, 2H); ESI-MS m/z (rel intensity) 473 (MH$^+$, 100); HRMS (+ESI) calcd for MNa$^+$: 495.1355. found: 495.1362; HPLC purity: 96.4% (CH$_3$CN, 100%), 97.1% (CH$_3$CN—H$_2$O, 90:10).

N-(5-(5,11-Dioxo-5H-indeno[1,2-c]isoquinolin-6 (11H)pentyl)-4-methylbenzenesulfonamide (105)

The crude product was eluted with EtOAc—CHCl$_3$ (15: 85) to afford the desired product as an orange solid (61.5 mg, 93%): mp 187-188° C. IR (film) 3273, 1694, 1671, 1609, 1548, 1504, 1426, 1325, 1159, 758 cm$^{-1}$; $^1$H NMR (300 MHz, CDCl$_3$) δ 8.72 (d, J=8.1 Hz, 1H), 8.35 (d, J=7.4 Hz, 1H), 7.76-7.70 (m, 3H), 7.65 (d, J=6.8 Hz, 1H), 7.50-7.38 (m, 4H), 7.30-7.27 (m, 2H), 4.55 (m, 3H), 3.02 (q, J=6.4 Hz, 2H), 2.41 (s, 3H), 1.90 (m, 2H), 1.65 (m, 2H), 1.54 (m, 2H); ESI-MS m/z (rel intensity) 487 (MH$^+$, 100); HRMS (+ESI) calcd for MH$^+$: 487.1692. found: 487.1688; HPLC purity: 99.2% (MeOH, 100%), 98.1% (MeOH—H$_2$O, 90:10).

N-(6-(5,11-Dioxo-5H-indeno[1,2-c]isoquinolin-6 (11H)hexyl)-4-methylbenzenesulfonamide (106)

The crude product was eluted with EtOAc—CHCl$_3$ (2:8) to afford the desired product as a red solid (60.2 mg, 92%): mp 146-149° ° C. IR (film) 3583, 1688, 1652, 1608, 1500, 1419, 1314, 1151, 759 cm$^{-1}$; $^1$H NMR (300 MHz, CDCl$_3$) δ 8.73 (d, J=8.0 Hz, 1H), 8.35 (d, J=8.1 Hz, 1H), 7.76-7.71 (m, 3H), 7.66 (d, J=6.7 Hz, 1H), 7.50-7.40 (m, 4H), 7.30-7.27 (m, 2H), 4.53 (m, 3H), 3.00 (q, J=6.2 Hz, 2H), 2.42 (s, 3H), 1.88 (m, 2H), 1.53-1.48 (m, 6H); ESI-MS m/z (rel intensity) 501 (MH$^+$, 100); HRMS (+ESI) calcd for MH$^+$: 501.1848. found: 501.1860; HPLC purity: 96.4% (MeOH, 100%), 97.6% (MeOH—H$_2$O, 90:10).

N-(7-(5,11-Dioxo-5H-indeno[1,2-c]isoquinolin-6 (11H)-yl)heptyl)-4-methylbenzenesulfonamide (107)

The crude product was eluted with EtOAc—CHCl$_3$ (6:4) to afford the desired compound as an orange solid (41.5 mg, 80%): mp 173-175° C. IR (film) 3275, 1696, 1663, 1609, 1575, 1549, 1503, 1426, 1321, 1158, 780 cm$^{-1}$; $^1$H NMR (300 MHz, CDCl$_3$) 8.72 (d, J=7.7 Hz, 1H), 8.36 (d, J=8.4 Hz, 1H), 7.76-7.73 (m, 3H), 7.65 (d, J=5.9 Hz, 1H), 7.50-7.45 (m, 4H), 7.31-7.29 (m, 2H), 4.49 (m, 3H), 2.96 (q, J=6.5 Hz, 2H), 2.42 (s, 3H), 1.87 (m, 2H), 1.49-1.25 (m, 8H); ESI-MS m/z (rel intensity) 537 (MNa$^+$, 100); HRMS (+ESI) calcd for MNa$^+$: 537.1824. found: 537.1819. Anal. calcd for C$_{30}$H$_{30}$N$_2$O$_4$S.0.7H$_2$O: C, 68.34; H, 6.00; N, 5.31. Found: C, 67.97; H, 5.75; N, 4.96.

N-(8-(5,11-Dioxo-5H-indeno[1,2-c]isoquinolin-6 (11H)-yl)octyl)-4-methylbenzenesulfonamide (108)

The crude product was eluted with EtOAc—CHCl$_3$ (6:4) to afford the desired compound as an orange solid (36.0 mg, 70%): mp 136-139° C. IR (film) 3272, 1698, 1663, 1611, 1550, 1504, 1428, 1320, 1159, 757 cm$^{-1}$; $^1$H NMR (300 MHz, CDCl$_3$) δ 8.73 (d, J=8.0 Hz, 1H), 8.36 (d, J=8.1 Hz, 1H), 7.75-7.70 (m, 3H), 7.66 (d, J=6.9 Hz, 1H), 7.50-7.40 (m, 4H), 7.32 (d, J=8.0 Hz, 2H), 4.53 (t, J=8.2 Hz, 2H), 4.31 (m, 1H), 2.97 (t, J=6.7, 2H), 2.42 (s, 3H), 1.88 (m, 2H), 1.56-1.19 (m, 10H); ESI-MS m/z (rel intensity) 529 (MH$^+$, 78); HRMS (+ESI) calcd for MH$^+$: 529.2161. found: 529.2155; HPLC purity: 97.7% (MeOH, 100%), 96.7% (MeOH—H$_2$O, 90:10).

N-(9-(5,11-Dioxo-5H-indeno[1,2-c]isoquinolin-6 (11H)-yl)nonyl)-4-methylbenzenesulfonamide (109)

The crude product was eluted with EtOAc—CHCl$_3$ (7:3) to afford the desired compound as an orange product (61.3 mg, 80%): mp 159-160° C. IR (film) 3276, 1769, 1698, 1663, 1610, 1549, 1504, 1427, 1320, 1158, 758 cm$^{-1}$; $^1$H NMR (300 MHz, CDCl$_3$) δ 8.72 (d, J=8.1 Hz, 1H), 8.36 (d, J=7.4 Hz, 1H), 7.75-7.70 (m, 3H), 7.66 (d, J=6.8 Hz, 1H), 7.49-7.39 (m, 4H), 7.32-7.29 (m, 2H), 4.53 (t, J=7.9 Hz, 2H), 4.33 (t, J=7.1 Hz, 1H), 2.96 (m, 2H), 2.42 (s, 3H), 1.88 (m, 2H), 1.51-1.26 (m, 12H); ESI-MS m/z (rel intensity) 1107 (M$_2$Na$^+$, 18); HRMS (+ESI) calcd for MH$^+$: 543.2318. found: 543.2307. Anal. calcd for C$_{32}$H$_{34}$N$_2$O$_4$S.0.2H$_2$O: C, 70.36; H, 6.35; N, 5.13. Found: C, 70.22; H, 6.35; N, 4.97.

N-(10-(5,11-Dioxo-5H-indeno[1,2-c]isoquinolin-6 (11H)decyl)-4-methylbenzenesulfonamide (110)

The crude product was eluted with EtOAc—CHCl$_3$ (10: 90) to afford the desired product as a red solid (49.4 mg, 78%): mp 133-135° C. IR (film) 3263, 1699, 1663, 1611, 1550, 1504, 1428, 1320, 1159, 758 cm$^{-1}$; $^1$H NMR (300 MHz, CDCl$_3$) δ 8.73 (d, J=8.1 Hz, 1H), 8.36 (d, J=7.4 Hz, 1H), 7.76-7.71 (m, 3H), 7.66 (d, J=6.3 Hz, 1H), 7.50-7.40 (m, 4H), 7.32-7.30 (m, 2H), 4.53 (t, J=7.7 Hz, 2H), 4.33 (t, J=5.9 Hz, 1H), 2.97 (q, J=6.8 Hz, 2H), 2.43 (s, 3H), 1.92 (m, 2H), 1.55-1.19 (m, 14H); APCI-MS m/z (rel intensity) 557 (MH$^+$, 100); HRMS (+APCI) calcd for MH$^+$: 557.2474. found: 557.2478; HPLC purity: 97.0% (MeOH, 100%), 98.8% (MeOH—H$_2$O, 90:10).

N-(11-(5,11-Dioxo-5H-indeno[1,2-c]isoquinolin-6 (11H)-yl)undecyl)-4-methylbenzenesulfonamide (111)

The crude product was eluted with EtOAc—CHCl$_3$ (6:4) to afford the desired compound as an orange solid (45.0 mg, 71.4%): mp 170-172° C. IR (film) 3289, 1698, 1669, 1609, 1575, 1548, 1505, 1445, 1326, 1160, 760 cm$^{-1}$; $^1$H-NMR (300 MHz, CDCl$_3$) δ 8.72 (d, J=8.0 Hz, 1H), 8.36 (d, J=8.0 Hz, 1H), 7.76-7.70 (m, 3H), 7.65 (d, J=6.4 Hz, 1H), 7.49-7.40 (m, 4H), 7.32-7.29 (m, 2H), 4.53 (t, J=7.5 Hz, 2H), 4.33 (br s, 1H), 2.97 (q, J=6.6 Hz, 2H), 2.43 (s, 3H), 1.90 (m, 2H), 1.58-1.23 (m, 16H); ESI-MS m/z (rel intensity) 571 (MH$^+$, 100); HRMS (+ESI) calcd for MH$^+$: 571.2631. found: 571.2625; HPLC purity: 96.7% (MeOH, 100%), 96.7% (MeOH—H$_2$O, 95:5).

N-(12-(5,11-Dioxo-5H-indeno[1,2-c]isoquinolin-6 (11H)-yl)dodecyl)-4-methylbenzenesulfonamide (112)

The crude product was eluted with EtOAc—CHCl$_3$ (6:4) to afford the desired compound as an orange solid (55 mg, 73%): mp 108-112° C. IR (film) 3275, 1698, 1666, 1611, 1550, 1504, 1428, 1320, 1160, 757 cm$^{-1}$; $^1$H NMR (300 MHz, CDCl$_3$) δ 8.72 (d, J=8.2 Hz, 1H), 8.36 (d, J=7.0 Hz, 1H), 7.75-7.63 (m, 4H), 7.49-7.29 (m, 6H), 4.53 (t, J=7.3 Hz, 2H), 4.27 (m, 1H), 2.96 (q, J=6.7 Hz, 2H), 2.42 (s, 3H), 1.90 (m, 2H), 1.57-1.22 (m, 18H); ESI-MS m/z (rel intensity) 607

(MNa⁺, 30); HRMS (+ESI) calcd for MNa⁺: 607.2607. found: 607.2604. Anal. calcd for $C_{35}H_{40}H_2O_4S$: C, 71.89; H, 6.89; N, 4.79. Found: C, 71.49; H, 6.97; N, 4.83.

N-(2-(5,11-Dioxo-5H-indeno[1,2-c]isoquinolin-6 (11H)-yl)ethyl)-4-bromobenzenesulfonamide (113)

The crude product was eluted with EtOAc—CHCl₃ (2:8) to afford the desired product as an orange solid (64.2 mg, 82%): mp 260-263° C. IR (film) 3208, 1707, 1645, 1611, 1551, 1506, 1427, 1324, 1146, 827 cm⁻¹; ¹H NMR (300 MHz, DMSO-d₆) δ 8.56 (d, J=8.0 Hz, 1H), 8.22 (m, 2H), 7.80-7.69 (m, 4H), 7.64-7.61 (m, 2H), 7.56-7.48 (m, 4H), 4.54 (t, J=6.4 Hz, 2H), 3.26 (t, J=6.7 Hz, 2H); ESI-MS m/z (rel intensity) 507/509 ([M-H]⁻, 78/100); HRMS (−ESI) calcd for [M-H]⁻: 507.0014. found: 507.0017. HPLC purity: 97.7% (MeOH, 100%), 95.3% (MeOH—H₂O, 90:10).

N-(3-(5,11-Dioxo-5H-indeno[1,2-c]isoquinolin-6 (11H)-yl)propyl)-4-bromobenzenesulfonamide (114)

The crude product was eluted with EtOAc—CHCl₃ (9:1) to afford the desired product as an orange solid (40.2 mg, 52%): mp 241-243° C. IR (film) 3303, 1762, 1696, 1653, 1609, 1549, 1505, 1427, 1325, 1166, 751 cm⁻¹; ¹H NMR (300 MHz, DMSO-d₆) δ 8.72 (d, J=8.1 Hz, 1H), 8.28 (d, J=7.6 Hz, 1H), 7.79-7.74 (m, 3H), 7.66-7.39 (m, 7H), 6.11 (t, J=6.7 Hz, 1H), 4.67 (t, J=6.0 Hz, 2H), 3.01 (q, J=6.6 Hz, 2H), 2.18 (m, 2H); ESI-MS m/z (rel intensity) 523/525 (MH⁺, 100/93); HRMS (+ESI) calcd for MH⁺: 523.0327. found: 523.0335; HPLC purity: 95.4% (MeOH, 100%), 95.7% (MeOH—H₂O, 95:5).

N-(4-(5,11-Dioxo-5H-indeno[1,2-c]isoquinolin-6 (11H)-yl)butyl)-4-bromobenzenesulfonamide (115)

The crude product was eluted with EtOAc—CHCl₃ (2:8) to afford the desired product as a red solid (63.7 mg, 84%): mp 176-177° C. IR (film) 3257, 1698, 1663, 1611, 1576, 1503, 1427, 1332, 1163, 757 cm⁻¹; ¹H NMR (300 MHz, CDCl₃) δ 8.71 (d, J=8.1 Hz, 1H), 8.32 (d, J=8.0 Hz, 1H), 7.76-7.70 (m, 3H), 7.67-7.63 (m, 3H), 7.49-7.40 (m, 4H), 4.98 (t, J=6.3 Hz, 1H), 4.54 (t, J=7.3 Hz, 2H), 3.14 (q, J=6.4 Hz, 2 Hz), 1.99 (m, 2H), 1.80 (m, 2H); ESI-MS m/z (rel intensity) 537/539 (MH⁺, 89/100); HRMS (+ESI) calcd for MH⁺: 537.0484. found: 537.0489; HPLC purity: 99.4% (MeOH, 100%), 98.1% (MeOH—H₂O, 90:10).

N-(5-(5,11-Dioxo-5H-indeno[1,2-c]isoquinolin-6 (11H)-yl)pentyl)-4-bromobenzenesulfonamide (116)

The crude product was eluted with EtOAc—CHCl₃ (15:85) to afford the desired product as an orange solid (68.0 mg, 91%): mp 169-171° C. IR (film) 3271, 1698, 1661, 1611, 1576, 1505, 1428, 1332, 1163, 757 cm⁻¹; ¹H NMR (300 MHz, CDCl₃) δ 8.73 (d, J=8.0 Hz, 1H), 8.36 (d, J=7.3 Hz, 1H), 7.74-7.70 (m, 3H), 7.66-7.61 (m, 3H), 7.49-7.41 (m, 4H), 4.73 (t, J=6.0 Hz, 1H), 4.54 (t, J=7.2 Hz, 2H), 3.04 (q, J=6.4 Hz, 2 Hz), 1.92 (m, 2H), 1.68 (m, 2H), 1.53 (m, 2H); ESI-MS m/z (rel intensity) 551/553 (MH⁺, 100/98); HRMS (+ESI) calcd for MH⁺: 551.0640. found: 551.0652; HPLC purity: 98.3% (MeOH, 100%), 98.2% (MeOH—H₂O, 90:10).

N-(6-(5,11-Dioxo-5H-indeno[1,2-c]isoquinolin-6 (11H)-yl)hexyl)-4-bromobenzenesulfonamide (117)

The crude product was eluted with EtOAc—CHCl₃ (2:8) to afford the desired product as a red solid (68.5 mg, 93%): mp 188-190° C. IR (film) 3199, 1760, 1698, 1636, 1610, 1574, 1503, 1458, 1330, 1160, 757 cm⁻¹; ¹H NMR (300 MHz, CDCl₃) δ 8.73 (d, J=8.1 Hz, 1H), 8.35 (d, J=7.5 Hz, 1H), 7.76-7.71 (m, 3H), 7.66-7.64 (m, 3H), 7.50-7.39 (m, 4H), 4.74 (t, J=6.2 Hz, 1H), 4.54 (t, J=7.2 Hz, 2H), 3.03 (q, J=6.4 Hz, 2 Hz), 1.89 (m, 2H), 1.57-1.48 (m, 6H); ESI-MS m/z (rel intensity) 565/567 (MH⁺, 91/100); HRMS (+ESI) calcd for MNa⁺: 587.0616. found: 587.0610; HPLC purity: 96.6% (MeOH, 100%), 98.2% (MeOH—H₂O, 90:10).

N-(7-(5,11-Dioxo-5H-indeno[1,2-c]isoquinolin-6 (11H)-yl)heptyl)-4-bromobenzenesulfonamide (118)

The crude product was eluted with EtOAc—CHCl₃ (5:95) to afford the desired product as a red solid (70.5 mg, 96%): mp 160-161° C. IR (film) 3290, 1699, 1661, 1610, 1550, 1503, 1427, 1320, 1161, 757 cm⁻¹; ¹H NMR (300 MHz, CDCl₃) δ 8.72 (d, J=8.1 Hz, 1H), 8.36 (d, J=7.7 Hz, 1H), 7.76-7.70 (m, 3H), 7.66-7.63 (m, 3H), 7.50-7.39 (m, 4H), 4.69 (t, J=6.1 Hz, 1H), 4.51 (t, J=7.7 Hz, 2H), 3.01 (q, J=6.7 Hz, 2 Hz), 1.90 (m, 2H), 1.53-1.36 (m, 8H); ESI-MS m/z (rel intensity) 579/581 (MH⁺, 92/100); HRMS (+ESI) calcd for MNa⁺: 579.0953. found: 579.0959; HPLC purity: 98.3% (MeOH, 100%), 98.9% (MeOH—H₂O, 90:10).

N-(8-(5,11-Dioxo-5H-indeno[1,2-c]isoquinolin-6 (11H)-yl)octyl)-4-bromobenzenesulfonamide (119)

The crude product was eluted with EtOAc—CHCl₃ (6:4) to afford the desired product as an orange solid (67.6 mg, 78%): mp 119-121° C. IR (film) 3272, 1698, 1662, 1611, 1550, 1504, 1428, 1331, 1163, 757 cm⁻¹; ¹H NMR (300 MHz, CDCl₃) δ 8.73 (d, J=8.1 Hz, 1H), 8.36 (d, J=8.4 Hz, 1H), 7.74-7.71 (m, 3H), 7.67-7.64 (m, 3H), 7.47-7.43 (m, 4H), 4.53 (t, J=7.7 Hz, 2H), 4.43 (t, J=6.4 Hz, 1H), 3.00 (q, J=6.8 Hz, 2H), 1.91 (m, 2H), 1.55-1.20 (m, 10H); ESI-MS m/z (rel intensity) 593/595 (MH⁺, 100/91); HRMS (+ESI) calcd for MH⁺: 593.1110. found: 593.1105. Anal. calcd for $C_{30}H_{29}BrN_2O_4S$: C, 60.71; H, 4.92; N, 4.72. Found: C, 60.69; H, 5.01; N, 4.67.

N-(9-(5,11-Dioxo-5H-indeno[1,2-c]isoquinolin-6 (11H)-yl)nonyl)-4-bromobenzenesulfonamide (120)

The crude product was eluted with EtOAc—CHCl₃ (6:4) to afford the desired product as an orange solid (52.2 mg, 61%): mp 143-146° C. IR (film) 3288, 1697, 1662, 1610, 1550, 1504, 1427, 1320, 1162, 757 cm⁻¹; ¹H NMR (300 MHz, CDCl₃) δ 8.72 (d, J=8.1 Hz, 1H), 8.35 (d, J=8.2 Hz, 1H), 7.74-7.71 (m, 3H), 7.66-7.63 (m, 3H), 7.49-7.40 (m, 4H), 4.53 (t, J=6.4 Hz, 3H), 2.99 (q, J=6.8 Hz, 2H), 1.91 (m, 2H), 1.58-1.25 (m, 12H); ESI-MS m/z (rel intensity) 607/609 (MH⁺, 88/100); HRMS (+ESI) calcd for MH⁺: 607.1266. found: 607.1263. Anal. calcd for $C_{31}H_{31}BrN_2O_4S$: C, 61.28; H, 5.14; N, 4.61. Found: C, 61.22; H, 5.16; N, 4.57.

N-(10-(5,11-Dioxo-5H-indeno[1,2-c]isoquinolin-6 (11H)-yl)decyl)-4-bromobenzenesulfonamide (121)

The crude product was eluted with EtOAc—CHCl₃ (6:4) to afford the desired product as an orange solid (65.2 mg, 77%): mp 160-163° C. IR (film) 3262, 1696, 1658, 1609, 1548, 1503, 1426, 1321, 1158, 753 cm⁻¹; ¹H NMR (500 MHz, CDCl₃) δ 8.72 (d, J=8.0 Hz, 1H), 8.35 (d, J=8.0 Hz, 1H), 7.74-7.71 (m, 3H), 7.66-7.64 (m, 3H), 7.48-7.40 (m, 4H), 4.52 (t, J=7.0 Hz, 2H), 4.40 (m, 1H), 2.97 (q, J=6.5 Hz, 2H), 1.91-1.88 (m, 2H), 1.54-1.22 (m, 14H); ESI-MS m/z (rel intensity) 621/623 (MH$^+$, 100/99.8); HRMS (+ESI) calcd for MH$^+$: 621.1423. found: 621.1430. Anal. calcd for $C_{32}H_{33}BrN_2O_4S$: C, 61.83; H, 5.35; N, 4.51. Found: C, 61.95; H, 5.40; N, 4.71.

N-(11-(5,11-Dioxo-5H-indeno[1,2-c]isoquinolin-6 (11H)-yl)undecyl)-4-bromobenzenesulfonamide (122)

The crude product was eluted with EtOAc—CHCl$_3$ (6:4) to afford the desired product as an orange solid (60.6 mg, 86%): mp 150-153° C. IR (film) 3310, 1705, 1661, 1608, 1548, 1504, 1422, 1328, 1156, 757 cm$^{-1}$; $^1$H-NMR (300 MHz, CDCl$_3$) 8.73 (d, J=8.0 Hz, 1H), 8.36 (d, J=8.2 Hz, 1H), 7.75-7.71 (m, 3H), 7.66-7.61 (m, 3H), 7.49-7.38 (m, 4H), 4.54 (t, J=7.5 Hz, 2H), 4.40 (t, J=6.1 Hz, 1H), 2.99 (q, J=6.8 Hz, 2H), 1.90 (m, 2H), 1.56-1.23 (m, 16H); ESI-MS m/z (rel intensity) 635/637 (MH$^+$, 100/92); HRMS (+ESI) calcd for MH$^+$: 635.1579. found: 635.1584. Anal. calcd for $C_{33}H_{35}BrN_2O_4S$: C, 62.36; H, 5.55; N, 4.41. Found: C, 62.15; H, 5.62; N, 4.44.

N-(12-(5,11-Dioxo-5H-indeno[1,2-c]isoquinolin-6 (11H)-yl)dodecyl)-4-bromobenzenesulfonamide (123)

The crude product was eluted with EtOAc—CHCl$_3$ (6:4) to afford the desired product as an orange solid (65.3 mg, 78%): mp 118-120° C. IR (film) 3275, 1698, 1664, 1611, 1550, 1504, 1428, 1332, 1164, 757 cm$^{-1}$; $^1$H NMR (300 MHz, CDCl$_3$) δ 8.72 (d, J=8.3 Hz, 1H), 8.35 (d, J=8.1 Hz, 1H), 7.73-7.63 (m, 6H), 7.49-7.40 (m, 4H), 4.53 (t, J=7.8 Hz, 2H), 4.41 (t, J=5.9 Hz, 1H), 2.99 (q, J=6.7 Hz, 2H), 1.90-1.87 (m, 2H), 1.58-1.21 (m, 18H); ESI-MS m/z (rel intensity) 649/651 (MH$^+$, 100/80); HRMS (+ESI) calcd for MH$^+$: 649.1736. found: 649.1728. Anal. calcd for $C_{34}H_{37}BrN_2O_4S \cdot 0.5H_2O$: C, 62.00; H, 5.82; N, 4.25. Found: C, 61.71; H, 5.62; N, 4.15.

General Procedure for the Preparation of Indenoisoquinoline Sulfonamides 132-136

Indenoisoquinoline salts 127-131 (50 mg, 0.088-0.102 mmol), prepared previously via the reported literature procedures, were dissolved in CHCl$_3$ (15 mL), Et$_3$N (2 equiv) in CHCl$_3$ (1 mL) was added, and the solutions were stirred at room temperature for 5 min. Benzenesulfonyl chloride (2 equiv) was added. The mixtures were heated at reflux for 3 h, and then washed with sat. NaHCO$_3$ (50 mL) and brine (50 mL). The organic layer was dried over anhydrous Na$_2$SO$_4$, filtered and concentrated, adsorbed onto SiO$_2$, and purified by flash column chromatography (SiO$_2$), eluting with EtOAc—CHCl$_3$ to provide the indenoisoquinoline sulfonamide products 132-136 in high purity.

N-(3-(3-Nitro-5,11-dioxo-9-phenyl-5H-indeno[1,2-c]isoquinolin-6(11H)-yl)-propyl)benzenesulfonamide (132)

The crude product was eluted with EtOAc—CHCl$_3$ (2:8) to afford the desired product as an orange solid (22.9 mg, 37%): mp 246-247° C. IR (film) 3318, 1706, 1658, 1615, 1553, 1501, 1448, 1383, 1336, 1153, 749 cm$^{-1}$; $^1$H NMR (300 MHz, DMSO-d$_6$) δ 8.79 (d, J=2.2 Hz, 1H), 8.66 (d, J=9.0 Hz, 1H), 8.54 (dd, J=6.5 and 2.4 Hz, 1H), 7.89-8.75 (m, 8H), 7.61-7.45 (m, 6H) 4.50 (m, 2H), 3.02 (m, 2H), 1.97 (m, 2H); ESI-MS m/z (rel intensity) 566 (MH$^+$, weak); HRMS (+ESI) calcd for MH$^+$: 566.1386. found: 566.1378; HPLC purity: 100% (MeOH, 100%), 99.1% (MeOH—H$_2$O, 90:10).

N-(3-(5,11-Dioxo-5H-[1,3]dioxolo[4,5-g]indeno[1, 2-c]isoquinolin-6(11H)-yl)-propyl)benzenesulfonamide (133)

The crude product was eluted with EtOAc—CHCl$_3$ (2:8) to afford the desired product as an orange solid (51.3 mg, 81%): mp 225-226° C. IR (film) 3223, 1700, 1636, 1608, 1562, 1499, 1467, 1329, 1174, 765 cm$^{-1}$; $^1$H NMR (300 MHz, DMSO-d$_6$) δ 7.88-7.76 (m, 4H), 7.60 (d, J=5.3 Hz, 1H), 7.58-7.47 (m, 7H), 6.19 (s, 2H), 4.43 (t, J=7.3 Hz, 2H), 2.95 (q, J=6.0 Hz, 2H), 1.90 (m, 2H); APCI-MS m/z (rel intensity) 489 (MH$^+$, 100); HRMS (+APCI) calcd for MNa$^+$: 511.0940. found: 511.0949; HPLC purity: 100% (MeOH, 100%), 99.9% (MeOH:H$_2$O, 90-10).

Methyl 2,3-Dimethoxy-5,11-dioxo-6-(3-(phenylsulfonamido)propyl)-6,11-dihydro-5H-indeno[1,2-c]isoquinoline-9-carboxylate (134)

The crude product was eluted with EtOAc—CHCl$_3$ (4:6) to afford the desired product as a deep purple solid (53.7 mg, 88%): mp 249-251° C. IR (film) 3244, 1727, 1645, 1611, 1554, 1511, 1482, 1321, 1259, 1161, 802, 764 cm$^{-1}$; $^1$H NMR (300 MHz, CDCl$_3$) δ 8.15-8.12 (m, 2H), 8.07 (s, 1H), 7.92 (d, J=7.1 Hz, 2H), 7.63 (s, 1H), 7.56-7.45 (m, 4H), 6.04 (t, J=6.4 Hz, 1H), 4.65 (t, J=6.1 Hz, 2H), 4.07 (s, 3H), 4.03 (s, 3H), 3.97 (s, 3H), 3.08 (q, J=6.2 Hz, 2H), 2.12 (m, 2H); APCI-MS m/z (rel intensity) 563 (MH$^+$, 100); HRMS (+APCI) calcd for MNa$^+$: 585.1308. found: 585.1302; HPLC purity: 100% (MeOH, 100%), 99.9% (MeOH:H$_2$O, 90-10).

N-(3-(3-Nitro-5,11-dioxo-5H-indeno[1,2-c]isoquinolin-6(11H)-yl)propyl)-benzenesulfonamide (135)

The crude product was eluted with EtOAc—CHCl$_3$ (2:8) to afford the desired product as an orange solid (28.6 mg, 46%): mp 258-259° C. IR (film) 3214, 1699, 1656, 1613, 1553, 1503, 1453, 1423, 1381, 1324, 1259, 1158, 802, 746 cm$^{-1}$; $^1$H NMR (300 MHz, DMSO-d$_6$) δ 8.88 (d, J=2.4 Hz, 1H), 8.74 (d, J=8.9 Hz, 1H), 8.60 (dd, J=6.5 and 2.4 Hz, 1H), 7.91 (t, J=8.0 Hz, 2H), 7.82 (dd, J=6.7 and 1.5 Hz, 2H), 7.66-7.57 (m, 6H), 4.51 (t, J=8.0 Hz, 2H), 3.01 (q, J=6.2 Hz, 2H), 1.96 (m, 2H); APCI-MS m/z (rel intensity) 490 (MH$^+$, 100); HRMS (+APCI) calcd for MH$^+$: 490.1073. found: 490.1070; HPLC purity: 97.1% (MeOH, 100%), 100% (MeOH—H$_2$O, 90:10).

N-(3-(2,3-Dimethoxy-5,11-dioxo-5H-indeno[1,2-c] isoquinolin-6(11H)-yl)-propyl)benzenesulfonamide (136)

The crude product was eluted with EtOAc—CHCl$_3$ (4:6) to afford the desired product as an orange solid (58.9 mg, 94%): mp 249-250° C. IR (film) 3166, 1701, 1626, 1612, 1589, 1554, 1513, 1478, 1426, 1335, 1260, 1171, 1093, 1021, 789 cm$^{-1}$; $^1$H NMR (300 MHz, CDCl$_3$) δ 8.12 (s, 1H), 7.91 (dd, J=6.8 and 1.6 Hz, 2H), 7.64 (s, 1H), 7.60 (d, J=6.6 Hz, 1H), 7.52-7.37 (m, 6H), 6.12 (t, J=6.9 Hz, 1H), 4.65 (t, J=5.9 Hz, 2H), 4.07 (s, 3H), 4.03 (s, 3H), 3.05 (q, J=6.3 Hz, 2H), 2.13 (m, 2H); ESI-MS m/z (rel intensity) 505 (MH$^+$, 100); HRMS (+ESI) calcd for MH$^+$: 505.1433. found: 505.1423; HPLC purity: 100% (MeOH, 100%), 100% (MeOH—H$_2$O, 90:10).

General Procedure for the Preparation of Bisindenoisoquinolines 140-142

Diamines 137-139 (100 mg, 1 equiv) were dissolved in CHCl$_3$ (10 mL) and added to a solution of lactone 11 (2 equiv)

in CHCl$_3$ (20 mL). The mixtures were stirred at reflux for 16 h, and then concentrated, adsorbed onto SiO$_2$, and purified with flash column chromatography (SiO$_2$), eluting with CHCl$_3$ to afford the products 140-142 as orange or red solids.

6,6'-(Decane-1,10-diyl)bis(5H-indeno[1,2-c]iso-quinoline-5,11[6H]-dione) (140)

The general procedure provided the product as an orange solid (223 mg, 64%): mp 201-202° C. IR (film) 1762, 1657, 1609 cm$^{-1}$; $^1$H NMR (300 MHz, CDCl$_3$) δ 8.72 (d, J=8.1 Hz, 2H), 8.35 (d, J=8.2 Hz, 2H), 7.75 (d, J=8.3 Hz, 2H), 7.64 (d, J=6.4 Hz, 2H), 7.49-7.39 (m, 8H), 4.53 (t, J=7.9 Hz, 4H), 1.90 (m, 4H), 1.57 (m, 4H), 1.54-1.38 (m, 8H); ESI-MS m/z (rel intensity) 633 (MH$^+$, 57); HRMS (+ESI) calcd for MH$^+$: 633.2753. found: 633.2763. Anal. calcd for C$_{42}$H$_{36}$N$_2$O$_4$: C, 79.72; H, 5.73; N, 4.43. Found: C, 79.53; H, 5.76; N, 4.39.

6,6'-(Undecane-1,11-diyl)bis(5H-indeno[1,2-c]iso-quinoline-5,11[6H]-dione) (141)

The general procedure provided the product as an orange solid (223 mg, 64%): mp 201-202° C. IR (film) 1764, 1736, 1702, 1655 cm$^{-1}$; $^1$H NMR (300 MHz, CDCl$_3$) δ 8.71 (d, J=8.1 Hz, 2H), 8.35 (d, J=7.7 Hz, 2H), 7.82 (d, J=8.2 Hz, 2H), 7.64 (d, J=6.5 Hz, 2H), 7.48-7.38 (m, 8H), 4.52 (t, J=8.1 Hz, 4H), 1.92 (m, 4H), 1.58 (m, 4H), 1.41-1.33 (m, 10H); ESI-MS m/z (rel intensity) 647 (MH$^+$, 100); HRMS (+ESI) calcd for MH$^+$: 647.2910. found: 647.2908. Anal. calcd for C$_{43}$H$_{38}$N$_2$O$_4$: C, 79.85; H, 5.92; N, 4.33. Found: C, 79.80; H, 5.99; N, 4.29.

6,6'-(Dodecane-1,12-diyl)bis(5H-indeno[1,2-c]iso-quinoline-5,11[6H]-dione) (142)

The general procedure provided the product as a red solid (135 mg, 82%): mp 226-228° C. IR (film) 1694, 1660, 1609 cm$^{-1}$; $^1$H NMR (300 MHz, CDCl$_3$): δ8.71 (d, J=8.0 Hz, 2H), 8.35 (d, J=8.1 Hz, 2H), 7.74 (t, J=7.5 Hz, 2H), 7.64 (d, J=6.9 Hz, 2H), 7.48-7.37 (m, 8H), 4.52 (t, J=7.9 Hz, 4 Hz), 1.90 (m, 4H), 1.53 (m, 4H), 1.40-1.31 (m, 12H); ESI-MS m/z (rel intensity) 661 (MH$^+$, 100); HRMS (+ESI) calcd for MH$^+$: 661.3066. found: 661.3054; HPLC purity: 99.7% (CH$_3$CN, 100%), 97.0% (CH$_3$CN—H$_2$O, 95:5).

Bis-1,3-{(5,6-dihydro-5,11-diketo-11H-indeno[1,2-c]isoquinoline)-(6-propyl-tert-BOCamino)}propane (144)

Tetramine 143 (100 mg, 0.53 mmol) was diluted in CHCl$_3$ (10 mL) and added to a solution of lactone 11 (276 mg, 1.12 mmol) in CHCl$_3$ (40 mL). The reaction mixture was stirred at reflux for 72 h. Et$_3$N (270 mg, 2.66 mmol) and Boc$_2$O (360 mg, 1.65 mmol) were then added to the cooled mixture, and stirring continued at room temperature for 16 h. The mixture was concentrated, adsorbed on to SiO$_2$, and purified with flash column chromatography (SiO$_2$), eluting with EtOAc-hexane (2:8) and then with MeOH—CHCl$_3$ (3:97) to provide the product as an orange solid (352 mg, 78%): mp 84-86° C. (lit. 86-88° C.). $^1$H NMR (CDCl$_3$) δ 8.63 (d, J=7.9 Hz, 2H), 8.24 (d, J=7.6 Hz, 2H), 7.65 (t, J=7.3 Hz, 2H), 7.55 (d, J=6.9 Hz, 2H), 7.41-7.30 (m, 8H), 4.49 (br s, 4H), 3.44 (br s, 4H), 3.27 (t, J=6.3 Hz, 4H), 2.08 (brs, 4H), 1.86 (br s, 2H), 1.41 (br s, 18H).

Bis-1,3-{(5,6-dihydro-5,11-diketo-11H-indeno[1,2-c]isoquinoline)-6-propyl-amino}propane Bis(trifluoroacetate) (145)

Boc-protected bis(indenoisoquinoline) 144 (352 mg, 0.41 mmol) was diluted in CF$_3$COOH (30 mL) and the mixture was stirred at room temperature for 2 h. The reaction mixture was concentrated, and the resultant solid was triturated with chloroform and filtered to provide the product as an orange solid (247 mg, 93%): mp 224-226° C. (lit. 225-227° C.). $^1$H NMR (DMSO-d$_6$) δ8.59-8.57 (m, 6H), 8.22 (d, J=8.1 Hz, 2H), 7.86-7.78 (m, 4H), 7.62-7.49 (m, 8H), 4.60 (t, J=6.4 Hz, 4H), 3.08 (br s, 4H), 2.96 (br s, 4H), 2.15 (br s, 4H), 1.90 (m, 2H); HPLC purity: 97.7% (MeOH—H$_2$O, 80:20), 97.6% (MeOH—H$_2$O, 70:30).

Biological Tests

Topoisomerase I-Mediated DNA Cleavage Reactions.

Human recombinant Top1 was purified from baculovirus as previously described. DNA cleavage reactions were prepared as previously reported with the exception of the DNA substrate. Briefly, a 117-bp DNA oligonucleotide (Integrated DNA Technologies) encompassing the previously identified Top1 cleavage sites in the 161-bp fragment from pBluescript SK(–) phagemid DNA was employed. This 117-bp oligonucleotide contains a single 5'-cytosine overhang, which was 3'-end-labeled by fill-in reaction with [α-$^{32}$P]dGTP in React 2 buffer (50 mM Tris-HCl, pH 8.0, 100 mM MgCl$_2$, 50 mM NaCl) with 0.5 unit of DNA polymerase I (Klenow fragment, New England BioLabs). Unincorporated [$^{32}$P]dGTP was removed using mini Quick Spin DNA columns (Roche, Indianapolis, Ind.), and the eluate containing the 3'-end-labeled DNA substrate was collected. Approximately 2 nM radiolabeled DNA substrate was incubated with recombinant Top1 in 20 µL of reaction buffer [10 mM Tris-HCl (pH 7.5), 50 mM KCl, 5 mM MgCl$_2$, 0.1 mM EDTA, and 15 µg/mL BSA] at 25° C. for 20 min in the presence of various concentrations of compounds. The reactions were terminated by adding SDS (0.5% final concentration) followed by the addition of two volumes of loading dye (80% formamide, 10 mM sodium hydroxide, 1 mM sodium EDTA, 0.1% xylene cyanol, and 0.1% bromphenol blue). Aliquots of each reaction mixture were subjected to 20% denaturing PAGE. Gels were dried and visualized by using a phosphoimager and ImageQuant software (Molecular Dynamics). For simplicity, cleavage sites were numbered as previously described in the 161-bp fragment.

Gel-Based Assay Measuring the Inhibition of Recombinant Tdp1.

A 5'-[$^{32}$P]-labeled single-stranded DNA oligonucleotide containing a 3'-phosphotyrosine (N14Y) was generated as described by Dexheimer et al. The DNA substrate was then incubated with 5 pM recombinant Tdp1 in the absence or presence of inhibitor for 15 min at room temperature in a buffer containing 50 mM Tris HCl, pH 7.5, 80 mM KCl, 2 mM EDTA, 1 mM DTT, 40 µg/ml BSA and 0.01% Tween-20. Reactions were terminated by the addition of 1 volume of gel loading buffer [99.5% (v/v) formamide, 5 mM EDTA, 0.01% (w/v) xylene cyanol, and 0.01% (w/v) bromphenol blue]. Samples were subjected to a 16% denaturing PAGE and gels were exposed after drying to a PhosphorImager screen (GE Healthcare). Gel images were scanned using a Typhoon 8600 (GE Healthcare) and densitometric analyses were performed using the ImageQuant software (GE Healthcare).

Gel-based Assay Measuring the Inhibition of Endogenous Human Tdp1 in Whole Cell Extract 1×10^7 DT40 knockout cells for chicken Tdp1 and complemented with human Tdp1 were collected, washed and centrifuged. Cell pellet was then resuspended with 100 µL of CellLytic M Cell Lysis Reagent (SIGMA-Aldrich C2978). After 15 min, the lysate was centrifuged at a 12,000 g for 10 min and the supernatant was transferred to a new tube. Protein concentration was determined using a nanodrop spectrophotometer (Invitrogen) and the whole cell extract was stored at −80° C. The 5'-[$^{32}$P]-labeled single-stranded N14Y DNA oligonucleotide containing a 3'-phosphotyrosine (see above) was incubated with 1-5 µg/ml of whole cell extract in the absence or presence of inhibitor for 15 min at room temperature in the same assay buffer used for recombinant Tdp1 (see section above). Reactions were then treated similarly to the recombinant enzyme containing samples (see section above).

All compounds were first tested in gel based assays for Tdp1 inhibition using recombinant (rec.) human Tdp1 and only the active compounds were tested for human Tdp1 inhibition in whole cell extract (WCE). Furamidine was included in all experiments as positive control.

Determination of the Mechanism of Inhibition of Compound 70.

Mechanistic characterization of compound 70 was carried out using a FRET assay employing a custom designed substrate (Bermingham et al. manuscript in preparation). The assay followed the real-time observation of reaction timecourse data, permitting an accurate measure of the reaction rate in the presence of an inhibitor. The mechanism of inhibition of 70 was observed by measuring the rate of the Tdp1 catalyzed reaction under a matrix of varying substrate and inhibitor concentrations. In the assay, Tdp1 FRET substrate was present as a dilution series ranging 2.25 µM to 0.035 µM over eight 2-fold steps. Compound 70 was present at three concentrations equaling 0.33×IC$_{50}$, 1.0×IC$_{50}$ and 3.0×IC$_{50}$. A "no inhibitor" sample was also included, to allow measurement of the rate of reaction in the absence of inhibition.

Immediately prior to executing the assay, stocks of Tdp1 enzyme, Tdp1 FRET substrate and compound 70 were created at 3× their final desired assay concentrations. 5 µL of compound 70 stock dilutions were combined with 5 µL of a 1.5 nM Tdp1 stock in appropriate wells in a low volume 384 well plate (Greiner #784900. Greiner, Monroe, N.C.) and allowed to incubate on ice for 1 hour to ensure complete binding equilibrium. After incubation, 5 µL of the 3×Tdp1 FRET substrate dilution series was added to the plate to initiate the reaction. The assay plate was placed in a Tecan Safire plate reader (Tecan US, Durham, N.C.) and timecourse data observed for 1 h at excitation and emission wavelengths of 525 nm (band width=5) and 545 nm (band width=5) respectively for all wells. The final assay volume was 15 µL, with Tdp1 present at a final fixed concentration of 500 pM for all wells. Experimental data was plotted as reaction rate versus substrate concentration for all inhibitor concentrations and analyzed using models for competitive, non-competitive (pure and mixed) and uncompetitive inhibition (Equations 1a-d respectively) using GraphPad Prism (Graphpad, La Jolla, Calif.). To identify the most appropriate mechanistic model describing the inhibition data, Akaike's Information Criterion (Akaike, H., 1973). Information theory and an extension of the maximum likelihood principle in *Second International Symposium on Information Theory* (Csaki, B. N. P. a. F. ed., Budapest: Akademiai Kiado) was employed.

Equations

A. Competitive Inhibition $$v = \frac{V_{max}[s]}{[S] + K_m\left(1 + \frac{[I]}{K_i}\right)}$$

Where $V_{max}$ is maximum reaction velocity, [S] is the substrate concentration, $K_m$ is the Michaelis constant, and $K_i$ is the inhibition constant.

B. Pure Noncompetitive Inhibition $$v = \frac{V_{max}[s]}{([S] + K_m)\left(1 + \frac{[I]}{K_i}\right)}$$

Where $K_i$ is the inhibition constant in the presence or absence of substrate.

C. Mixed Noncompetitive Inhibition $$v = \frac{V_{max}[s]}{[S]\left(1 + \frac{[I]}{K_{ies}}\right) + K_m\left(1 + \frac{[I]}{K_{ie}}\right)}$$

Where $K_{ie}$ is the inhibition constant for binding to the enzyme in the absence of substrate, and $K_{ies}$ the inhibition constant for binding to the ES complex.

D. Uncompetitive Inhibition $$v = \frac{V_{max}[s]}{[S]\left(1 + \frac{[I]}{K_{ies}}\right) + K_m}$$

Where $K_{ies}$ is the inhibition constant for binding to the ES complex.

Surface Plasmon Resonance Analysis

Binding experiments were performed on a Biacore T100 instrument (GE, Piscataway N.J.). Tdp1 was amine coupled to a CM5 sensor chip (GE Healthcare, Piscataway N.J.). Coupling reagents [N-ethyl-N'-(3-dimethylaminopropyl)carbodiimide] (EDC), N-hydroxysuccinimide (NHS) and ethanolamine were purchased from GE Healthcare, (Piscataway N.J.). Neutravidin was obtained from Pierce. In order to protect the amine groups within the active site from modification, Tdp1 was bound with a 14-base oligonucleotide before coupling to the surface. Specifically, 1 µM Tdp1 was incubated with 2 µM of a 14-base oligonucleotide containing a phosphate group at the 3'-end (GATCTAAAAGACTT) (SEQ ID NO: 1) in 10 mM sodium acetate pH 4.5 for 20 min. The CM5 chip surface was activated for 7 min with 0.1 M NHS and 0.4 M EDC at a flow rate of 20 µL/min and Tdp1-oligonucleotide mixture was injected until approximately 4000 RU's was attached. Activated amine groups were quenched with an injection of 1 M solution of ethanolamine pH 8.0 for 7 min. Any bound oligonucleotide was removed by washing the surface with 1 M NaCl. A reference surface was prepared in the same manner without coupling of Tdp1. Compound 70 was diluted into running buffer [10 mM Hepes, 150 mM NaCl, 0.01% tween 20 (v/v), 5% DMSO (v/v) pH 7.5] and injected over all flow cells at 30 µL/min at 25° C. Following compound injections, the surface was regenerated with a 30 second injection 1 M NaCl, a 30 second injection of 50% DMSO (v/v) and a 30 second running buffer injection. Each cycle of compound injection was followed by buffer cycle for referencing purposes. A DMSO calibration curve was included to correct for refractive index mismatches between the running buffer and compound dilution series.

(B) J. Med. Chem. 2013, 56, 182-200

The phospholipases are a heterogeneous family of enzymes that catalyze the hydrolysis of phosphodiester bonds. One member of this family, tyrosyl-DNA-phosphodiesterase I (Tdp1), catalyzes the hydrolysis of 3'-phosphotyrosyl linkers. This enzyme is unique because its catalytic site possesses two histidine and two lysine residues but lacks the aspartate residue that is found in the other members of the family. When DA topoisomerase I (Top1) nicks double-stranded DNA, a covalent Top1-DNA complex is made. The formed 3'-adducts must be removed by Tdp1 in order to repair damaged DNA in stalled Top1-DNA complexes in which the normal DNA religation reaction has not occurred. The enzyme mechanism is believed to occur in two sequential steps. The first step consists of the nucleophilic attack by His263 on the phosphorous atom linked to the oxygen of the Top1 catalytic residue Tyr723 at the 3'-end of DNA (FIG. 2). The function of the Lys265 and Lys495 residues found in the catalytic site is to coordinate the oxygen atoms of the phosphate group, which enables the covalent linkage of His263 to the 3'-phosphate end of the DNA. In the second step, this intermediate is hydrolyzed by a His493-activated water molecule. The overall reaction frees the tyrosine residue and affords a DNA strand that has a 3'-phosphate end. The process of DNA restoration is then finished by DNA polymerases and DNA ligases. The role of Tdp1 is to hydrolyze phosphotyrosyl-DNA linkages in denatured or proteolytically degraded Top1-DNA complexes.

One approach to chemotherapy is based on forming lesions in tumor DNA. Thus, stalled Top1-DNA complexes can also arise when Top1 poisons, such as camptothecins (CPTs) or indenoisoquinolines, are used for cancer therapy. The function of the CPTs is to stabilize the DNA-Top1 complex and inhibit the religation process. As a consequence, DNA replication forks collide with drug-stabilized complexes causing double-stranded DNA breaks that ultimately result in tumor cell death. It is believed that Tdp1 may be responsible for the drug resistance of some cancers by virtue of repairing DNA lesions caused by CPTs. This hypothesis is further supported by the fact that hypersensitivity to CPTs is observed when Tdp1 is inactivated in DNA repair- or checkpoint-deficient yeast.

Given the relationship between Top1 and Tdp1, inhibitors of Tdp1 could potentiate the effects of Top1 poisons. Although the association between these enzymes makes Tdp1 an attractive target for cancer treatment, there are few known inhibitors in the literature. Moreover, these compounds show weak inhibitory activity with $IC_{50}$'s usually in the micromolar range. A recent publication, (A) above, reported that indenoisoquinolines bearing three or four methylene units on the amine-substituted side chain are good Tdp1 inhibitors. The binding interactions between Tdp1 and indenoisoquinoline 1 have previously been characterized using surface plasmon resonance (SPR) and fluorescence resonance energy transfer (FRET). During the previous studies, it was concluded that the sulfonate substituent, key for the activity of compounds such as 2, did not provide any advantage when present on the side chain attached to the lactam of indenoisoquinolines.

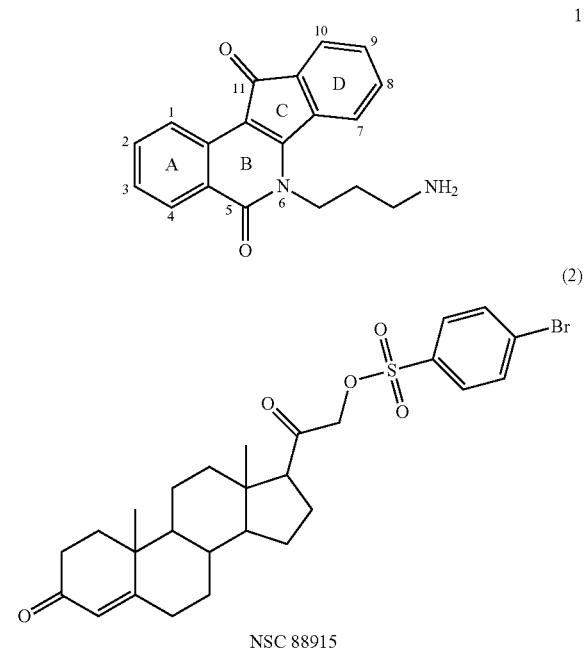

This paper expands the previously reported SAR studies regarding Tdp1 inhibitors and introduces novel indenoisoquinolines that are active against this target. Additionally, compounds with and without dual activity against both Tdp1 and Top1 enzymes are presented.

Chemistry

It is known that the Tdp1 active site possesses two lysine (265 and 495) and two histidine (263 and 493) residues. Some Tdp1 inhibitors have functional groups (e.g. carbonyls) that can hydrogen bond with these residues, and a lipophilic core that interacts with the hydrophobic region (Ala520, Phe259, Gly260, Tyr261, etc.) of the active site. Indenoisoquinolines with an ester moiety might therefore be inhibitors of the enzyme. The partially negatively charged carbonyl oxygen may interact with some of the charged polar residues in the binding pocket while the indenoisoquinoline aromatic system might sit in the hydrophobic portion of the cavity. In order to build on the previous work, an ester moiety was therefore added to 3-amino-6-methyl-5H-indeno[1,2-c]isoquinoline-5,11(6H)-dione (3) as shown in Scheme B1.

Scheme B1ᵃ

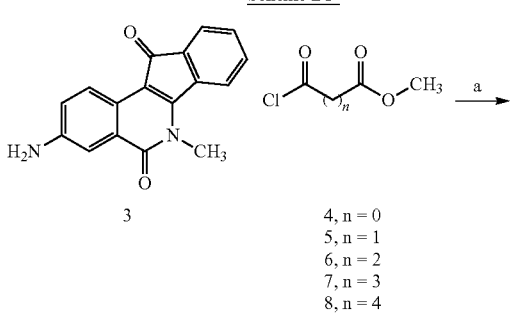

3

4, n = 0
5, n = 1
6, n = 2
7, n = 3
8, n = 4

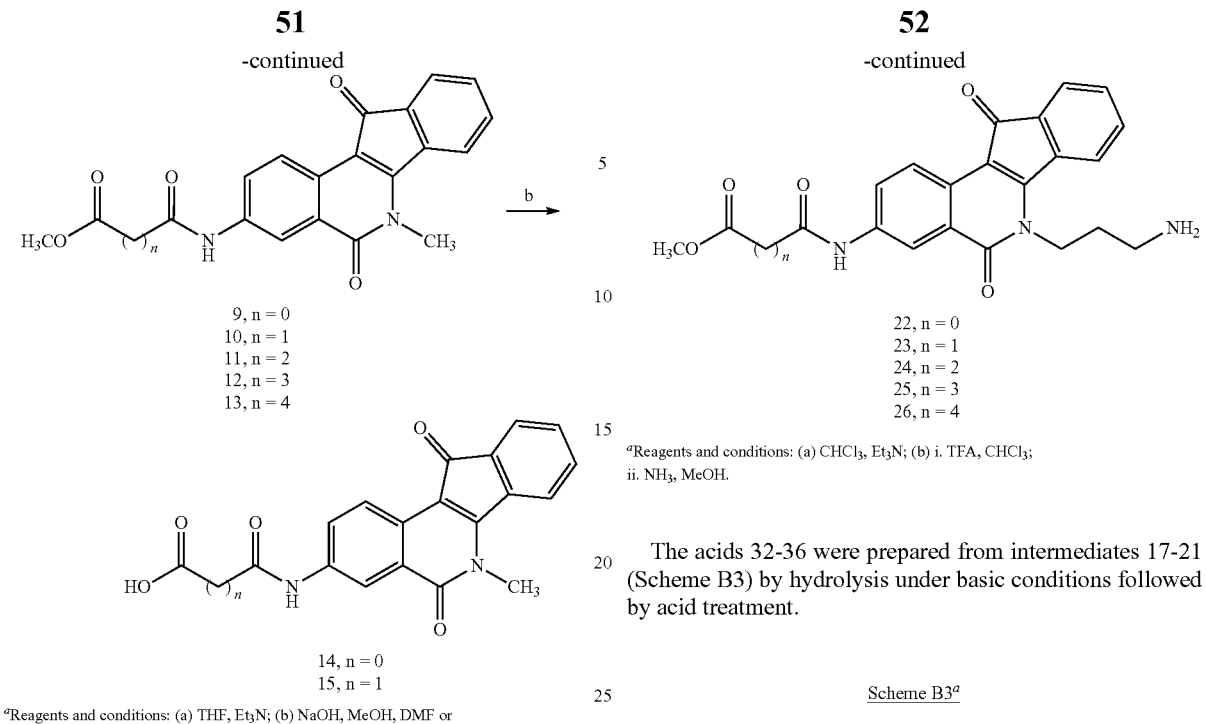

9, n = 0
10, n = 1
11, n = 2
12, n = 3
13, n = 4

14, n = 0
15, n = 1

[a]Reagents and conditions: (a) THF, Et₃N; (b) NaOH, MeOH, DMF or NaOH, EtOH.

Briefly, the amino group of 3 was reacted with methyl oxalyl chloride (4) to provide compound 9 that was hydrolyzed, under basic conditions, to yield 14. Compound 9 was inactive but 14 showed modest Tdp1 inhibitory activity with and IC$_{50}$ of 61.7 μM. Therefore, compounds 5-8 with several methylene units between the acyl chloride and the esters functionalities were reacted with 3 to afford compounds 10-13. The ester 10 was converted to the acid derivative 15.

Compound 16 was reacted with acyl chlorides 4-8 to produce indenoisoquinolines 17-21, which were converted to the amines 22-26 by deprotection under acidic conditions (Scheme B2).

Scheme B2[a]

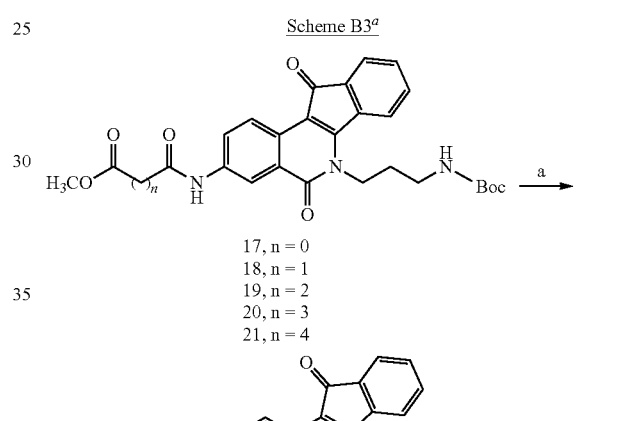

16

17, n = 0
18, n = 1
19, n = 2
20, n = 3
21, n = 4

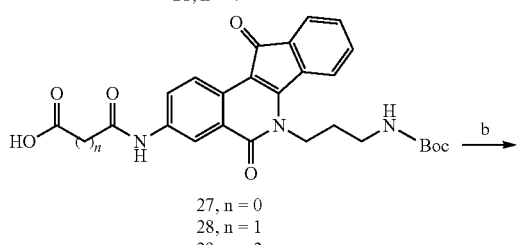

22, n = 0
23, n = 1
24, n = 2
25, n = 3
26, n = 4

[a]Reagents and conditions: (a) CHCl₃, Et₃N; (b) i. TFA, CHCl₃; ii. NH₃, MeOH.

The acids 32-36 were prepared from intermediates 17-21 (Scheme B3) by hydrolysis under basic conditions followed by acid treatment.

Scheme B3[a]

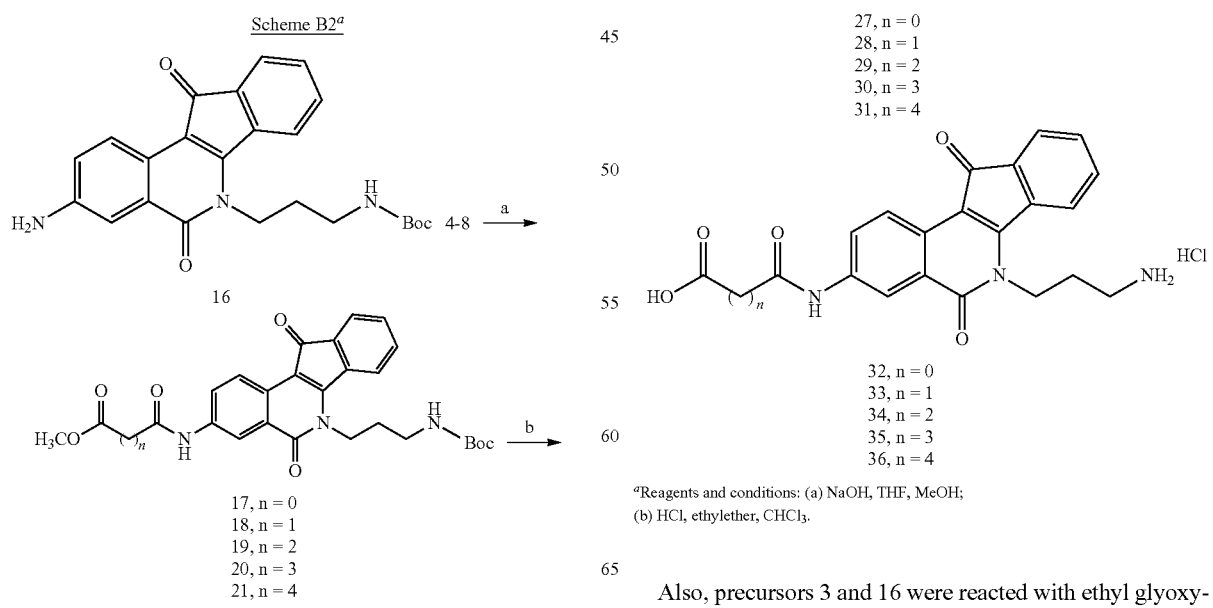

17, n = 0
18, n = 1
19, n = 2
20, n = 3
21, n = 4

27, n = 0
28, n = 1
29, n = 2
30, n = 3
31, n = 4

32, n = 0
33, n = 1
34, n = 2
35, n = 3
36, n = 4

[a]Reagents and conditions: (a) NaOH, THF, MeOH; (b) HCl, ethylether, CHCl₃.

Also, precursors 3 and 16 were reacted with ethyl glyoxylate using the Borch reduction to give esters 38 and 39

(Scheme B4) that were further hydrolyzed to acids 41 and 43. Compound 40 was prepared by deprotection of 39 (Scheme B4).

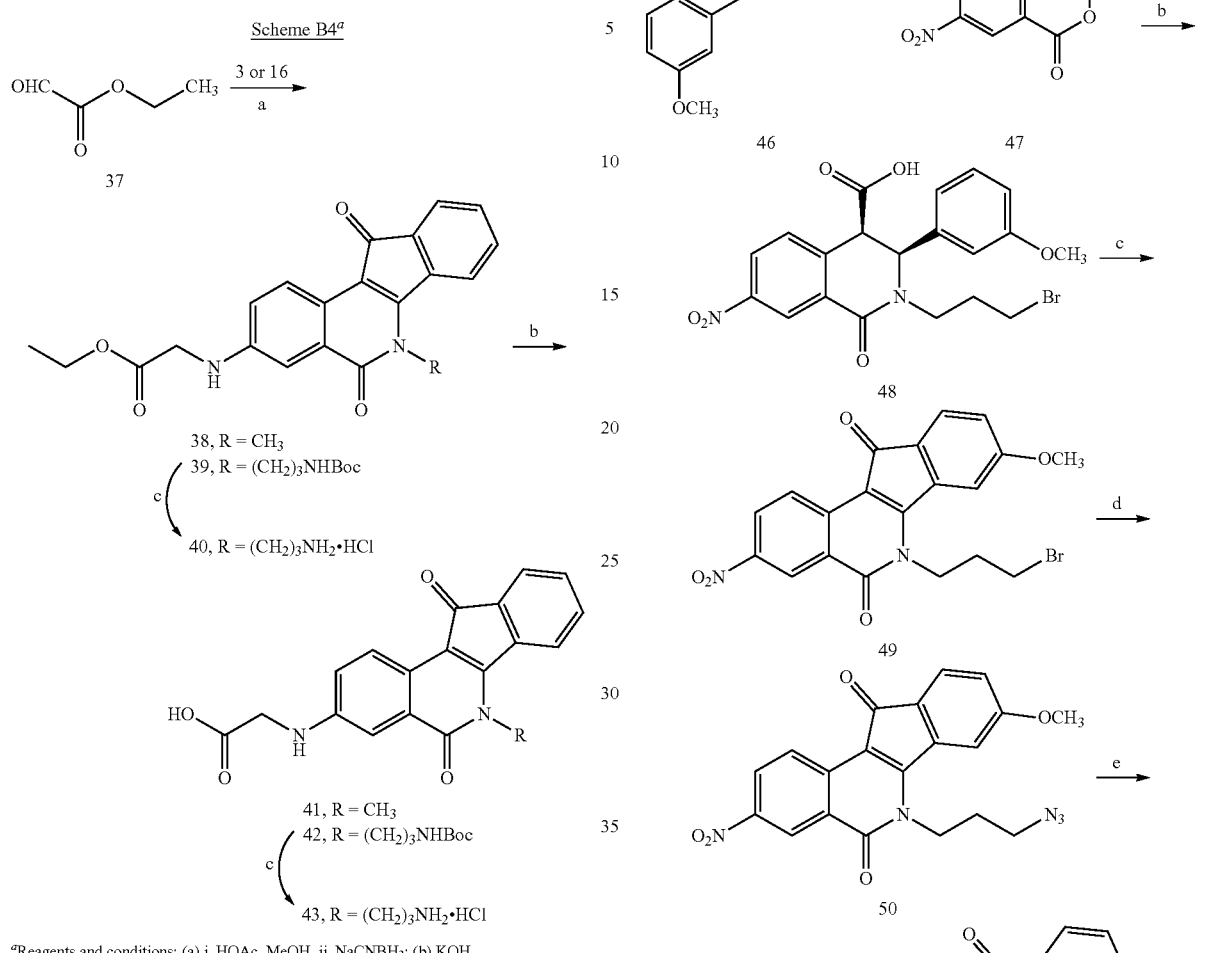

A set of 3-nitroindenoisoquinolines was prepared because a high-priority goal was to synthesize dual Tdp1-Top1 inhibitors, and it is well established that a 3-nitro substituent increases potency vs Top1. Compound 51 (Scheme B5) was prepared using the Schiff base-homophthalic anhydride condensation approach. Briefly, Schiff base 46, obtained by the condensation of meta-methoxybenzaldehyde (44) and 3-bromopropylamine hydrobromide (45), was reacted with 5-nitrohomophthalic anhydride (47) to provide acid 48. This compound was subjected to Friedel-Crafts conditions to afford indenoisoquinoline 49, followed by halide displacement with azide to provide 50. Subsequent reduction of 50 under Staudinger conditions gave indenoisoquinoline 51.

Scheme B5<sup>a</sup>

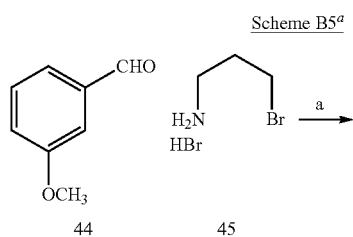

Precursor 49 was treated with imidazole or morpholine to afford compounds 52 and 53 (Scheme B6).

Scheme B6<sup>a</sup>

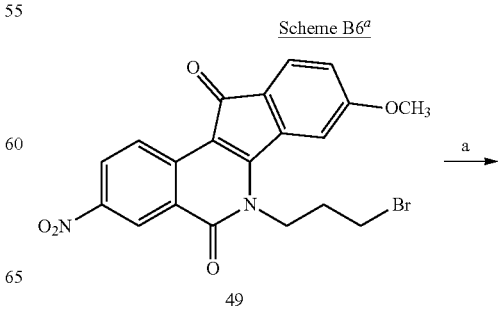

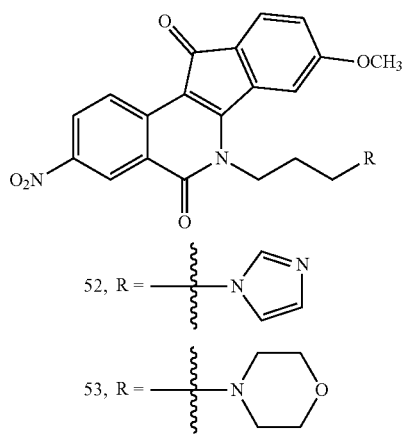

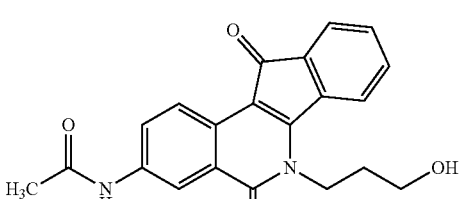

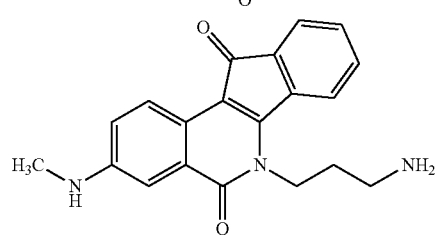

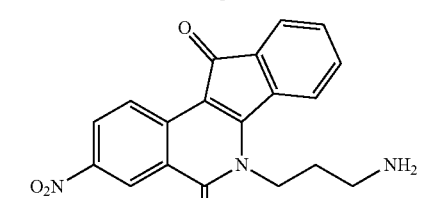

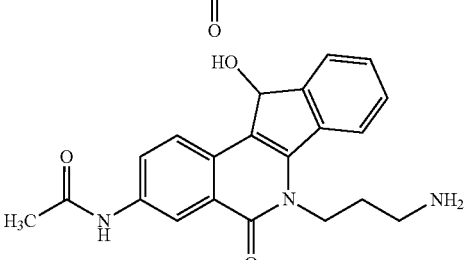

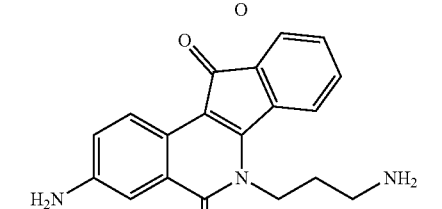

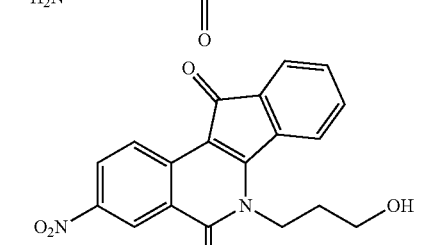

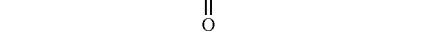

*Reagents and conditions: (a) (i) NaI, dioxane, DMF, (ii) imidazole or morpholine, K₂CO₃.

Previously reported compounds 54-63 from our existing library of compounds prepared to investigate Top1 inhibition, were also evaluated in order to identify key features for Tdp1 inhibitory activity.

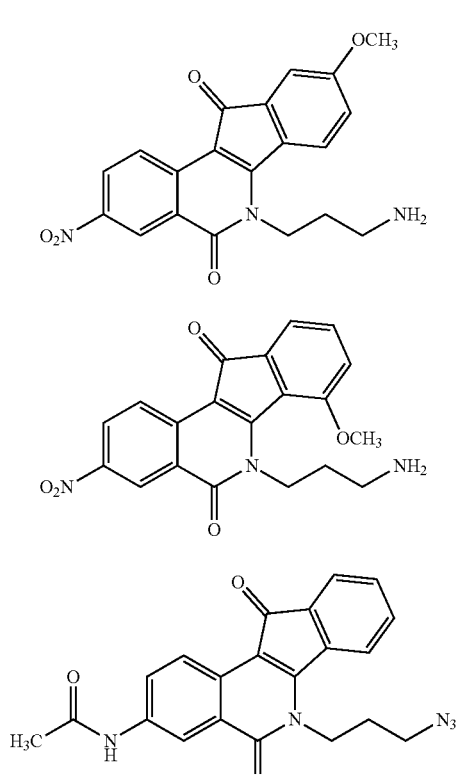

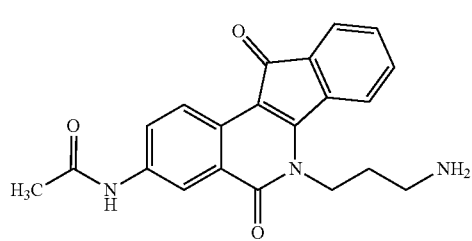

Additionally, new indenoisoquinolines bearing nitrile and iodo substituents on the A ring were synthesized. There are not many substitutions reported in the literature on this side of the indenoisoquinoline system; thus, the current study provided a prime opportunity to expand the substitution pattern on the A ring. Moreover, given the fact that the methoxy or methylenedioxy substituents have been shown to improve Top1 activity, these substituents were added to some of the new compounds. Isochromenone 68 (Scheme B7) was prepared by condensing 6-cyano-3-hydroxyphthalide (66), obtained from 3-cyanophthalide (64), with phthalide (67). The product was reacted with various substituted aminopropyl compounds to yield indenoisoquinolines 72-74 (Scheme B7).

Scheme B7[a]

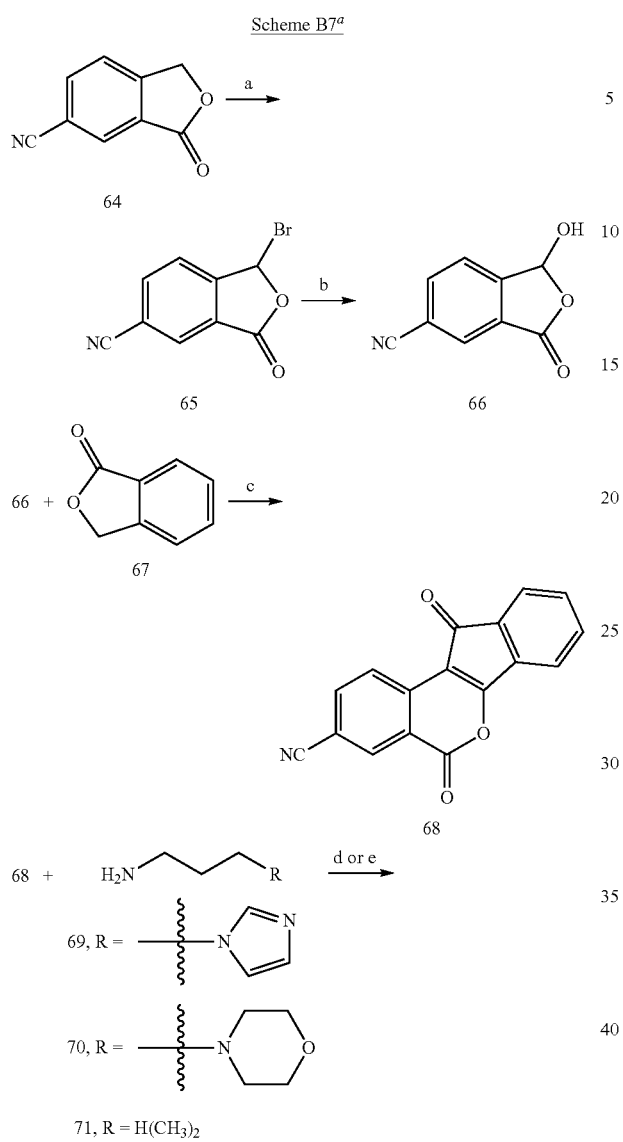

[a]Reagents and conditions: (a) 3-Cl-perBzOH, NBS, hu, CCl₄; (b) H₂O, reflux; (c) (i) NaOMe, MeOH, EtOAc, (ii) HCl, (iii) pTsOH, PhH; (d) THF, Et₃N, reflux; (e) CHCl₃, Et₃N, reflux.

Compound 66 was also condensed with 5,6-methylenedioxyphthalide (75, Scheme B8) to provide the methylenedioxy-substituted compound 76, which was reacted N',N'-dimethylaminopropylamine (71) to yield indenoisoquinoline 77.

Scheme B8[a]

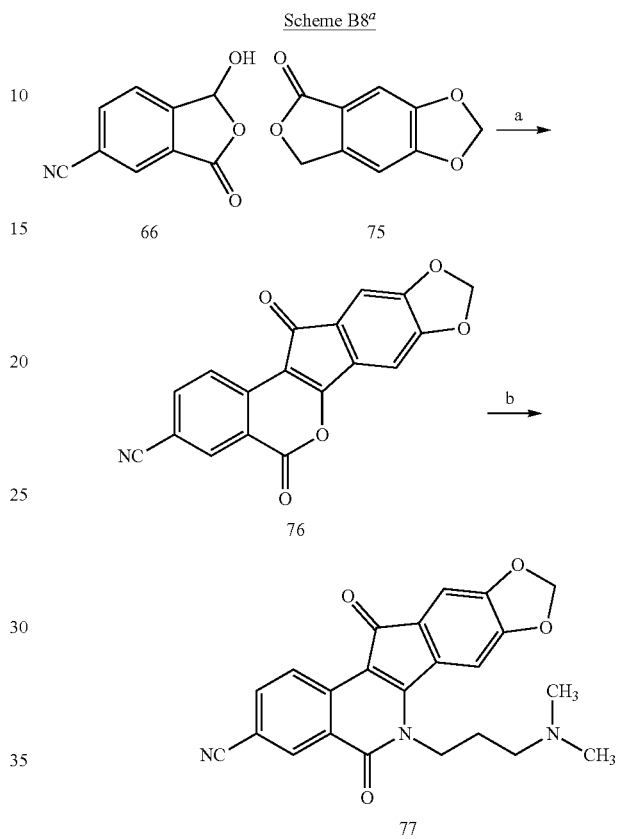

[a]Reagents and conditions: (a) i. NaOMe, MeOH, EtOAc, ii. HCl, iii. PhH, pTsOH; (b) 71, CHCl₃, Et₃N.

Compound 85 (Scheme B9) was prepared according to previous procedures from 5-nitrohomophthalic acid (47) and Schiff base 78. The nitro group of compound 80 was reduced to aniline 81 by catalytic hydrogenation. The amine functionality of compound 81 was replaced by an iodine atom using Sandmeyer chemistry to provide indenoisoquinoline 82, which was converted to the amino analogue 84 by azide displacement and Staudinger reduction. Reaction with formaldehyde under Borch reduction conditions afforded the dimethylamino analogue 85.

Scheme B9[a]

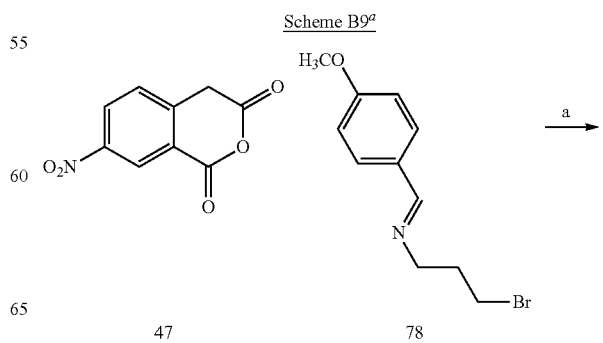

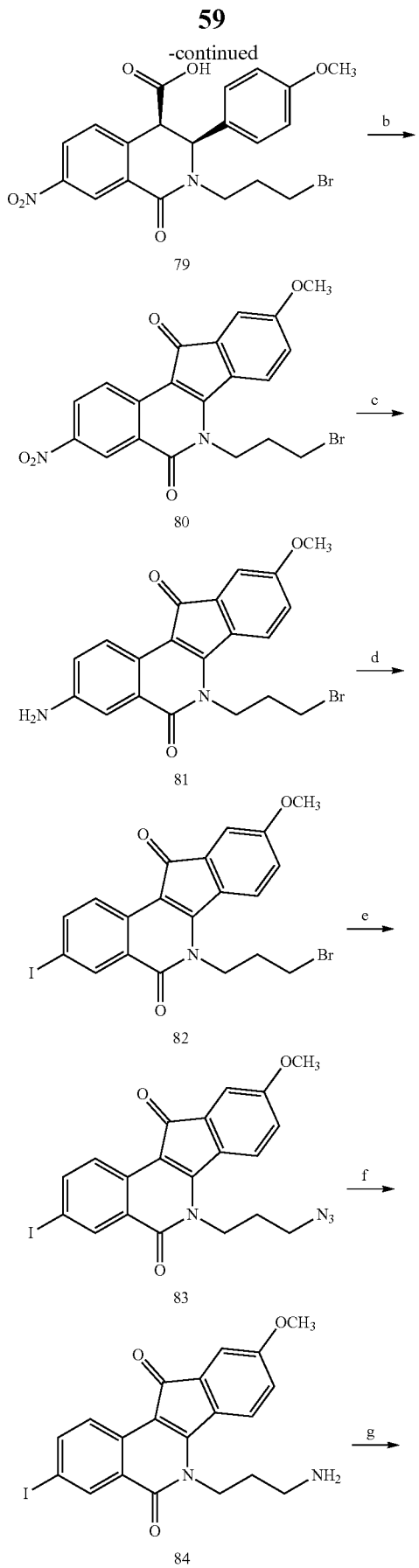

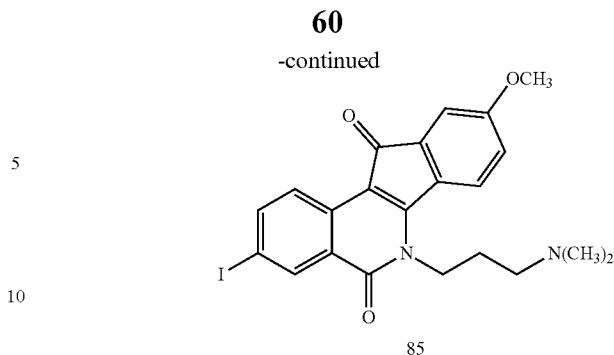

*Reagents and conditions: (a) CHCl₃; (b) (i)SOCl₂, PhH, (ii) AlCl₃, PhNO₂; (c) H₂, Pd—C, THF, MeOH, EtOAc; (d) (i) NaNO₂, HCl, H₂O, dioxane, (ii) CuI, KI, H₂O; (e) NaN₃, DMSO, 90° C.; (f) (i) P(OEt)₃, PhH (ii) HCl, MeOH, (iii) K₂CO₃; (g) (i) CH₂(O), MeOH, HOAc, (ii) NaCNBH₃.

Finally, to expand the diversity of the set, the effect of combining an aniline group at the 3-position with a methoxy group at the 9-position was investigated. In order to accomplish this, compound 86 (Scheme B10) was prepared following published procedures. Reduction of the nitro group of analogue 86 was attempted with several conditions, including Raney nickel as previously done. Ultimately, it was discovered that using comparable amounts (by weight) of 5% Pd—C and indenoisoquinolines 86 while hydrogenating at 1 atm in THF provided the most consistent and reproducible yield of intermediate 87. Treatment of compound 87 with sodium azide in DMSO at 100° C. provided analogue 88, which was subsequently reduced with triethyl phosphite to provide compound 89, isolated as the dihydrochloride salt (Scheme B10).

Scheme B10ᵃ

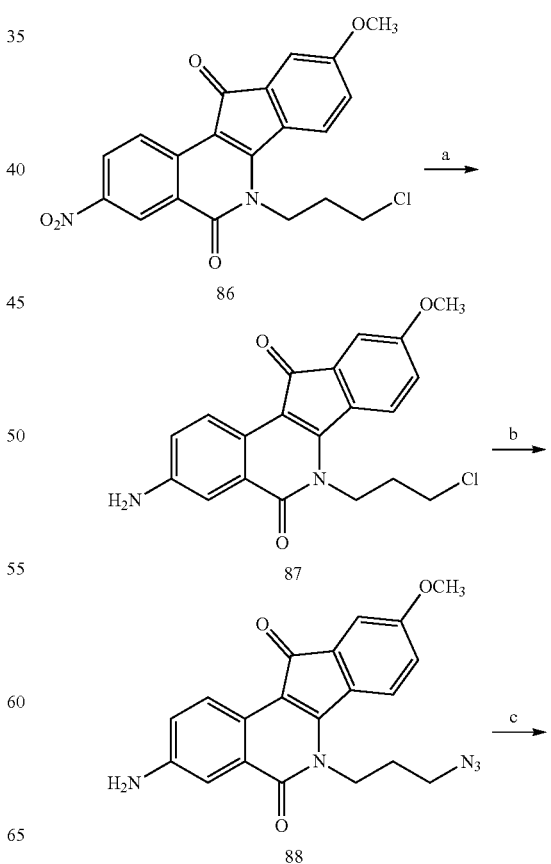

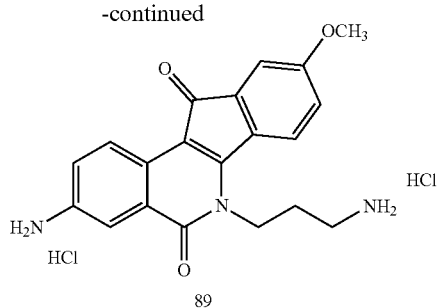

89

[a] Reagents and conditions: (a) Pd—C, H$_2$ (1 atm), THF; (b) NaN$_3$, DMSO, 100° C.; (c) (i) P(OEt)$_3$, PhH, reflux, (ii) HCl, MeOH, reflux.

Biological Results and Discussion

The IC$_{50}$ of the oxalic acid derivative 14 vs Tdp1 was 61±7 μM as shown in the titration curve (FIG. 14). Surface plasmon resonance studies indicated that the compound binds the protein in a 1:1 ratio (FIG. 15). The association and dissociation rates were very fast, but within the limit of detection of the instrument. The experiment also indicated that the compound did not bind to the single-stranded DNA substrate. Based on previous results and the activity of compound 14, computational studies using GOLD and Sybyl were performed. Docking 14 in the catalytic site of Tdp1 suggested interactions between the oxygen atoms of 14 and the Tdp1 residues Thr261, His263, Thr281, Asn283 and Ser400 (FIG. 16). Thus, a series of compounds containing homologous side chains and ester moieties at the 3-position were prepared in order to probe the left side of the binding pocket as it is portrayed in FIG. 16.

TABLE B1

Tdp1 and Top1 Inhibitory Activity

| Compd | Tdp1 | Top1 | Compd | Tdp1[a] | Top1[b] |
|---|---|---|---|---|---|
| 1 | ++ | +++ | 40 | ++(+) | ++(+) |
| 2 | +++ | NT | 41 | 0 | 0 |
| 9 | 0 | 0 | 42 | 0 | 0 |
| 10 | 0 | 0 | 43 | +++ | 0 |
| 11 | 0 | (+) | 49 | 0 | +++ |
| 12 | 0 | + | 50 | 0 | + |
| 13 | 0 | 0 | 51 | ++ | ++ |
| 14 | + | ++ | 52 | (+) | +++ |
| 15 | 0 | +(+) | 53 | 0 | ++ |
| 18 | 0 | 0 | 54 | +++ | ++++ |
| 19 | 0 | 0 | 55 | +++ | ++++ |
| 20 | 0 | 0 | 56 | 0 | ++ |
| 22 | +(+) | 0 | 57 | ++ | 0 |
| 23 | ++(+) | ++(+) | 58 | 0 | + |
| 24 | + | (+) | 59 | + | +(+) |
| 25 | + | 0 | 60 | +(+) | ++(+) |
| 26 | + | (+) | 61 | 0 | 0 |
| 29 | + | (+) | 62 | ++(+) | ++(+) |
| 30 | 0 | 0 | 63 | 0 | ++ |
| 31 | + | (+) | 72 | 0 | ++ |
| 32 | 0 | + | 73 | 0 | ++ |
| 33 | 0 | + | 74 | ++ | +++ |
| 34 | 0 | + | 77 | 0 | ++(+) |
| 35 | 0 | 0 | 84 | +++ | +(+) |
| 36 | 0 | + | 85 | +(+) | +++ |
| 38 | 0 | 0 | 89 | +++ | ++(+) |

[a] Tdp1 IC$_{50}$ was determined by duplicate using a semiquantitative scale: 0, IC$_{50}$ >111 μM; +, IC$_{50}$ between 37-111 μM; ++, IC$_{50}$ between 12-37 μM; +++, IC$_{50}$ between 1-12 μM; ++++, IC$_{50}$ <1 μM.
Active compounds were further evaluated for a more accurate value.
[b] Compound-induced DNA cleavage due to Top1 inhibition is graded by the following semiquantitative scale relative to 1 μM camptothecin (90) or MJ-III-65 (91): 0, no detectable activity; +, weak activity; ++, similar activity to compound 91; +++, greater activity than 91; ++++, equipotent to 90.
The (+) ranking indicates the activity lies between two given values.
NT: not tested.

TABLE B2

IC$_{50}$ Values of Tdp1 Active Compounds

| Compd | Tdp1 (μM) |
|---|---|
| 14 | 61 ± 7 |
| 22 | 45 ± 10 |
| 23 | 18 ± 8 |
| 40 | 11 ± 5 |
| 43 | 5.0 ± 1.4 |
| 51 | 15 ± 3 |
| 54 | 11 ± 1 |
| 55 | 5.8 ± 0.8 |
| 57 | 18 ± 1 |
| 62 | 12 ± 4 |
| 84 | 5.2 ± 0.1 |
| 89 | 6.7 ± 0.8 |

The IC$_{50}$ values of Tdp1 active compounds were determined by quadruplicate

An analysis of the biological data for the rest of the indenoisoquinolines allowed the determination of some of the important features needed for Tdp1 inhibitory activity. The aminopropyl side chain is clearly important for enzyme inhibition as observed in 22, +(+); 23, ++(+); 40, ++(+); 43, +++; 51, ++; 54, +++; 55, +++; 57, ++; 60, +(+); 62, ++(+); 74, ++; 84, +++; 85, +(+); and 89, +++; (note: the "+ system" is a semiquantitative scale expressing IC$_{50}$ values at a given range as explained in Table B1, and the IC$_{50}$ values of the more active Tdp1 inhibitors are reported in Table B2). The indenoisoquinoline 40 was chosen as a representative example of an N-(3-aminopropyl) compound for GOLD docking and molecular mechanics energy minimization studies, which resulted in the hypothetical binding mode displayed in FIG. 17. The structure suggests the existence of bonding interactions between the charged ammonium cation of the ligand and the Val401 backbone carbonyl, the Pro461 backbone carbonyl, and the Thr466 side chain oxygen with distances of 2.7 Å, 2.6 Å and 3.0 Å, respectively. These bonding interactions would help to explain the Tdp1 inhibitory activity of the 3-aminopropyl-substituted compounds 40 and 43 vs the inactivity of their N-methylated and Boc-protected counterparts 38, 41, and 42. Additionally, Thr261 with its side chain hydroxyl was within H-bonding distance, 2.7 Å, to the carbonyl oxygen of the ligand 40.

In general, compounds in which the aminopropyl side chain was Boc-protected were either inactive or had very low Tdp1 inhibitory activity (Table B1). The weakly active Boc-protected compounds were 29 and 31. One N-methylated compound 14 showed weak activity, +, but all of the other analogues containing an N-methyl side chain (9-13, 15, 38, and 41) were inactive. Molecules 15, 30, and 32-36 with an acidic side chain at C-3 on the A ring were inactive but compounds 14 (+) and 43 (+++) were the exceptions. The ester-substituted indenoisoquinolines containing an aminopropyl side chain were all active but the activity decreased when more methylene units were added to the ester side chain, going from +(+) and ++(+) for 22 and 23 to + for 24-26 (Table B1). The ethyl ester 40, which has a short ester side chain, was active.

Given the apparent importance of the aminopropyl side chain for Tdp1 inhibition, ten compounds 54-63, see above, from our existing Top1 inhibitor library were selected for testing in order to further explore this feature. These compounds were all active as long as the 3-aminopropyl side chain and the 11-keto functional group were both present. Replacement of the primary amine with bromide, azide, morpholine or imidazole rendered the compounds very weak or inactive, as exemplified by 49, 50, 52, and 53 (Table B1). The primary alcohols 58 and 63 were also inactive, indicating that a primary ammonium ion may be a critical feature that is important for activity as opposed to hydrogen bonding capabilities per se. Compounds 59 and 62, with hydrogen bond acceptors at the 3-position of the A ring, are also Tdp1 inhibitors. It seems that the Tdp1 inhibitory activity of the compounds decreases as the electron withdrawing strength of the substituent at the 3 position increases, as seen with the $IC_{50}$'s of compounds 60>57>62, which are >37, 18 and 12 μM, respectively. Compounds 72-74 support the trend that a nitrogen that is more basic than morpholine or imidazole on the aminopropyl side chain is necessary for Tdp1 inhibitory activity. The primary amine 84, +++, was more active than the tertiary amine 85, +(+), suggesting a steric limitation to binding that may also be operating in the 72-74 series.

Molecular modeling indicates that the carbonyl of the five-membered C ring or the amide-carbonyl of the B ring may interact with either the Ser400 or Thr261 side chain hydroxyl groups as seen in FIG. 16 and FIG. 17. In the case of 14, the lactam carbonyl binds Thr261, whereas in 40, the ketone binds, so the ring systems are "flipped" relative to each other. This suggests that the amino group of the ligand 40 and other N-(3-aminopropyl)-indenoisoquinolines can play a major role in orienting the ligand in the binding site of the enzyme.

Compound 61, which contains a hydroxyl group instead of the ketone, was not active, suggesting that a hydrogen bond-accepting carbonyl oxygen is important for activity. The presence of a 9-methoxy group on the D ring of the indenoisoquinolines seems to have a positive effect on the Tdp1 inhibitory activity, as observed for 54 (+++) vs 60+(+) or 89 (+++) vs 62++(+). Also, the position of the methoxy group at C7, C8, or C9 affects the $IC_{50}$'s as seen with 51 (15 μM), 54 (11 μM) and 55 (5.8 FIG. 18 shows a representative gel electrophoresis assay and titration curves for determination of Tdp1 $IC_{50}$ values for compounds 54 and 55. The 9-methoxy substituent seems to play a bigger role in Tdp1 inhibitory activity than the substituent at the 3-position. Within the 9-methoxy indenoisoquinolines, the electron-withdrawing 3-nitro group decreases the activity slightly when compared with its 3-iodo or 3-amino counterparts. The $IC_{50}$'s of the active compounds 54 (3-$NO_2$), 84 (3-I), and 89 (3-$NH_2$) are 11±1, 5.2±0.1, 6.7±0.8 (Table B2), respectively. Compound 77, which contains an 8,9-methylenedioxy group, was inactive vs Tdp1.

The Top1 inhibitory activities of some of the active compounds have previously been analyzed and published. Regarding the new compounds, 49-53 were less active compared with 54 and 55. For example, compounds 52 and 53 present Top1 inhibitory activities of +++ and ++, respectively, compared to ++++ observed for both 54 and 55. The 3-cyano-substituted compounds 72-74 showed Top1 inhibitory activities of ++, ++, and +++, respectively. The 3-cyano compound 77 had good Top1 activity of ++(+).

The iodo-substituted compounds 84 and 85 were also active as Top1 inhibitors, although not as active as the previously published analogues such as 54 having a 3-nitro substituent. However, the 3-iodo substituent could be easily exchanged, thus expanding the alternatives for substitution. When the nitro group of compound 54 was replaced with an amine to obtain 89, the Top1 inhibitory activity dropped from ++++ to ++. The addition of a methoxy group at the 9 position of compound 60 increased Top1 inhibitory activity as seen with 54 (++++) vs 60 [++(+)]. However, this trend is not observed with the aniline analogues as seen in 62 with an activity of ++(+) vs 89 with an activity of ++(+).

All of the compounds were tested for induction of Top1-DNA cleavage complexes that are stabilized by inhibition of the DNA religation reaction due to intercalation of the drugs between DNA base pairs (FIG. 19). Camptothecin (90) and the previously synthesized lead compound 91 were included for comparison. The cleavage complexes were

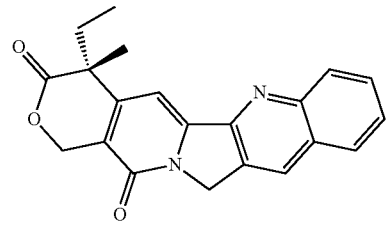

90

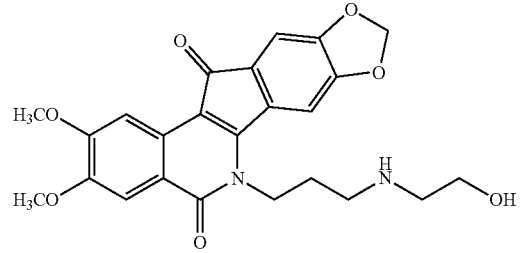

91 monitored using a $^{32}P$ 3'-end labeled, 117-bp DNA fragment that was reacted with recombinant human Top1 in the presence of increasing concentrations of the indenoisoquinolines while separation of the DNA fragments was carried out on a denaturing gel. The sequence preferences for trapping the Top1-DNA cleavage complexes by the indenoisoquinolines are similar to each other, but the pattern is different from camptothecin, indicating that the indenoisoquinolines target the genome differently from camptothecin. However, the indenoisoquinolines 52, 77, and 85 differ from each other in their abilities to suppress DNA cleavage at high drug concentrations. As is evident from the gel, the indenoisoquinolines 52 and 77, having terminal dimethylamino substituents on the side chain, suppress DNA cleavage at a high concentration of 100 μM, but compound 52, having an imidazole substituent at the end of the chain, does not. DNA unwinding studies on similar 7-azaindenoisoquinolines have shown that compounds with an N-(3-dimethylaminopropyl) substituent intercalate into free DNA at high drug concentrations, making the DNA a poorer substrate for Top1, but compounds with an N-(3-imidazolylpropyl) substituent do not intercalate into free DNA; so DNA cleavage is not suppressed at high drug concentration. Although slight suppression is evident at high concentrations of the imidazole analogue 52, it does not resemble the complete suppression observed with the dimethylamino analogues 77 and 85.

TABLE B3

Cytotoxicities of Selected Compounds

| Cpd | lung HOP-62 | colon HCT-116 | CNS SF-539 | melanoma UACC-62 | ovarian OVCAR-3 | renal SN12 C | prostate DU-145 | breast MDA-MB-435 | MGM (μM)[b] |
|---|---|---|---|---|---|---|---|---|---|
| | | | | Cytotoxicity ($GI_{50}$ in μM)[a] | | | | | |
| 22 | 0.65 | 0.57 | 6.90 | 1.22 | 4.01 | 2.53 | 1.11 | 3.36 | 1.86 ± 0.38[c] |
| 23 | 1.56 | 0.54 | 4.03 | 1.69 | 3.22 | 1.46 | 1.57 | 2.33 | 1.86 |
| 25 | 0.79 | 0.38 | 1.47 | 1.22 | 1.47 | 1.02 | 0.54 | 2.05 | 1.09 |

TABLE B3-continued

Cytotoxicities of Selected Compounds

| | Cytotoxicity (GI$_{50}$ in μM)[a] | | | | | | | | |
|---|---|---|---|---|---|---|---|---|---|
| Cpd | lung HOP-62 | colon HCT-116 | CNS SF-539 | melanoma UACC-62 | ovarian OVCAR-3 | renal SN12 C | prostate DU-145 | breast MDA-MB-435 | MGM (μM)[b] |
| 26 | 2.32 | 0.51 | 5.65 | 2.43 | 3.52 | 1.82 | 0.77 | 4.3 | 2.34 |
| 40 | 0.93 | 0.44 | 8.91 | 2.25 | 3.12 | 1.75 | 1.68 | 3.05 | 1.69 |
| 43 | 0.65 | 0.33 | 1.79 | 0.72 | 1.6 | 0.49 | 1.51 | 1.14 | 0.87 ± 0.014 |
| 51 | 0.14 | 0.06 | 0.61 | 0.14 | 0.54 | 0.15 | 0.18 | 0.58 | 0.17 ± 0.017 |
| 52 | <0.01 | <0.01 | <0.01 | <0.01 | 0.03 | <0.01 | <0.01 | 0.03 | 0.02 ± 0.0006 |
| 54 | <0.01 | <0.01 | <0.01 | <0.01 | 2.82 | <0.01 | — | 3.31 | 0.02 ± 0.0008 |
| 55 | 1.15 | 0.72 | 1.45 | 2.34 | 2.29 | 7.08 | 1.07 | 1.62 | 1.41 ± 0.43 |
| 60 | — | <0.01 | 0.14 | 0.03 | 0.08 | <0.01 | 0.01 | 0.12 | 0.15 ± 0.10 |
| 62 | 0.27 | 0.18 | 0.34 | 0.30 | 0.13 | 0.23 | 0.12 | 0.23 | 0.16 |
| 63 | 0.39 | 0.19 | 0.39 | 0.31 | 0.87 | 0.47 | 0.43 | 1.97 | 0.89 ± 0.22 |
| 74 | 0.26 | 0.05 | 1.12 | 0.19 | 1.72 | 0.19 | 0.24 | 0.62 | 0.30 ± 0.014 |
| 84 | 0.14 | 0.07 | 0.39 | 0.14 | 1.32 | 0.05 | 0.05 | 0.96 | 0.25 ± 0.004 |
| 89 | <0.01 | <0.01 | 0.03 | 0.10 | 0.02 | <0.01 | <0.01 | 0.12 | 0.04 |

[a] The cytotoxicity GI$_{50}$ values are the concentrations corresponding to 50% growth inhibition. The compounds were tested at concentrations ranging up to 10 μM.
[b] Mean graph midpoint for growth inhibition of all human cancer cell lines successfully tested.
[c] For MGM GI$_{50}$ values in which a standard error appears, the GI$_{50}$ values for individual cell lines are the average of two determinations; values without standard error are from one determination.

In order to investigate their potential as anticancer agents, a set of indenoisoquinolines was examined for antiproliferative activity against the human cancer cell lines in the National Cancer Institute screen, in which the activity of each compound was evaluated with approximately 55 different cancer cell lines of diverse tumor origins. The GI$_{50}$ values obtained with selected cell lines, along with the mean graph midpoint (MGM) values, are summarized in Table B3, above. The MGM is based on a calculation of the average GI$_{50}$ for all of the cell lines tested in which GI$_{50}$ values below and above the test range ($10^{-8}$ to $10^4$ molar) are taken as the minimum ($10^{-8}$ molar) and maximum ($10^{-4}$ molar) drug concentrations used in the screening test. For comparison purposes, the activities of previously reported compounds 54-63 are included on the Table B3. Many of the new compounds display significant potencies against various cell lines with GI$_{50}$'s in the low micromolar or submicromolar range. All of the compounds in Table B3 except 22, 25, 43, and 63 display some degree of inhibitory activity against both Tdp1 and Top1. The most promising new compounds are 52 and 89, with mean-graph midpoint (MGM) GI$_{50}$ values of 0.02 μM and 0.04 μM, respectively. Overall, the cytotoxicities do not correlate very well with the potencies vs the isolated enzymes. For example, compounds 23, 40, and 62 all have the same++(+) potencies vs both enzymes, but their cytotoxicity MGM values range from 1.86 to 0.16 μM. Another example would be 54 (MCM 0.02 μM) vs 55 (MGM 1.41 μM), both of which have +++ potency vs Tdp1 and ++++ potency vs Top1. Compounds 52 (MGM 0.02 μM) and 54 (MGM 0.02 μM) provide another way of stating the case, since they both have the same MGM value but on the basis of the Tdp1 and Top1 inhibitory potencies, 54 would be expected to be more cytotoxic than 52. These differences in cytotoxicities may reflect different uptake, distribution, metabolism, and excretion profiles in the cellular systems as well as off-target effects.

Experimental Section

Methyl 2-[(6-Methyl-5,11-dioxo-6,11-dihydro-5H-indeno[1,2-c]isoquinolin-3-yl)amino]-2-oxoacetate (9)

3-Amino-6-methyl-5H-indeno[1,2-c]isoquinoline-5,11 (6H)-dione (3, 100 mg, 0.36 mmol) was dissolved in tetrahydrofuran (10 mL) and the reaction mixture cooled to 0° C. Methyl 2-chloro-2-oxoacetate (4, 0.1 mL, 1.09 mmol) was added dropwise to the indenoisoquinoline solution and the reaction mixture was stirred for 30 min. Triethylamine (0.1 mL) was slowly added and the reaction mixture was stirred for another 30 min, keeping the temperature at 0° C. The reaction mixture was diluted with water (30 mL) and chloroform (20 mL) was added. The organic phase was separated and washed with water (30 mL) and brine (30 mL). The organic phase was concentrated and the compound purified by silica gel column chromatography, eluting with chloroform-methanol, 50:1. The product was obtained as a brick-red solid (53 mg, 39%): mp 287-289° C. IR (Film) 3336, 1642, 1514, 1480, 1406, 1358, 1333, 1231, 1045, 815, 759 cm$^{-1}$; $^1$H NMR (300 MHz, CDCl$_3$) δ 11.08 (s, 1H), 8.67 (d, J=1.9 Hz, 1H), 8.40 (d, J=8.7 Hz, 1H), 8.06 (dd, J=8.8 Hz, J=2.1 Hz, 1H), 7.82 (d, J=7.2 Hz, 1H), 7.50-7.43 (m, 3H), 3.93 (s, 3H), 3.87 (s, 3H); ESIMS m/z (rel intensity) 363 (MH$^+$, 100); HRESIMS calcd for C$_{20}$H$_{14}$N$_2$O$_5$ 363.0910 (MH$^+$). found 363.0907 (MH$^+$); HPLC purity: 98.3% (MeOH—H$_2$O, 90:10), 95.2% (MeOH—H$_2$O, 85:15).

Methyl 3-[(6-Methyl-5,11-dioxo-6,11-dihydro-5H-indeno[1,2-c]isoquinolin-3-yl)amino]-3-oxopropanoate (10)

3-Amino-6-methyl-5H-indeno[1,2-c]isoquinoline-5,11 (6H)-dione (3, 150 mg, 0.54 mmol) was dissolved in tetrahydrofuran (20 mL) and the solution was cooled to 0° C. Methyl malonyl chloride (5, 0.1 mL, 0.93 mmol) was added and the reaction mixture was stirred for 5 min at 0° C. Triethylamine (0.2 mL) was added and the reaction mixture was stirred for 2 h at 0° C. The solvent was removed under vacuum and the residue was purified by silica gel column chromatography, eluting with chloroform-methanol, 95:5, and then chloroform-ethyl acetate-methanol, 45:45:10. The fractions were combined, the solvent was removed under vacuum and the solid was washed with hexane-dichloromethane, 1:1 (25 mL). The product was obtained as a reddish-brown solid (60 mg, 29%): mp 230° C. (dec). IR (Film) 3309, 3071, 2952, 1744, 1692, 1661, 1574, 1531, 1317, 1276, 1054, 1017, 901 cm$^{-1}$; $^1$H NMR (300 MHz, DMSO-d$_6$) δ 10.46 (s, 1H), 8.42

(d, J=1.8 Hz, 1H), 8.31 (d, J=8.8 Hz, 1H), 7.79 (dd, J=8.8 Hz, J=2.0 Hz, 1H), 7.72 (d, J=7.4 Hz, 1H) 7.45-7.37 (m, 3H), 3.85 (s, 3H), 3.66 (s, 3H), 3.49 (s, 2H); $^{13}$C NMR (125 MHz, DMSO-$d_6$) δ 190.3, 168.4, 164.6, 162.5, 156.0, 137.9, 137.7, 134.6, 133.9, 131.3, 127.8, 125.8, 124.3, 123.7, 122.8, 117.2, 107.0, 52.4, 43.8, 32.5; ESIMS m/z (rel intensity) 775 (2MNa$^+$, 100), 752 (2MH$^+$, 37), 377 (MH$^+$, 10); HRESIMS calcd for $C_{21}H_{16}N_2O_5$ 377.1137 (MH$^+$). found 377.1140 (MH$^+$); HPLC purity: 95.0% (75:25), 95.0% (MeOH—$H_2O$, 70:30).

General Procedure for the Synthesis of Indenoisoquinolines 11-13

3-Amino-6-methyl-5H-indeno[1,2-c]isoquinoline-5,11 (6H)-dione (3, 160 mg, 0.58 mmol) was dissolved in tetrahydrofuran (15 mL) and the reaction mixture cooled to 0° C. The desired acyl chloride (6-8, 100-125 μL, 0.81 mmol) was added dropwise to the indenoisoquinoline solution and the reaction mixture was stirred for 10 min. Triethylamine (0.4 mL) was slowly added and the reaction mixture was stirred for 1 h, keeping the temperature at 0° C. Chloroform (40 mL) was added to the reaction mixture and the organic solution was washed with water (3×40 mL) and brine (1×50 mL). The organic phase was concentrated and the compounds purified by silica gel column chromatography.

Methyl 4-[(6-Methyl-5,11-dioxo-6,11-dihydro-5H-indeno[1,2-c]isoquinolin-3-yl)amino]-4-oxobutanoate (11)

The compound was eluted with chloroform-methanol, 20:1. The product was obtained as an orange solid (101 mg, 44%): mp 250-252° C. IR (Film) 3339, 3314, 2951, 1735, 1720, 1688, 1658, 1643, 1573, 1518, 1432, 1315, 1195, 1157, 1055, 891, 845, 763, 700 cm$^{-1}$; $^1$H NMR (500 MHz, DMSO-$d_6$) δ 10.37 (s, 1H), 8.49 (d, J=1.9 Hz, 1H), 8.35 (d, J=8.7 Hz, 1H), 7.87 (dd, J=8.7 Hz, J=2.1 Hz, 1H), 7.78 (d, J=7.5 Hz, 1H) 7.49-7.37 (m, 3H), 3.89 (s, 3H), 3.57 (s, 3H), 2.61 (m, 4H); $^{13}$C NMR (125 MHz, DMSO-$d_6$) δ 190.9, 173.8, 171.0, 163.1, 156.3, 139.0, 138.3, 135.1, 134.5, 131.8, 127.9, 126.3, 124.8, 124.3, 124.1, 123.3, 117.4, 107.6, 52.3, 33.0, 31.8, 29.3; ESIMS m/z (rel intensity) 413 (MNa$^+$, 100); HRESIMS calcd for $C_{22}H_{18}N_2O_5$ 413.1113 (MNa$^+$). found 413.1119 (MNa$^+$); HPLC purity: 98.7% (MeOH—$H_2O$, 85:15), 98.8% (MeOH—$H_2O$, 95:5).

Methyl 5-[(6-Methyl-5,11-dioxo-6,11-dihydro-5H-indeno[1,2-c]isoquinolin-3-yl)amino]-5-oxopentanoate (12)

The compound was eluted with chloroform-methanol, 30:1. The product was obtained as a dark red solid (225 mg, 96%): mp 184-186° C. IR (Film) 3335, 3119, 2945, 1730, 1689, 1650, 1580, 1525, 1431, 1316, 1274, 1194, 901, 844, 757, 718 cm$^{-1}$; $^1$H NMR (500 MHz, DMSO-$d_6$) δ 10.35 (s, 1H), 8.49 (d, J=1.9 Hz, 1H), 8.35 (d, J=8.7 Hz, 1H), 7.85 (dd, J=8.7 Hz, J=2.1 Hz, 1H), 7.76 (d, J=7.5 Hz, 1H) 7.45-7.32 (m, 3H), 3.88 (s, 3H), 3.56 (s, 3H), 2.46 (m, 4H), 1.81 (m, 2H); $^{13}$C NMR (125 MHz, DMSO-$d_6$) δ 190.3, 173.4, 171.2, 162.5, 155.6, 138.3, 137.7, 134.5, 133.8, 131.2, 127.3, 125.8, 124.2, 123.7, 123.5, 122.7, 119.6, 107.0, 51.6, 35.6, 32.9, 32.4, 20.6; ESIMS m/z (rel intensity) 405 (MH$^+$, 100); HRESIMS calcd for $C_{23}H_{20}N_2O_5$ 405.1450 (MH$^+$). found 405.1446 (MH$^+$); HPLC purity: 96.0% (MeOH—$H_2O$, 80:20).

Methyl 6-[(6-Methyl-5,11-dioxo-6,11-dihydro-5H-indeno[1,2-c]isoquinolin-3-yl)amino]-6-oxohexanoate (13)

The compound was eluted with chloroform-methanol, 30:1. The product was obtained as a red solid (221 mg, 91.2%): mp 177-179° C. IR (Film) 3341, 3071, 2950, 2868, 1732, 1692, 1659, 1573, 1522, 1512, 1434, 1316, 1276, 1196, 1055, 902, 842, 762, 750 cm$^{-1}$; $^1$H NMR (500 MHz, DMSO-$d_6$) δ 10.20 (s, 1H), 8.49 (d, J=2.0 Hz, 1H), 8.36 (d, J=8.8 Hz, 1H), 7.88 (dd, J=8.7 Hz, J=2.0 Hz, 1H), 7.79 (d, J=7.5 Hz, 1H) 7.51-7.36 (m, 3H), 3.91 (s, 3H), 3.55 (s, 3H), 2.31 (m, 4H), 1.56 (m, 4H); $^{13}$C NMR (125 MHz, DMSO-$d_6$) δ 190.3, 173.6, 171.6, 162.5, 155.8, 138.5, 137.7, 134.6, 133.9, 131.2, 127.3, 125.9, 124.2, 123.7, 123.5, 122.8, 117.0, 107.1, 51.6, 36.4, 33.4, 32.5, 24.8, 24.4; ESIMS (rel intensity) m/z 419 (MH$^+$, 100); HRESIMS calcd for $C_{24}H_{22}N_2O_5$ 419.1607 (MH$^+$). found 419.1613 (MH$^+$); HPLC purity: 97.0% (MeOH—$H_2O$, 85:15), 96.9% (MeOH—$H_2O$, 90:10).

(6-Methyl-5,11-dioxo-6,11-dihydro-5H-indeno[1,2-c]isoquinolin-3-yl)-carbamic Acid (14)

3-Amino-6-methyl-5H-indeno[1,2-c]isoquinoline-5,11 (6H)-dione (3, 201 mg, 0.72 mmol) was dissolved in tetrahydrofuran (30 mL) and cooled to 0° C. Methyl oxalyl chloride (4, 0.1 mL, 1.16 mmol) and triethylamine (0.2 mL) were added dropwise and the reaction mixture was stirred for 2 h at 0° C. The reaction mixture was diluted with water (100 mL) and extracted with chloroform (4×50 mL). The solvent was removed under vacuum and the compound passed through a short silica gel column chromatography, eluting with chloroform-methanol, 9:1. The impure solid, compound 9, was dissolved in a solution of sodium hydroxide (0.1 g, 2.5 mmol) in ethanol (50 mL) and water (1 mL) and the reaction mixture was stirred overnight at room temperature. The solvent was removed under vacuum and the residue purified by silica gel column chromatography, eluting with chloroform-methanol-acetic acid, 90:9:1. Compound 14 was obtained as a reddish-brown solid (103 mg, 44.7%, after 2 steps): mp 360° C. (dec). IR (Film) 3325, 2928, 1692, 1657, 1600, 1580, 1533, 1435, 1319, 1197, 903, 701 cm$^{-1}$; $^1$H NMR (300 MHz, DMSO-$d_6$) δ 10.9 (s, 1H), 8.70 (s, 1H), 8.35 (d, J=8.2 Hz, 1H), 8.02 (s, 1H), 7.90 (br s, 1H), 7.45 (m, 3H), 3.89 (s, 3H); $^{13}$C NMR (125 MHz, DMSO-$d_6$) δ 190.1, 162.4, 162.2, 157.9, 156.3, 137.5, 136.9, 134.6, 134.0, 131.4, 128.4, 126.9, 124.4, 123.5, 123.4, 122.8, 118.5, 106.9; ESIMS m/z (rel intensity) 347 [(M-H$^+$)$^-$]; negative ion; HRESIMS calcd for $C_{19}H_{12}N_2O_5$ 347.0668 [(M-H$^+$)$^-$]. found 347.0664 [(M-H$^+$)$^-$]; HPLC purity: 95.2% (MeOH—$H_2O$, 85:15), 95.7% (MeOH—$H_2O$, 75:25).

3-[(6-Methyl-5,11-dioxo-6,11-dihydro-5H-indeno[1,2-c]isoquinolin-3-yl)amino]-3-oxopropanoic Acid (15)

Methyl 3-[(6-methyl-5,11-dioxo-6,11-dihydro-5H-indeno[1,2-c]isoquinolin-3-yl)amino]-3-oxopropanoate (10, 158 mg, 0.42 mmol) was dissolved in methanol (20 mL) and dimethylformamide (2 mL). A solution of sodium hydroxide (103 mg) in water (2 mL) was added dropwise and the reaction mixture was stirred at room temperature for 24 h. Concentrated hydrochloric acid (1 mL) was added and the solution diluted with chloroform (30 mL). A dark-red precipitated was formed between the two phases. The solid was filtered and the organic and water layers discarded. The solid was washed with water (10 mL) and ether (2×10 mL). The solid was dried and compound 15 was obtained as a reddish-brown solid (93 mg, 61%): mp 262° C. (dec). IR (KBr) 3447, 3323, 1731, 1695, 1573, 1529, 1433, 1317, 1195, 1054, 899, 763 cm$^{-1}$; $^1$H NMR (300 MHz, DMSO-d$_6$) δ 10.5 (s, 1H), 8.45 (s, 1H), 8.31 (d, J=8.6 Hz, 1H), 7.80 (d, J=7.0 Hz, 1H), 7.46-7.38 (m, 3H), 3.86 (s, 3H), 3.39 (s, 2H); $^{13}$C NMR (125 MHz, DMSO-d$_6$) δ 190.1, 169.5, 165.1, 162.4, 155.7, 138.1, 137.5, 134.5, 133.8, 131.2, 127.6, 125.7, 124.1, 123.6, 122.7, 117.0, 116.9, 106.9, 44.4, 32.4; MALDIMS m/z (rel intensity) 363 (MH$^+$, 100); ESIMS (m/z, relative intensity) 361 [(M-H$^+$)$^-$], 100); HRESIMS calcd for C$_{20}$H$_{14}$N$_2$O$_5$ 361.0824 [(M-H$^+$)$^-$]. found 361.0828 [(M-H$^+$)$^-$]; negative ion; HPLC purity: 99.4% (MeOH, 100), 98.6% (MeOH—H$_2$O, 95:5).

Methyl 2-[(6-(3-((tert-Butoxycarbonyl)amino)propyl)-5,11-dioxo-6,11-dihydro-5H-indeno[1,2-c]isoquinolin-3-yl)amino]-2-oxoacetate (17)

Compound 16 (0.3 g, 0.715 mmol) was dissolved in chloroform (100 mL). Triethylamine (0.261 g, 2.14 mmol) was added at room temperature followed by methyl oxaloyl chloride (4, 0.113 g, 0.930 mmol) and the reaction mixture was stirred for 2 h. The reaction mixture was washed with water (2×20 mL) and dried over anhydrous sodium sulfate. The solvent was removed under vacuum and the residue purified by silica gel column chromatography, eluting with chloroform-methanol, 9.4:0.4, to furnish the product 17 (0.230 g, 65%) as an orange solid: mp 157-159° C. IR (KBr) 3339, 2976, 1702, 1662, 1580, 1570, 1534, 1514, 1163, 759, 665 cm$^{-1}$; $^1$H NMR (CDCl$_3$, 300 MHz) δ 9.02 (s, 1H), 8.73 (d, J=8.7 Hz, 1H), 8.32 (s, 1H), 8.10 (dd, J=1.8, J=5.6 Hz, 1H), 7.68 (m, 1H), 7.48 (m, 1H), 7.30 (m, 2H), 5.30 (m, 1H), 4.58 (t, J=4.8 Hz, 2H), 3.99 (s, 3H), 3.26 (m, 2H), 2.10 (m, 2H), 1.45 (s, 9H); $^{13}$C NMR (CDCl$_3$+CD$_3$OD, 75 MHz) δ 163.2, 160.6, 156.5, 154.6, 136.5, 135.6, 134.5, 133.4, 130.9, 129.2, 126.4, 124.3, 123.5, 123.1, 122.5, 118.3, 108.4, 79.3, 53.6, 42.2, 37.2, 29.5, 28.0; ESIMS m/z (relative intensity) 528 (MNa$^+$, 62); HRESIMS calcd for C$_{27}$H$_{27}$N$_3$O$_7$Na 528.1747 (MNa$^+$). found 528.1740 (MNa$^+$).

Methyl 3-[(6-(3-((tert-Butoxycarbonyl)amino)propyl)-5,11-dioxo-6,11-dihydro-5H-indeno[1,2-c]isoquinolin-3-yl)amino]-3-oxopropanoate (18)

Compound 16 (0.100 g, 0.234 mmol) was dissolved in chloroform (75 mL), triethylamine (0.060 g, 0.591 mmol) was added followed by methyl 3-chloro-3-oxopropionate (5, 0.055 g, 0.290 mmol) at room temperature, and the reaction mixture was stirred for 2 h. The reaction mixture was washed with water (2×20 mL), extracted with chloroform (2×75 mL), and dried over anhydrous sodium sulfate. The solvent was removed under vacuum and the residue purified by silica gel column chromatography, eluting with chloroform-methanol, 9.3:0.7, to furnish the product 18 (0.075 g, 65%) as a red solid: mp 144-145° C. IR (KBr) 3325, 2976, 1744, 1696, 1664, 1572, 1532, 1512, 1433, 1168, 761, 665 cm$^{-1}$; $^1$H NMR (CDCl$_3$, 300 MHz) δ 9.47 (s, 1H), 8.65 (d, J=8.8 Hz, 1H), 8.35 (s, 1H), 8.06 (m, 1H), 7.59 (m, 1H), 7.50 (m, 1H), 7.41 (m, 2H), 5.40 (br s, 1H), 4.60 (t, J=6.6 Hz, 2H), 3.82 (s, 3H), 3.53 (s, 2H), 3.50 (m, 2H), 2.08 (m, 2H), 1.45 (s, 9H); $^{13}$C NMR (CDCl$_3$, 300 MHz) δ 190.0, 169.8, 163.3, 163.0, 156.1, 154.1, 136.7, 136.5, 134.6, 133.2, 130.6, 128.5, 126.5, 124.2, 123.6, 123.0, 122.3, 118.2, 108.3, 79.2, 52.6, 42.0, 41.7, 37.3, 29.9, 28.4; ESIMS m/z (relative intensity) 542 (MNa$^+$, 100); HRESIMS calcd for C$_{28}$H$_{29}$N$_3$O$_7$Na 542.1903 (MNa$^+$). found 542.1906 (MNa$^+$); 95.7% (MeOH—H$_2$O, 85:15).

Methyl 4-[(6-(3-((tert-Butoxycarbonyl)amino)propyl)-5,11-dioxo-6,11-dihydro-5H-indeno[1,2-c]isoquinolin-3-yl)amino]-4-oxobutanoate (19)

Compound 16 (0.150 g, 0.357 mmol) was dissolved in chloroform (100 mL), triethylamine (0.090 g, 0.892 mmol) was added followed by methyl 4-chloro-4-oxobutanoate (6, 0.082 g, 0.536 mmol) at room temperature, and the reaction mixture was stirred for 2 h. The reaction mixture was washed with water (2×20 mL), extracted with chloroform (2×75 mL), and dried over anhydrous sodium sulfate. The solvent was removed under vacuum and the residue purified by silica gel column chromatography, eluting with chloroform-methanol, 9.5:0.5, to furnish the product 19 (0.114 g, 60%) as an orange solid: mp 176-178° C. IR (KBr) 3307, 2917, 1728, 1703, 1718, 1695, 1575, 1165, 666 cm$^{-1}$; $^1$H NMR (CDCl$_3$, 300 MHz) δ 8.68 (d, J=5.3 Hz, 1H), 8.21 (br s, 1H), 8.02 (m, 2H), 7.68 (d, J=4.8 Hz, 1H), 7.32 (m, 4H), 5.41 (br s, 1H), 4.57 (t, J=3.2 Hz, 2H), 3.72 (s, 3H), 3.20 (m, 2H), 2.79 (m, 4H), 2.08 (m, 2H), 1.45 (s, 9H); $^{13}$C NMR (CDCl$_3$+DMSO-d$_6$, 125 MHz) δ 190.0, 173.0, 170.0, 162.9, 155.8, 153.6, 137.9, 136.7, 134.5, 133.0, 130.3, 127.4, 126.0, 123.7, 123.4, 122.6, 122.0, 117.2, 108.3, 78.7, 51.4, 41.6, 36.9, 31.1, 29.6, 28.6, 28.1; ESIMS m/z (relative intensity) 556 (MNa$^+$, 12); HRESIMS calcd for C$_{29}$H$_{31}$N$_3$O$_7$Na 556.2060. found 556.2069; HPLC purity: 95.0% (MeOH—H$_2$O, 85:15).

Methyl 5-[(6-(3-((tert-Butoxycarbonyl)amino)propyl)-5,11-dioxo-6,11-dihydro-5H-indeno[1,2-c]isoquinolin-3-yl)amino]-5-oxopentanoate (20)

Compound 16 (0.150 g, 0.357 mmol) was dissolved in chloroform (100 mL), triethylamine (0.108 g, 1.07 mmol) was added followed by methyl 5-chloro-5-oxopentanoate (7, 0.088 g, 0.536 mmol) at room temperature, and the reaction mixture was stirred for 2 h. The reaction mixture was washed with water (2×25 mL), extracted with chloroform (2×60 mL), and dried over anhydrous sodium sulfate. The solvent was removed under vacuum and the residue purified by silica gel column chromatography, eluting with chloroform-methanol, 9.6:0.4, to afford the product 20 (0.1 g, 50%) as a red solid: mp 118-120° C. IR (KBr) 3329, 1696, 1679, 1663, 1596, 1528, 1169, 760 cm$^{-1}$; $^1$H NMR (CDCl$_3$, 300 MHz) δ 8.52 (d, J=5.3 Hz, 1H), 8.21 (br s, 1H), 8.01 (br s, 1H), 7.48 (d, J=4.7 Hz, 1H), 7.40 (m, 2H), 7.26 (m, 2H), 5.48 (t, J=4.5 Hz, 1H), 4.51 (t, J=4.5 Hz, 2H), 3.69 (s, 3H), 3.20 (m, 2H), 2.49 (m, 4H), 2.10 (m, 4H), 1.45 (s, 9H); $^{13}$C NMR (CDCl$_3$, 125 MHz) δ 190.2, 173.8, 170.8, 163.2, 156.1, 154.0, 137.1, 136.9, 134.7, 133.3, 130.7, 128.3, 126.6, 124.3, 123.7, 123.1, 122.3, 117.9, 108.6, 79.3, 51.7, 41.9, 37.3, 36.1, 32.9, 30.0, 28.4, 20.6; ESIMS m/z (relative intensity) 570 (MNa$^+$, 100); HRESIMS calcd for C$_{30}$H$_{33}$N$_3$O$_7$Na 570.2216 (MNa$^+$). found 570.2209 (MNa$^+$); HPLC purity: 96.4% (MeOH—H$_2$O, 85:15).

Methyl 6-[(6-(3-((tert-Butoxycarbonyl)amino)propyl)-5,11-dioxo-6,11-dihydro-5H-indeno[1,2-c]isoquinolin-3-yl)amino]-6-oxohexanoate (21)

Compound 16 (0.150 g, 0.357 mmol) was dissolved in chloroform (100 mL), triethylamine (0.090 g, 0.892 mmol) was added followed by methyl 6-chloro-6-oxohexanoate (8, 0.095 g, 0.536 mmol) at room temperature, and the reaction mixture was stirred for 2 h. The reaction mixture washed with water (2×30 mL), extracted with chloroform (2×75 mL), and dried over anhydrous sodium sulfate. The solvent was removed under vacuum and the residue purified by silica gel column chromatography, eluting with chloroform-methanol, 9.7:0.3, to yield the product 21 (0.116 g, 55%) as a red solid: mp 143-145° C. IR (KBr) 3332, 2974, 1696, 1662, 1580, 1568, 1527, 1169, 760, 666 cm$^{-1}$; $^1$H NMR (CDCl$_3$, 300 MHz) δ 8.46 (d, J=8.7 Hz, 1H), 8.28 (br s, 1H), 8.03 (br s, 1H), 7.93 (d, J=5.2 Hz, 1H), 7.52 (d, J=5.2 Hz, 1H), 7.31 (m, 2H), 7.28 (d, J=6.3 Hz, 1H), 5.43 (t, J=5.4 Hz, 1H), 4.48 (t, J=6.6 Hz, 2H), 3.67 (s, 3H), 3.18 (m, 2H), 2.38 (m, 4H), 2.05 (m, 2H), 1.76 (m, 4H), 1.45 (s, 9H); $^{13}$C NMR (CDCl$_3$, 125 MHz) δ 190.3, 174.1, 171.1, 163.1, 156.1, 154.1, 137.2, 136.9, 134.8, 133.3, 130.7, 128.3, 126.7, 124.3, 123.7, 123.1, 122.3, 118.0, 108.6, 79.3, 51.6, 41.9, 37.3, 37.0, 33.6, 30.0, 28.4, 24.8, 24.2; ESIMS m/z (relative intensity) 584 (MNa$^+$, 17); HRESIMS calcd for C$_{31}$H$_{35}$N$_3$O$_7$Na 584.2373. found 584.2370.

Methyl 2-[(6-(3-Aminopropyl)-5,11-dioxo-6,11-dihydro-5H-indeno[1,2-c]isoquinolin-3-yl)amino]-2-oxoacetate (22)

Compound 17 (0.070 g, 0.130 mmol) was treated with trifluoroacetic acid (0.5 mL) in chloroform (5 mL) for 2 h at room temperature. The solvent was removed on a rotary evaporator and the residue was then basified with 2 N NH$_3$ in methanol to get the free amine, which was purified by silica gel column chromatography, eluting with chloroform-methanol, 8.7:1.3, to yield the product 22 (0.035 g, 65%) as a brown solid: mp 185-186° C. IR (KBr) 3014, 1692, 1581, 1570, 1533, 1307, 1198, 722, 455 cm$^{-1}$; $^1$H NMR (CD$_3$OD, 300 MHz) δ 8.55 (s, 1H), 8.23 (d, J=3.2 Hz, 1H), 7.71 (d, J=3.5 Hz, 1H), 7.54 (m, 1H), 7.36 (m, 3H), 4.52 (m, 2H), 3.91 (s, 3H), 3.05 (m, 2H), 2.28 (m, 2H); $^{13}$C NMR (CD$_3$OD, 125 MHz) δ 191.6, 169.9, 166.8, 164.9, 155.4, 138.8, 137.9, 135.7, 134.9, 132.2, 129.6, 127.2, 125.0, 124.8, 124.1, 123.9, 118.6, 109.6, 52.9, 42.5, 38.2, 28.6; ESIMS m/z (relative intensity) 420 (MH$^+$, 100); HRESIMS calcd for C$_{23}$H$_{21}$N$_3$O$_5$ 420.1559 (MH$^+$). found 420.1554 (MH$^+$); HPLC purity: 98.2% (1% TFA in MeOH).

Methyl 3-[(6-(3-Aminopropyl)-5,11-dioxo-6,11-dihydro-5H-indeno[1,2-c]isoquinolin-3-yl)amino]-3-oxopropanoate (23)

Compound 18 (0.080 g, 0.145 mmol) was treated with TFA (0.5 mL) in chloroform (5 mL) for 2 h at room temperature. The solvent was removed on a rotary evaporator and the residue was then basified with 2 N NH$_3$ in methanol to get the free amine, which was purified by silica gel column chromatography, eluting with chloroform-methanol, 8.8:1.2, to yield the product 23 (0.040 g, 62%) as a brown solid: mp 225-227° C. IR (KBr) 3067, 1739, 1673, 1574, 1535, 1511, 1202, 1134, 722 cm$^{-1}$; $^1$H NMR (CD$_3$OD, 300 MHz) 8.52 (d, J=2.1 Hz, 1H), 8.29 (d, J=6.8 Hz, 1H), 7.43 (m, 5H), 4.50 (t, J=2.1 Hz, 2H), 3.78 (s, 3H), 3.10 (m, 2H), 2.22 (m, 2H); $^{13}$C NMR (CD$_3$OD, 125 MHz) δ 191.6, 169.9, 166.8, 164.9, 155.4, 138.8, 137.9, 135.7, 134.9, 132.2, 129.6, 127.2, 125.0, 124.8, 124.1, 123.9, 118.6, 109.6, 52.9, 42.5, 38.2, 28.6; ESIMS m/z (relative intensity) 420 (MH$^+$, 100); HRESIMS calcd for C$_{23}$H$_{21}$N$_3$O$_5$ 420.1559 (MH$^+$). found 420.1554 (MH$^+$); HPLC purity: 100% (1% TFA in MeOH—H$_2$O, 50:50).

Methyl 4-[(6-(3-Aminopropyl)-5,11-dioxo-6,11-dihydro-5H-indeno[1,2-c]isoquinolin-3-yl)amino]-4-oxobutanoate (24)

Compound 19 (0.060 g, 0.112 mmol) was treated with trifluoroacetic acid (0.5 mL) in chloroform (5 mL) for 2 h at room temperature. The solvent was removed on a rotary evaporator and the residue was then basified with 2 N NH$_3$ in in methanol to get the free amine, which was purified by silica gel column chromatography, eluting with chloroform-methanol, 8.8:1.2, to yield the product 24 (0.028 g, 60%) as a brown solid: mp 272-274° C. IR (KBr) 2952, 1735, 1690, 1656, 1572, 1532, 1510, 1160, 765, 455 cm$^{-1}$; $^1$H NMR (CD$_3$OD, 300 MHz) δ 8.28 (s, 1H), 7.92 (m, 1H), 7.31 (m, 3H), 7.20 (s, 2H), 4.30 (t, J=4.8 Hz, 2H), 3.71 (s, 3H), 2.83 (m, 2H), 2.68 (m, 4H), 2.00 (m, 2H); $^{13}$C NMR (CD$_3$OD, 125 MHz) δ 191.8, 174.9, 172.6, 164.4, 155.6, 139.2, 138.2, 135.9, 134.8, 131.9, 129.3, 127.1, 125.0, 124.9, 124.0, 123.8, 122.9, 118.5, 114.8, 109.5, 57.6, 57.4, 57.2, 43.6, 36.3, 32.2, 30.3, 29.7; ESIMS m/z (relative intensity) 434 (MH$^+$, 100); HRESIMS calcd for C$_{24}$H$_{23}$N$_3$O$_5$ 434.1852 (MH$^+$). found 434.1835 (MH$^+$); HPLC purity: 98.0% (1% TFA in MeOH).

Methyl 5-[(6-(3-Aminopropyl)-5,11-dioxo-6,11-dihydro-5H-indeno[1,2-c]isoquinolin-3-yl)amino]-5-oxopentanoate (25)

Compound 20 (0.150 g, 0.274 mmol) was treated with trifluoroacetic acid (1.0 mL) in chloroform (10 mL) for 2 h at room temperature. The solvent was removed on a rotary evaporator and the residue was then basified with 2 N NH$_3$ in methanol to get the free amine, which was purified by silica gel column chromatography, eluting with chloroform-methanol, 9.0:1.0, to afford the product 25 (0.092 g, 75%) as a brown solid: mp 215-217° C. IR (KBr) 3075, 1729, 1687, 1673, 1572, 1532, 1433, 1202, 760, 722, 455 cm$^{-1}$; $^1$H NMR (DMSO-d$_6$, 300 MHz) δ 10.2 (s, 1H), 8.60 (d, J=1.8 Hz, 1H), 8.47 (d, J=8.7 Hz, 1H), 7.89 (dd, J=1.8, J=8.7 Hz, 1H), 7.74 (m, 3H), 7.54 (m, 2H), 7.47 (m, 1H), 4.53 (t, J=3.2 Hz, 2H), 3.59 (s, 3H), 2.96 (m, 2H), 2.38 (m, 4H), 2.13 (m, 2H), 1.87 (m, 2H); $^{13}$C NMR (DMSO-d$_6$, 75 MHz) δ 190.1, 173.0, 171.0, 162.6, 154.4, 138.3, 136.6, 134.2, 134.0, 131.0, 127.1, 125.8, 123.5, 123.4, 122.6, 116.6, 107.4, 79.1, 51.3, 41.2, 38.6, 36.6, 35.2, 32.6, 27.3, 20.2; ESIMS m/z (relative intensity) 448 (MH$^+$, 100); HRESIMS calcd for C$_{25}$H$_{25}$N$_3$O$_5$ 448.1867 (MH$^+$). found 448.1877 (MH$^+$); HPLC purity: 100% (1% TFA in MeOH—H$_2$O, 70:30).

Methyl 6-[(6-(3-Aminopropyl)-5,11-dioxo-6,11-dihydro-5H-indeno[1,2-c]isoquinolin-3-yl)amino]-6-oxohexanoate (26)

Compound 21 (0.030 g, 0.053 mmol) was treated with trifluoroacetic acid (0.25 mL) in chloroform (3 mL) for 2 h at room temperature. The solvent was removed on a rotary evaporator and the residue was then basified with 2 N NH$_3$ in methanol to get the free amine, which was purified by silica gel column chromatography, eluting with chloroform-methanol, 9.2:0.8, to yield the product 26 (0.015 g, 55%) as a red solid: mp 153-155° C. IR (KBr) 2947, 1739, 1705, 1693, 1661, 1570, 1530, 1431, 1197, 760, 665 cm$^{-1}$; $^1$H NMR (CD$_3$OD, 300 MHz) δ 8.51 (d, J=2.4 Hz, 1H), 8.34 (d, J=9.0 Hz, 1H), 7.70 (dd, J=2.4, J=9.0 Hz, 1H), 7.60 (t, J=9.0 Hz, 1H), 7.51 (m, 2H), 7.31 (m, 1H), 4.55 (t, J=4.5 Hz, 2H), 3.67 (s, 3H), 3.13 (m, 2H), 2.39 (m, 4H), 2.26 (m, 2H), 1.70 (m, 2H); $^{13}$C NMR (DMSO-d$_6$, 125 MHz) δ 190.0, 173.3, 171.3, 162.3, 154.4, 138.3, 136.6, 134.2, 133.9, 130.9, 127.0, 125.6, 123.5, 123.4, 123.3, 122.5, 116.5, 107.2, 51.2, 42.1, 38.2, 36.0, 33.0, 30.9, 24.4, 24.0; ESIMS (m/z, relative intensity) 462 (MH$^+$, 100); HRESIMS calcd for C$_{26}$H$_{27}$N$_3$O$_5$ 462.2023 (MH$^+$). found 462.2031 (MH$^+$); HPLC purity: 98.5% (1% TFA in MeOH—H$_2$O, 70:30).

General Procedure for Synthesis of Indenoisoquinolines 27-31

The esters 17-21 (0.1 g) were dissolved in methanol (10 mL) and tetrahydrofuran (10 mL). An aqueous NaOH solution (4 N, 5 mL) was added at room temperature and the reaction mixture was stirred at room temperature for 6 h. The solvent was removed on a rotary evaporator and the residue washed with 1 N HCl (30 mL), extracted with chloroform (2×50 mL), dried over anhydrous sodium sulfate, concentrated and purified by silica gel column chromatography, eluting with chloroform-methanol 9.6:0.4 to 9:1, to afford acids 27-31 in 55-75% yields as orange solids.

2-[(6-(3-((tert-Butoxycarbonyl)amino)propyl)-5,11-dioxo-6,11-dihydro-5H-indeno[1,2-c]isoquinolin-3-yl)amino]-2-oxoacetic Acid (27)

mp 267-268° C. IR (KBr) 3295, 1758, 1698, 1646, 1605, 1580, 1535, 1350, 1161, 847, 665 cm$^{-1}$; $^1$H NMR (CD$_3$OD+DMSO-d$_6$, 300 MHz) δ 8.87 (s, 1H), 8.63 (d, J=8.7 Hz, 1H), 8.14 (d, J=9.3 Hz, 1H), 7.80 (d, J=7.2 Hz, 1H), 7.64 (m, 2H), 7.55 (m, 1H), 4.60 (t, J=7.2 Hz, 2H), 3.21 (m, 2H), 2.07 (m, 2H), 1.50 (s, 1H).

3-[(6-(3-((tert-Butoxycarbonyl)amino)propyl)-5,11-dioxo-6,11-dihydro-5H-indeno[1,2-c]isoquinolin-3-yl)amino]-3-oxopropanoic Acid (28)

mp 211-212° C. IR (KBr) 3310, 1768, 1710, 1976, 1522, 1385, 1355, 847, 665 cm$^{-1}$; $^1$H NMR (CD$_3$OD, 300 MHz) δ 8.56 (d, J=2.2 Hz, 1H), 8.30 (d, J=5.6 Hz, 1H), 7.51 (m, 1H), 7.48 (m, 1H), 7.44 (m, 1H), 7.39 (m, 1H), 7.30 (m, 1H), 4.52 (t, J=4.5 Hz, 2H), 3.52 (s, 2H), 3.15 (t, J=5.8 Hz, 2H), 2.18 (m, 2H), 1.43 (s, 9H).

4-[(6-(3-((tert-Butoxycarbonyl)amino)propyl)-5,11-dioxo-6,11-dihydro-5H-indeno[1,2-c]isoquinolin-3-yl)amino]-4-oxobutanoic Acid (29)

mp 155-157° C. IR (KBr) 3315, 1763, 1698, 1678, 1543, 1345, 1165, 667 cm$^{-1}$; $^1$H NMR (CD$_3$OD, 300 MHz) δ 8.44 (m, 211), 7.82 (dd, J=2.1, J=5.5 Hz, 1H), 7.68 (d, J=5.5 Hz, 1H), 7.51 (m, 2H), 7.34 (m, 1H), 4.45 (m, 2H), 3.12 (m, 2H), 2.14 (s, 4H), 1.96 (m, 2H), 1.44 (s, 9H); $^{13}$C NMR (CDCl$_3$+DMSO-d$_6$, 75 MHz) δ 188.4, 172.3, 168.8, 160.8, 154.3, 152.3, 136.8, 135.3, 133.0, 131.8, 129.0, 125.7, 124.0, 122.1, 121.9, 121.2, 120.9, 115.2, 106.2, 40.9, 35.9, 29.7, 29.1, 28.1, 27.3, 26.7; ESIMS (m/z, relative intensity) 542 (MNa$^+$, 100), 420 (loss of Boc, 16); HRESIMS calcd for C$_{28}$H$_{29}$N$_3$O$_7$Na 542.1903 (MNa$^+$). found 542.1912 (MNa$^+$).

5-[(6-(3-((tert-Butoxycarbonyl)amino)propyl)-5,11-dioxo-6,11-dihydro-5H-indeno[1,2-c]isoquinolin-3-yl)amino]-5-oxopentanoic Acid (30)

mp 198-200° C. IR (KBr) 3307, 1696, 1690, 1663, 1569, 1528, 1401, 1366, 1250, 1167, 759 cm$^{-1}$; $^1$H NMR (CD$_3$OD, 300 MHz) δ 8.52 (d, J=5.3 Hz, 1H), 8.21 (br s, 1H), 8.01 (br, s, 1H), 7.48 (d, J=4.7 Hz, 1H), 7.40 (m, 2H), 7.26 (m, 1H), 4.51 (t, J=4.5 Hz, 2H), 3.20 (m, 2H), 2.49 (m, 4H), 2.10 (m, 4H), 1.45 (s, 9H); $^{13}$C NMR (CD$_3$OD+DMSO-d$_6$, 75 MHz) δ 191.5, 176.3, 173.2, 164.1, 158.0, 155.6, 139.3, 138.2, 135.9, 134.8, 131.9, 129.0, 127.0, 125.0, 124.8, 124.2, 123.8, 118.4, 109.1, 79.8, 79.7, 36.9, 34.2, 30.9, 29.0, 21.9; ESIMS (m/z, relative intensity) 556 (MNa$^+$, 100); HRESIMS calcd for C$_{29}$H$_{31}$N$_3$O$_7$ 556.2059 (MNa$^+$). found 556.2063 (MNa$^+$).

6-[(6-(3-((tert-Butoxycarbonyl)amino)propyl)-5,11-dioxo-6,11-dihydro-5H-indeno[1,2-c]isoquinolin-3-yl)amino]-6-oxohexanoic Acid (31)

mp 206-208° C. IR (KBr) 3312, 1702, 1695, 1670, 1573, 1534, 1376, 1250, 760, 665 cm$^{-1}$; $^1$H NMR (CDCl$_3$+CD$_3$OD, 300 MHz) δ 8.55 (d, J=6.2 Hz, 1H), 8.18 (s, 1H), 8.01 (m, 1H), 7.50 (d, J=3.5 Hz, 1H), 7.40 (d, J=3.5 Hz, 1H), 7.32 (m, 1H), 7.28 (d, J=3.5 Hz, 1H), 4.50 (m, 2H), 3.12 (m, 2H), 2.29 (m, 4H), 1.96 (m, 2H), 1.65 (m, 4H), 1.37 (s, 9H); $^{13}$C NMR (DMSO-d$_6$, 75 Hz) δ 190.0, 174.5, 171.5, 162.2, 155.8, 154.5, 138.3, 136.7, 134.3, 133.9, 131.0, 127.1, 125.7, 123.5, 123.3, 123.2, 122.7, 116.6, 107.3, 77.8, 42.5, 37.5, 36.2, 33.5, 29.6, 28.3, 24.6, 24.9; ESIMS (m/z, relative intensity) 570 (MNa$^+$, 23), 448 (loss of Boc, 100); HRESIMS calcd for C$_{30}$H$_{33}$N$_3$O$_7$Na 570.2216 (MNa$^+$). found 570.2207 (MNa$^+$).

General Procedure for Synthesis of Indenoisoquinolines 32-36

Acids 27-31 (0.050 g) were treated with HCl in diethyl ether (2 M, 2 mL) at room temperature for 5 h. The solvent was removed on a rotary evaporator to yield the solid hydrochloride salts, which were washed with 5% MeOH in chloroform to remove impurities and afford the pure products 32-36 in quantitative yields.

2-[(6-(3-Aminopropyl)-5,11-dioxo-6,11-dihydro-5H-indeno[1,2-c]isoquinolin-3-yl)amino]-2-oxoacetic Acid Hydrochloride (32)

mp 251-252° C. IR (KBr) 2955, 1742, 1733, 1641, 1578, 1535, 1431, 1195, 665 cm$^{-1}$; $^1$H NMR (DMSO-d$_6$, 300 MHz) δ 11.04 (s, 1H), 8.75 (dd, J=1.7, J=8.9 Hz, 1H), 8.49 (dd, J=4.0, J=8.8 Hz, 1H), 8.11 (m, 2H), 7.69 (m, 1H), 7.54 (m, 3H), 4.54 (m, 2H), 3.01 (m, 2H), 2.07 (m, 2H); ESIMS (m/z, relative intensity) 392 (MH$^+$, 100); HRESIMS calcd for C$_{21}$H$_{17}$N$_3$O$_5$ 392.1246 (MH$^+$). found 392.1249 (MH$^+$); HPLC purity: 96.6% (1% TFA in MeOH).

3-[(6-(3-Aminopropyl)-5,11-dioxo-6,11-dihydro-5H-indeno[1,2-c]isoquinolin-3-yl)amino]-3-oxopropanoic Acid Hydrochloride (33)

mp 205-207° C. IR (KBr) 2917, 2356, 1670, 1582, 1565, 1538, 1191, 665 cm$^{-1}$; $^1$H NMR (DMSO-d$_6$, 300 MHz) δ 10.65 (d, J=8.9 Hz, 1H), 8.48 (s, 1H), 8.40 (d, J=4.5 Hz, 1H), 7.88 (m, 4H), 7.71 (d, J=4.5 Hz, 1H), 7.56 (m, 2H), 7.41 (m, 1H), 4.54 (m, 2H), 3.64 (s, 1H), 3.52 (s, 1H), 3.00 (m, 2H), 2.09 (m, 2H); ESIMS (m/z, relative intensity) 406 (MH$^+$, 100); HRESIMS calcd for C$_{22}$H$_{19}$N$_3$O$_5$ 406.1403 (MH$^+$). found 406.1400 (MH$^+$); HPLC purity: 95.2% (1% TFA in MeOH).

4-[(6-(3-Aminopropyl)-5,11-dioxo-6,11-dihydro-5H-indeno[1,2-c]isoquinolin-3-yl)amino]-4-oxobutanoic Acid Hydrochloride (34)

mp 167-169° C. IR (KBr) 3080, 1671, 1571, 1533, 1508, 1197, 734, 665 cm$^{-1}$; $^1$H NMR (CD$_3$OD, 300 MHz) δ 8.68 (d, J=2.3 Hz, 1H), 8.55 (d, J=5.2 Hz, 1H), 7.78 (dd, J=2.3, J=5.4 Hz, 1H), 7.64 (m, 1H), 7.52 (m, 2H), 7.37 (m, 1H), 4.62 (m, 2H), 3.06 (m, 2H), 2.30 (m, 2H); ESIMS (m/z, relative intensity) 420 (MH$^+$, 100); HRESIMS calcd for C$_{23}$H$_{21}$N$_3$O$_5$ 420.1559 (MH$^+$). found 420.1565 (MH$^+$; 96.71% (1% TFA in MeOH).

5-[(6-(3-Aminopropyl)-5,11-dioxo-6,11-dihydro-5H-indeno[1,2-c]isoquinolin-3-yl)amino]-5-oxopentanoic Acid Hydrochloride (35)

mp 242-244° C. IR (KBr) 3583, 2348, 1761, 1723, 1695, 1510, 1497, 906, 673 cm$^{-1}$; $^1$H NMR (DMSO-d$_6$, 300 MHz) δ 10.33 (s, 1H), 8.63 (d, J=2.1 Hz, 1H), 8.49 (d, J=8.7 Hz, 1H), 7.89 (dd, J=2.1, J=8.7 Hz, 1H), 7.84 (br s, 2H), 7.76 (d, J=7.2 Hz, 1H), 7.54 (m, 2H), 7.40 (m, 1H), 4.53 (m, 2H), 3.04 (m, 2H), 2.40 (m, 2H), 2.04 (m, 4H), 2.13 (m, 2H), 1.85 (m, 2H); ESIMS (m/z, relative intensity) 434 (MH$^+$, 100); HRESIMS calcd for C$_{24}$H$_{23}$N$_3$O$_5$ 434.1716. found 434.1710; HPLC purity: 95.3% (1% TFA in MeOH).

6-[(6-(3-Aminopropyl)-5,11-dioxo-6,11-dihydro-5H-indeno[1,2-c]isoquinolin-3-yl)amino]-6-oxohexanoic Acid Hydrochloride (36)

mp 203-205° C. IR (KBr) 3583, 2952, 1730, 1719, 1646, 1570, 1528, 1431, 1195, 759, 667 cm$^{-1}$; $^1$H NMR (DMSO-d$_6$, 300 MHz) δ 10.30 (d, J=6.6 Hz, 1H), 8.85 (d, J=9.9 Hz, 1H), 8.51 (m, 1H), 7.91 (m, 1H), 7.76 (m, 3H), 7.51 (m, 3H), 4.50 (m, 2H), 3.32 (m, 1H), 3.22 (m, 1H), 2.39 (m, 2H), 2.27 (m, 2H), 2.11 (m, 1H), 1.91 (m, 1H), 1.58 (m, 4H); ESIMS (m/z, relative intensity) 448 (MH$^+$, 100); HRESIMS calcd for C$_{25}$H$_{26}$N$_3$O$_5$ 448.1872 (MH$^+$). found 448.1868 (MH$^+$); HPLC purity: 96.5% (1% TFA in MeOH).

Ethyl 2-[(6-Methyl-5,11-dioxo-6,11-dihydro-5H-indeno[1,2-c]isoquinolin-3-yl)amino]acetate (38)

3-Amino-6-methyl-5H-indeno[1,2-c]isoquinoline-5,11 (6H)-dione (3, 400 mg, 1.45 mmol) and ethyl glyoxylate (37, 0.3 mL, 50% solution in toluene) were dissolved in glacial acetic acid (25 mL). The reaction mixture was stirred overnight at room temperature. Sodium cyanoborohydride (1.00 g) was added in portions. Once the production of bubbles stopped, the reaction mixture was heated at reflux for 30 min. Water (150 mL) was added and the compound extracted with chloroform (3×50 mL). The organic layers were combined and washed with water (2×150 mL), aqueous sodium bicarbonate (100 mL) and brine (100 mL). The solvent was removed under vacuum and the compound purified by silica gel column chromatography, eluting with chloroform-methanol, 50:1. The product was obtained as a dark solid (351 mg, 67%): mp 207° C. (dec). IR (Film) 3380, 2929, 1735, 1694, 1654, 1560, 1434, 1212, 1017 cm$^{-1}$; $^1$H NMR (500 MHz, DMSO-d$_6$) δ 8.21 (d, J=8.7 Hz, 1H), 7.69 (d, J=7.5 Hz, 1H), 7.43-7.38 (m, 2H), 7.31 (t, J=7.4 Hz, 1H), 7.13 (dd, J=8.8 Hz, J=2.5 Hz, 1H), 7.10 (d, J=2.5 Hz, 1H), 6.67 (t, J=6.4 Hz, 1H), 4.09 (q, J=7.1 Hz, 2H), 3.96 (d, J=6.3 Hz, 2H), 3.87 (s, 3H), 1.12 (t, J=7.1 Hz, 3H); $^{13}$C NMR (125 MHz, CDCl$_3$) δ 190.7, 170.6, 163.0, 152.2, 146.1, 138.3, 134.8, 132.8, 130.0, 125.0, 124.7, 123.7, 122.9, 121.9, 121.2, 109.0, 107.0, 61.4, 45.3, 32.2, 14.1; ESIMS m/z (rel intensity) 363 (MH$^+$, 100); HRESIMS calcd for C$_{21}$H$_{18}$N$_2$O$_4$ 363.1345 (MH$^+$). found 363.1349 (MH$^+$); HPLC purity: 99.42% (MeOH—H$_2$O-TFA, 95:5:1), 95.33% (MeOH-TFA, 100:1).

Ethyl 2-[(6-(3-((tert-Butoxycarbonyl)amino)propyl)-5,11-dioxo-6,11-dihydro-5H-indeno[1,2-c]isoquinolin-3-yl]amino)acetate (39)

Compound 16 (0.200 g, 0.477 mmol) was dissolved in acetic acid (20 mL) and methanol (1 mL). Ethyl glyoxalate (37, 0.058 g, 0.577 mmol) was added to the reaction mixture, which was stirred at room temperature for 1.5 h. Sodium cyanoborohydride (0.071 g, 1.19 mmol) was added and stirring was continued for another 0.5 h. The solvents were removed on a rotary evaporator. The residue was washed with sodium bicarbonate (2×15 mL), extracted with CHCl$_3$ (2×60 mL), the combined organic layers were dried over anhydrous sodium bicarbonate, and the mixture was concentrated to get a crude product. The crude product was precipitated from hexane-chloroform (7+3 mL) to afford a pure violet solid 39 (0.215 g, 90%): mp 203-204° C. IR (KBr) 2977, 1739, 1698, 1650, 1619, 1579, 1523, 1390, 1365, 1198, 1171, 1020, 758, 455 cm$^{-1}$; $^1$H NMR (300 MHz, CDCl$_3$) δ 8.51 (d, J=8.7 Hz, 1H), 7.53 (d, J=6.4 Hz), 7.39 (m, 4H), 7.09 (dd, J=2.6, J=8.7 Hz, 1H), 5.44 (m, 1H), 4.66 (m, 1H), 4.56 (t, J=4.5 Hz, 2H), 4.30 (q, J=7.1 Hz, 2H), 4.01 (d, J=5.1 Hz, 2H), 3.23 (m, 2H), 2.06 (m, 2H), 1.45 (s, 9H), 1.31 (t, J=7.1 Hz, 3H); $^{13}$C NMR (CDCl$_3$, 125 MHz) δ 190.9, 170.6, 163.6, 156.1, 151.4, 146.3, 137.6, 134.9, 133.3, 130.1, 125.0, 124.9, 123.9, 123.1, 122.3, 121.7, 109.6, 107.2, 79.2, 61.6, 45.3, 41.7, 28.4, 14.2; ESIMS m/z (rel intensity) 528 (MNa$^+$, 100); HRESIMS calcd for C$_{28}$H$_{31}$N$_3$O$_6$Na 528.2111 (MNa$^+$). found 528.2108 (MNa$^+$).

Ethyl 2-[(6-(3-Aminopropyl)-5,11-dioxo-6,11-dihydro-5H-indeno[1,2-c]isoquinolin-3-yl)amino]acetate Hydrochloride (40)

Ester 39 (0.060 g, 0.011 mmol) was treated with 2 M HCl in diethyl ether (2 mL) at room temperature for 2 h. The solvent was removed on a rotary evaporator to yield the solid hydrochloride salt, which was washed with 5% MeOH in chloroform to remove impurities and afford the pure solid product 40 in quantitative yield: mp 253-254° C. IR (KBr) 3356, 2972, 1711, 1689, 1634, 1598, 1544, 1354, 1129, 665 cm$^{-1}$, $^1$H NMR (DMSO-d$_6$, 300 MHz) δ 8.31 (d, J=8.7 Hz, 1H), 8.04 (br s, 3H), 7.64 (m, 1H), 7.47 (m, 2H), 7.40 (m, 1H), 7.21 (dd, J=2.2, J=8.7 Hz, 1H), 7.14 (d, J=2.2 Hz, 1H), 4.49 (m, 2H), 4.13 (q, J=7.1 Hz, 2H), 4.00 (s, 2H), 2.92 (m, 2H), 2.09 (m, 2H), 1.20 (t, J=5.9 Hz, 3H); $^{13}$C NMR (DMSO-d$_6$, 300 MHz) δ 190.7, 190.2, 170.8, 162.8, 160.6, 156.0, 155.5, 137.3, 136.7, 134.3, 130.7, 124.2, 123.1, 118.8, 87.0, 60.4, 56.3, 36.8, 27.6, 18.8, 14.3; ESIMS (m/z, relative intensity) 406 (MH$^+$, 100); HRESIMS calcd for C$_{23}$H$_{23}$N$_3$O$_4$ 406.1767 (MH$^+$). found 406.1772 (MH$^+$)7: 95.66% (1% TFA in MeOH).

2-[(6-Methyl-5,11-dioxo-6,11-dihydro-5H-indeno[1,2-c]isoquinolin-3-yl)-amino]acetic Acid (41)

Ethyl 2-((6-methyl-5,11-dioxo-6,11-dihydro-5H-indeno[1,2-c]isoquinolin-3-yl)amino)acetate (38, 213 mg, 0.59 mmol) was dissolved in methanol (5 mL) and tetrahydrofuran (5 mL). A solution of potassium hydroxide (112 mg, 2.00 mmol) in water (5 mL) was added to the reaction mixture, which was stirred at room temperature for 10 h. Concentrated hydrochloric acid (1 mL) was added to the reaction mixture and the solvent removed under vacuum. Water (20 mL) was added, and the mixture was sonicated and filtered. The solid was washed with water (20 mL). The residue was then dissolved in a mixture of dimethylformamide (0.5 mL) and methanol (9.5 mL), heated and allowed to reach room temperature. Ethyl ether (25 mL) and hexane (10 mL) were added and the reaction mixture placed inside the refrigerator overnight. The solvent was filtered off and the residue dried. The product was obtained as a black solid (59 mg, 30.0%): mp 205° C. (dec). IR (KBr) 3361, 3032, 1725, 1698, 1650, 1619, 1578, 1527, 1432, 1391, 1318, 1217, 1197, 1054, 1016, 901, 839, 758 cm$^{-1}$; $^1$H NMR (300 MHz, CDCl$_3$) δ 12.63 (br s, 1H), 8.21 (d, J=8.7 Hz, 1H), 7.68 (d, J=7.5 Hz, 1H), 7.43-7.38 (m, 2H), 7.30 (t, J=7.4 Hz, 1H), 7.14 (dd, J=8.8 Hz, J=2.5 Hz, 1H), 7.09 (d, J=2.5 Hz, 1H), 6.56 (br s, 1H), 3.87 (s, 3H), 3.86 (s, 2H); $^{13}$C NMR (125 MHz, CDCl$_3$) δ 190.7, 172.5, 162.4, 152.7, 147.9, 138.3, 134.6, 133.8, 130.5, 124.8, 123.8, 123.4, 122.6, 122.1, 121.8, 107.9, 106.5, 44.7, 32.3; negative ion ESIMS m/z (rel intensity) 333 [M-H$^+$]$^-$, 100); HRESIMS calcd for C$_{19}$H$_{14}$N$_2$O$_4$Na, 357.0851 (MNa$^+$). found 357.0857 (MNa$^+$); Anal. calcd for C$_{19}$H$_{14}$N$_2$O$_4$: C, 68.26; H, 4.22; N, 8.38. Found: C, 68.03; H, 4.16; N, 8.35.

2-((6-(3-((tert-Butoxycarbonyl)amino)propyl)-5,11-dioxo-6,11-dihydro-5H-indeno[1,2-c]isoquinolin-3-yl)amino)acetic Acid (42)

The ester 39 (0.1 g, 0.02 mmol) was dissolved in MeOH-THF (10+10 mL) and aq NaOH (4 N, 5 mL) was added at room temperature. The reaction mixture was stirred at room temperature for 4 h. The solvent was removed on a rotary evaporator and the residue washed with 1 N HCl (30 mL) and extracted with CHCl$_3$ (2×50 mL). The extract was dried over Na$_2$SO$_4$ and concentrated to afford pure 42 (0.075 g, 80%) which was obtained as a brown solid: mp 190-192° C. IR (KBr) 3350, 2973, 1692, 1645, 1619, 1578, 1520, 1364, 1164, 666 cm$^{-1}$; $^1$H NMR (DMSO-d$_6$, 300 MHz) δ 8.30 (d, J=8.7 Hz, 1H), 7.59 (m, 1H), 7.45 (m, 2H), 7.39 (m, 1H), 7.21 (dd, J=2.4, J=8.7 Hz, 1H), 7.12 (d, J=2.4 Hz, 1H), 7.07 (m, 1H), 4.40 (m, 2H), 3.90 (s, 2H), 3.09 (m, 2H), 1.86 (m, 2H), 1.33 (s, 9H); ESIMS (m/z, relative intensity) 500 (MNa$^+$, 100); HRESIMS calcd for C$_{26}$H$_{27}$N$_3$O$_6$Na 500.1798 (MNa$^+$). found 500.1806 (MNa$^+$); HPLC purity: 95.5% (MeOH—H$_2$O, 75:25).

2-((6-(3-Aminopropyl)-5,11-dioxo-6,11-dihydro-5H-indeno[1,2-c]isoquinolin-3-yl)amino)acetic Acid Hydrochloride (43)

Acid 42 (0.070 g, 0.014 mmol) was treated with HCl in diethyl ether (2 M, 2 mL) at room temperature for 1 h. The solvent was removed on a rotary evaporator to provide the solid hydrochloride salt, which was washed with 10% MeOH in chloroform to remove impurities and afford the pure product 43 in quantitative yield: mp 263-264° C. IR (KBr) 3376, 2982, 1723, 1695, 1634, 1598, 1566, 1354, 1188, 667 cm$^{-1}$; $^1$H NMR (DMSO-d$_6$, 300 MHz) δ 8.34 (d, J=7.8 Hz, 1H), 8.28 (s, 1H), 8.12 (br s, 3H), 7.64 (m, 1H), 7.49 (m, 2H), 7.39 (m, 1H), 7.19 (dd, J=2.2, J=8.7 Hz, 1H), 7.12 (d, J=2.2 Hz, 1H), 4.50 (t, J=6.3 Hz, 2H), 3.90 (s, 2H), 2.90 (m, 2H), 2.10 (m, 2H); $^{13}$C NMR (DMSO-d$_6$, 125 MHz) δ 190.2, 163.1, 162.3, 136.7, 134.1, 130.7, 125.1, 124.2, 124.1, 123.2, 122.6, 107.8, 79.2, 41.2, 36.5, 27.2; ESIMS (m/z, relative intensity) 378 (MH$^+$, 100); HRESIMS calcd for C$_{21}$H$_{19}$N$_3$O$_4$ 378.1454 (MH$^+$). found 378.1458 (MH$^+$); HPLC purity: 95.3% (1% TFA in MeOH—H$_2$O, 50:50).

cis-2-(3-Bromopropyl)-3-(3-methoxyphenyl)-7-nitro-1-oxo-1,2,3,4-tetrahydroisoquinoline-4-carboxylic acid (48)

The Schiff base 46 (0,618 g, 2.41 mmol) was diluted in chloroform (50 mL) at 0° C. and 4-nitrohomophthalic anhydride (0.5 g, 2.41 mmol) was added. The red mixture was stirred at 0° C. for 1 h and then at room temperature for 3 h. The creamy orange mixture was filtered and the residue was washed with CHCl$_3$ to provide the product as a pale yellow solid (0.91 g, 82%): mp 122-123° C. IR (film) 3419, 3010, 1714, 1651, 1530, 1489, 1346, 1266, 1163, 758 cm$^{-1}$; $^1$H NMR (300 MHz, DMSO-d$_6$) δ 8.60 (d, J=2.4 Hz, 1H), 8.25 (dd, J=2.4, J=8.3 Hz, 1H), 7.47 (d, J=8.3 Hz, 1H), 7.16 (m, 1H), 6.78 (m, 1H), 6.64 (s, 1H), 6.59 (d, J=7.7 Hz, 1H), 5.10 (d, J=2.4 Hz, 1H), 4.08 (m, 1H), 3.65 (s, 3H), 3.33 (m, 2H), 2.92 (m, 2H), 2.10 (m, 2H).

6-(3-Bromopropyl)-5,6-dihydro-8-methoxy-3-nitro-5,11-dioxo-11H-indeno[1,2-c]isoquinoline (49)

Thionyl chloride (10 mL) was slowly added to a solution of cis-4-carboxy-N-(3-chloropropyl)-3,4-dihydro-3-(4-methoxyphenyl)-7-nitro-1(2H)isoquinolone (48, 1.94 g, 4.18 mmol) in benzene (60 mL). The reaction mixture was heated at reflux for 30 min, allowed to cool to room temperature, and concentrated. The residue was diluted with nitrobenzene (80 mL), chilled in an ice bath, and aluminum chloride (3.00 g, 22.5 mmol) was added. The reaction mixture was removed from the bath and heated at 100° C. for 1 h. Water (200 mL) was added, and the solution was extracted with CHCl$_3$ (3×70 mL). The combined organic layers were washed with sodium bicarbonate (3×75 mL) and brine (75 mL), and dried over sodium sulfate. The solution was concentrated, hexanes (250 mL) were added, and the liquid was decanted. The solid was washed with hexanes (100 mL) and the liquid was decanted again. The solid was purified by silica gel column chromatography, eluting with chloroform-methanol, 20:1, to provide a red-orange solid (1.02 g, 55%): mp 282-284° C. (dec). IR (Film) 1699, 1667, 1612, 1555, 1499, 1332, 1159, 1078, 840, 785, 688, 662 cm$^{-1}$; $^1$H NMR (CDCl$_3$, 300 MHz) δ 8.85 (d, J=2.5 Hz, 1H), 8.70 (d, J=8.9 Hz, 1H), 8.55 (d, J=8.9 Hz, 1H), 7.60 (d, J=8.5 Hz, 1H), 7.38 (s, 1H), 7.06 (d, J=8.3 Hz, 1H), 4.60 (t, J=7.3 Hz, 2H), 3.91 (s, 3H), 3.75 (t, J=6.4 Hz, 2H), 2.36 (t, J=7.0 Hz, 2H); EIMS m/z (rel intensity) 444 (M$^+$, 100), 442 (M$^+$, 100), 363 [(M-Br)$^+$, 69]; HRESIMS calcd for C$_{20}$H$_{15}$BrN$_2$O$_5$ 442.0164 (MH$^+$). found 442.0158 (MH$^+$); Anal. Calcd for C$_{20}$H$_{15}$BrN$_2$O$_5$·0.8H$_2$O: C, 52.49; H, 3.66; N, 6.12; Br, 17.46. Found: C, 52.20; H, 3.54; N, 5.96; Br, 17.46.

6-(3-Azidopropyl)-5,6-dihydro-8-methoxy-3-nitro-5,11-dioxo-11H-indeno[1,2-c]isoquinoline (50)

Sodium azide (0.59 g, 9.07 mmol) and 6-(3-bromopropyl)-5,6-dihydro-8-methoxy-3-nitro-5,11-dioxo-11H-indeno[1,2-c]isoquinoline (49; 261 mg, 0.59 mmol) were diluted with DMSO (30 mL), and the mixture was heated at 90° C. for 12 h. The reaction mixture was diluted with chloroform (100 mL), washed with water (100 mL) and sat aq NaCl (30 mL), and dried over sodium sulfate. The solution was concentrated to provide a crude solid that was purified by silica gel column chromatography, eluting with chloroform-methanol, 50:1, to afford an orange solid (92 mg, 40%): mp 310° C. (dec). IR (KBr) 3060, 3015, 2979, 2090, 1691, 1668, 1614, 1560, 1504, 1371, 1344, 1258, 1232, 1082, 1022, 911, 876, 843, 775 cm$^{-1}$; $^1$H NMR (CDCl$_3$, 300 MHz) δ 8.88 (d, J=2.5 Hz, 1H), 8.67 (d, J=8.9 Hz, 1H), 8.50 (dd, J=8.9 Hz, J=2.5 Hz, 1H), 7.59 (d, J=8.4 Hz, 1H), 7.38 (d, J=2.0 Hz, 1H), 7.04 (dd, J=8.1 Hz, J=1.9 Hz, 1H), 4.57 (t, J=7.2 Hz, 2H), 3.91 (s, 3H), 3.59 (t, J=6.4 Hz, 2H), 2.07 (t, J=7.0 Hz, 2H); $^{13}$C NMR (125 MHz, DMSO-d$_6$) δ 188.6, 164.6, 162.3, 157.7, 145.7, 138.5, 136.7, 127.9, 127.3, 125.2, 124.5, 124.3, 123.2, 114.7, 113.7, 108.0, 56.6, 49.0, 42.8, 28.3; ESIMS (rel intensity) 405 (MH$^+$, 41), 322 [(M-C$_3$H$_7$N$_3$)$^+$, 100]; HRESIMS m/z calcd for C$_{20}$H$_{15}$N$_5$O$_5$ 405.1073 (MH$^+$). found, 405.1069 (MH$^+$); HPLC purity: 95.0% (MeOH, 100), 95.2% (MeOH—H$_2$O, 85:15).

6-(3-Aminopropyl)-5,6-dihydro-8-methoxy-3-nitro-5,11-dioxo-11H-indeno[1,2-c]isoquinoline Hydrochloride (51)

Triethylphosphite (1.0 mL) was added to a solution of 6-(3-azidopropyl)-5,6-dihydro-8-methoxy-3-nitro-5,11-dioxo-11H-indeno[1,2-c]isoquinoline (50, 0.287 g, 0.710 mmol) in benzene (50 mL), and the reaction mixture was heated at reflux for 16 h. The reaction mixture was allowed to cool to room temperature, HCl in methanol (3 M, 10 mL) was added, and the reaction mixture was heated at reflux for 4 h. The reaction mixture was allowed to cool to room temperature and filtered to provide a red solid (0.180 g, 61%): mp 288-290° C. IR (KBr) 3060, 3015, 2979, 2090, 1691, 1668, 1614, 1560, 1504, 1371, 1344, 1258, 1232, 1082, 1022, 911, 876, 843, 775 cm$^{-1}$; $^1$H NMR (300 MHz, CDCl$_3$) δ 8.84 (d, J=2.5 Hz, 1H), 8.69 (d, J=8.9 Hz, 1H), 8.53 (dd, J=8.9 Hz, J=2.5 Hz, 1H), 7.87 (br s, 3H), 7.60 (d, J=8.4 Hz, 1H), 7.30 (d, J=2.0 Hz, 1H), 7.05 (dd, J=8.1 Hz, J=1.9 Hz, 1H), 4.54 (t, J=7.2 Hz, 2H), 3.91 (s, 3H), 2.94 (t, J=6.4 Hz, 2H), 2.10 (t, J=7.0 Hz, 2H); $^{13}$C NMR (125 MHz, DMSO-d$_6$) δ 188.6, 164.6, 162.6, 157.6, 145.8, 138.3, 136.7, 128.0, 127.3, 125.3, 124.6, 124.2, 123.2, 114.6, 113.8, 108.2, 56.6, 42.3, 37.2, 27.3; ESIMS m/z (rel intensity) 380 (MH$^+$, 72), 363 ([(M-NH$_3$]$^+$, 100); HRESIMS m/z calcd for C$_{20}$H$_{17}$N$_3$O$_5$ 380.1246 (MH$^+$). found, 380.1243; HPLC purity: 97.2% (MeOH—H$_2$O, 90:10).

6-(3-(1H-Imidazol-1-yl)propyl)-8-methoxy-3-nitro-5H-indeno[1,2-c]isoquinoline-5,11(6H)-dione (52)

6-(3-Bromopropyl)-8-methoxy-3-nitro-5H-indeno[1,2-c]isoquinoline-5,11(6H)-dione (49, 120 mg, 0.27 mmol) was dissolved dimethylformamide (2 mL) and dioxane (10 mL). Sodium iodide (208 mg, 1.40 mmol) was added and the reaction mixture was heated at 60° C. for 6 h. Imidazole (202 mg, 297 mmol) and potassium carbonate (225 mg, 1.63 mmol) were added and the reaction mixture was stirred at 90° C. for 12 h. Water (15 mL) was added and a precipitated formed. The solid was filtered and kept. The remaining solution was diluted with water (100 mL) and the aqueous phase extracted with chloroform (3×30 mL). The organic extracts were combined, washed with water (3×100 mL), and dried over sodium sulfate. The filtered solid from the previous step was combined with the organic extracts, the solvent was removed in vacuo and the compound purified by silica gel column chromatography, eluting with chloroform-methanol, 50:1. The compound was obtained as a dark yellow solid (47 mg, 40%): mp 265-276° C. IR (Film) 1693, 1673, 1614, 1559, 1336, 1234, 1075, 866, 842, 774 cm$^{-1}$; $^1$H NMR (CDCl$_3$, 300 MHz) δ 9.19 (d, J=2.1 Hz, 1H), 8.89 (d, J=8.9 Hz, 1H), 8.48 (dd, J=8.9 Hz, J=2.2 Hz, 1H), 7.68-7.60 (m, 2H), 7.13 (br s, 1H), 7.06 (br s, 1H), 6.86-6.83 (m, 2H), 4.55 (t, J=7.1 Hz, 2H), 4.23 (t, J=6.5 Hz, 2H), 3.93 (s, 3H), 2.41 (p, J=7.1 Hz, 2H); $^{13}$C NMR (CDCl$_3$, 125 MHz) δ 188.6, 164.3, 162.4, 157.6, 145.4, 137.9, 136.5, 136.1, 128.2, 126.8, 125.4, 124.4, 124.2, 122.9, 114.2, 113.7, 107.9, 56.5, 46.5, 41.7, 29.7; ESIMS m/z (rel intensity) 431 (MH$^+$, 100); HRESIMS calcd for C$_{23}$H$_{18}$N$_4$O$_5$ 431.1355 (MH$^+$). found 431.1352 (MH$^+$); HPLC purity: 96.8% (MeOH—H$_2$O, 90:10).

8-Methoxy-6-(3-morpholinopropyl)-3-nitro-5H-indeno[1,2-c]isoquinoline-5,11(6H)-dione (53)

6-(3-Bromopropyl)-8-methoxy-3-nitro-5H-indeno[1,2-c]isoquinoline-5,11(6H)-dione (49, 117 mg, 0.26 mmol) was dissolved in dimethylformamide (2 mL) and dioxane (10 mL). Sodium iodide (213 mg, 1.42 mmol) was added and the reaction mixture was heated at 60° C. for 6 h. Morpholine (0.2 mL, 2.30 mmol) and potassium carbonate (260 mg, 1.88 mmol) were added and the reaction mixture was stirred at 90° C. for 12 h. Water (200 mL) was added and the compound extracted with chloroform (3×35 mL). The organic extracts were combined, washed with water (3×100 mL) and dried over sodium sulfate. The solvent was removed in vacuo and the compound purified by silica gel column chromatography, eluting with chloroform-methanol, 50:1. The product was obtained as an orange solid (30 mg, 25%): mp 276-278° C. IR (Film) 3020, 1676, 1614, 1562, 1337, 1215, 1066, 846, 757, 666 cm$^{-1}$; $^1$H NMR (CDCl$_3$, 300 MHz) δ 9.18 (d, J=2.2 Hz, 1H), 8.90 (d, J=8.9 Hz, 1H), 8.47 (dd, J=9.0 Hz, J=2.3 Hz, 1H), 7.50-7.48 (m, 2H), 7.10 (dd, J=8.9 Hz, J=2.1 Hz, 1H), 4.63 (t, J=7.6 Hz, 2H), 4.03 (s, 3H), 3.72 (m, 4H), 2.59 (t, J=6.2 Hz, 2H), 2.50 (s, 4H) 2.06 (m, 2H); $^{13}$C NMR (CDCl$_3$, 125 MHz) δ 188.0, 162.5, 157.5, 156.9, 145.3, 137.8, 136.8, 136.7, 128.2, 124.2, 123.1, 118.6, 118.5, 117.9, 106.9, 63.5, 56.4, 53.5, 51.3, 42.0, 23.5; ESIMS m/z (rel intensity) 450 (MH$^+$, 62); HRESIMS calcd for C$_{24}$H$_{13}$N$_3$O$_6$ 450.1665 (MH$^+$). found 450.1660 (MH$^+$); HPLC purity: 97.7% (MeOH—H$_2$O, 85:15), 97.8% (MeOH—H$_2$O, 90:10).

1-Bromo-6-cyanophthalide (65)

6-Cyanophthalide (64, 2.73 g, 17.2 mmol) was dissolved in carbon tetrachloride (120 mL). 3-Chloroperbenzoic acid (100 mg) and N-bromosuccinimide (3.20 g, 17.9 mmol) were added. Light was applied with a 250 W lamp and the reaction mixture was heated at reflux for 24 h. The solvent was removed and the residue purified by silica gel column chromatography, eluting with ethyl acetate-hexane, 1:7. The product was obtained as a white solid (2.32 g, 56.7%): mp 132-134° C. IR (Film) 3090, 3064, 3032, 2992, 2235, 1788, 1738, 1428, 1295, 1227, 1119, 990, 717, 664 cm$^{-1}$; NMR (300 MHz, CDCl$_3$) δ 8.23 (s, 1H), 8.05 (dd, J=1.1 Hz, J=8.1 Hz, 1H), 7.79 (d, J=7.9 Hz, 1H), 7.44 (s, 1H); $^{13}$C NMR (75 MHz, CDCl$_3$) δ 165.1, 152.2, 138.3, 130.0, 125.0, 121.5, 116.8, 115.3, 73.4; CIMS m/z (rel intensity) 238 (MH$^+$, 13), 160 [(MH—Br)$^+$, 100].

7-Cyano-3-hydroxyphthalide (66)

1-Bromo-6-cyanophthalide (65, 1.99 g, 8.36 mmol) was dissolved in hot water (50 mL). The reaction mixture was heated at reflux for 3 h. Ethanol (20 mL) was added and the solution was concentrated to half its volume and heated at reflux for 5 min. Once the solution reached room temperature the reaction mixture was placed in the refrigerator. The desired compound was recrystallized as off-white solid (1.23 g, 84.1%): mp 138-140° C. $^1$H NMR (300 MHz, DMSO-d$_6$) δ 8.42 (br s, 1H), 8.37 (d, J=1.8 Hz, 1H), 8.24 (dd, J=7.8 Hz, J=1.7 Hz, 1H), 7.90 (d, J=7.9 Hz, 1H), 6.75 (s, 1H); ESIMS m/z (rel intensity) 174 (MH$^+$, 100).

3-Cyano-5,11-dihydro-5,11-dioxoindeno[1,2-c]isochromene (68)

7-Cyano-3-hydroxyphthalide (66, 1.41 g, 8.06 mmol) and phthalide (67, 1.08 g, 8.06 mmol) were dissolved in ethyl acetate (15 mL). Sodium (0.80 g, 34.8 mmol) was added to methanol (30 mL) at 0° C. and the resulting solution added to the reaction mixture. The reaction mixture was stirred for 30 min at room temperature and then heated at reflux for 6 h. Concentrated hydrochloric acid (15 mL) was added and the solvent removed under vacuum. Benzene (100 mL) and para-toluenesulfonic acid (50 mg) were added, and the reaction mixture was connected to a Dean-Stark trap and heated at reflux for 16 h. Chloroform (150 mL) was added and the reaction mixture was heated at reflux and immediately filtered. The solvent was removed under vacuum and the solid recrystallized from chloroform to remove unreacted phthalide. The compound was purified by silica gel column chromatography, eluting with chloroform-methanol, 50:1. The product was obtained as a yellow solid (1.03 g, 46.8%): mp 225-227° C. IR (KBr) 3118, 3082, 2232, 1760, 1747, 1715, 1503, 1385, 1309, 1018, 877, 777, 763, 665 cm$^{-1}$; $^1$H NMR (300 MHz, DMSO-d$_6$) δ 8.59 (s, 1H), 8.47 (d, J=8.2 Hz, 1H), 7.99 (dd, J=8.2 Hz, J=1.6 Hz, 1H), 7.64 (d, J=7.9 Hz, 1H), 7.55-7.50 (m, 3H); $^{13}$C NMR (125 MHz, DMSO-d$_6$) δ 188.8, 172.6, 158.8, 137.9, 135.8, 135.4, 135.1, 134.0, 132.7, 124.1, 123.6, 120.6, 119.2, 117.3, 11.7, 106.5; CIMS m/z (rel intensity) 274 (MH$^+$, 100).

3-Cyano-5,11-dihydro-6-[3-(1H-imidazolyl)propyl]-5,11-dioxo-6,11-dihydro-5H-indeno[1,2-c]isoquinoline (72)

3-Cyano-5,11-dihydro-5,11-dioxoindeno-[1,2-c]isochromene (68, 200 mg, 0.73 mmol) was dissolved in tetrahydrofuran (10 mL). 3-(1H-Imidazol-1-yl)propyl-1-amine (69, 335 mg, 2.67 mmol) was dissolved in chloroform (5 mL) and the solution added to the reaction mixture. The reaction mixture was stirred for 3 h at room temperature and then heated at reflux for 1 h. The solution turned red and, upon reflux, an orange precipitate formed. The solvent was removed under vacuum and the solid purified by silica gel column chromatography, eluting with chloroform-methanol, 30:1. The desired compound was obtained as a yellow solid (103 mg, 37%): mp 256-258° C. IR (KBr) 3103, 2952, 2225, 1694, 1671, 1611, 1534, 1509, 1433, 1192, 850, 764, 665 cm$^{-1}$; $^1$H NMR (300 MHz, DMSO-d$_6$) δ 8.80 (d, J=8.6 Hz, 1H), 8.63 (d, J=1.4 Hz, 1H), 7.88 (dd, J=8.4 Hz, J=1.6 Hz, 1H), 7.67-7.64 (m, 2H), 7.43 (t, J=7.6 Hz, 1H), 7.35 (dt, J=7.5 Hz, J=1.2 Hz, 1H), 7.21 (s, 1H), 7.07 (s, 1H), 6.66 (d, J=7.5 Hz, 1H), 4.54 (t, J=7.8 Hz, 2H), 4.26 (t, J=6.2 Hz, 2H), 2.37 (p, J=8.2 Hz, J=6.6 Hz, 2H); ESIMS m/z (rel intensity) 381 (MH$^+$, 100); HRESIMS calcd for C$_{23}$H$_{16}$N$_4$O$_2$ 381.1352 (MH$^+$). found 381.1345 (MH$^+$); HPLC purity: 95.0% (MeOH—H$_2$O, 85:15), 95.4% (MeOH—H$_2$O, 95:5).

3-Cyano-6,11-dihydro-5,11-dioxo-6-(3-morpholinylpropyl)-5H-indeno-[1,2-c]isoquinoline (73)

3-Cyano-5,11-dihydro-5,11-dioxoindeno[1,2-c]isochromene (68, 130 mg, 0.47 mmol) was dissolved in chloroform (50 mL). 3-Morpholinopropyl-1-amine (70, 152 mg, 1.04 mmol) and molecular sieves were added and the reaction was mixture stirred at room temperature for 8 h. The reaction mixture was then heated at reflux for 1 h. The molecular sieves were filtered off, the solvent removed under vacuum and the residue purified by silica gel column chromatography, eluting with chloroform-methanol, 100:1. The desired compound was obtained as an orange solid (113 mg, 60.0%): mp 259-261° C. IR (Film) 3083, 2950, 2849, 2223, 1698, 1673, 1611, 1509, 1435, 1275, 1185, 1116, 998, 959, 896, 851, 766, 665 cm$^{-1}$; $^1$H NMR (CDCl$_3$, 500 MHz) δ 8.80 (d, J=8.6 Hz, 1H), 8.62 (d, J=1.7 Hz, 1H), 7.88-7.84 (m, 2H), 7.69 (m, 1H), 7.51-7.48 (m, 2H), 4.64 (t, J=7.8 Hz, 2H), 3.70 (t, J=4.4 Hz, 4H), 2.58 (t, J=6.2 Hz, 1H), 2.49 (br s, 4H), 2.05 (m, 2H); $^{13}$C NMR (125 MHz, CDCl$_3$) δ 189.5, 162.0, 157.8, 136.3, 135.3, 135.0, 133.4, 131.9, 124.4, 123.6, 123.4, 123.0, 110.0, 107.2, 66.9, 56.0, 53.9, 43.9, 25.7; ESIMS m/z (rel intensity) 400 (MH$^+$, 100); HRESIMS calcd for C$_{24}$H$_{21}$N$_3$O$_3$ 400.1661 (MH$^+$). found, 400.1665 (MH$^+$). Anal. calcd for C$_{24}$H$_{21}$N$_3$O$_3$.0.5H$_2$O: C, 70.57; H, 5.43; N, 10.29. Found: C, 70.71; H, 5.22; N, 10.01.

3-Cyano-6,11-dihydro-5,11-dioxo-6-[3-(dimethylaminopropyl]-5H-indeno[1,2-c]isoquinoline (74)

3-Cyano-5,11-dihydro-5,11-dioxoindeno[1,2-c]isochromene (68, 135 mg, 0.49 mmol) was dissolved in a mixture of tetrahydrofuran (10 mL). N',N'-Dimethylpropane-1,3-diamine (71, 158 mg, 1.51 mmol) was dissolved in chloroform (5 mL). This solution was added to the first solution, and the reaction mixture was stirred for 3 h at room temperature. The mixture was heated at reflux for 1 h. The solvent was removed under vacuum and the solid purified by silica gel column chromatography, eluting with chloroform-methanol, 50:1. The compound was obtained as a yellow solid (96 mg, 55%): mp 210-212° C. IR (Film) 2817, 2762, 2223, 1698, 1673, 1611, 1611, 1435, 1261, 1191, 1040, 897, 764 cm$^{-1}$; $^1$H NMR (500 MHz, DMSO-d$_6$) δ 8.78 (d, J=8.5 Hz, 1H), 8.62 (s, 1H), 7.87-7.84 (m, 2H), 7.67 (d, J=6.7 Hz, 1H), 7.50-7.46 (m, 2H), 4.59 (t, J=5.9 Hz, 2H), 2.53 (t, J=6.5 Hz, 2H), 2.32 (s, 6H), 2.04 (br p, J=8.5 Hz, 2H); $^{13}$C NMR (125 MHz, DMSO-d$_6$) δ 189.6, 162.0, 157.9, 136.3, 135.3, 135.1, 135.0, 133.6, 133.5, 131.8, 124.4, 123.7, 123.5, 123.0, 118.2, 109.9, 107.3, 56.6, 45.6, 43.8, 29.9; ESIMS m/z (rel intensity) 402 (MH$^+$, 100); HRESIMS calcd for C$_{23}$H$_{19}$N$_3$O$_4$ 402.1454 (MH$^+$). found 402.1452 (MH$^+$); HPLC purity: 97.4% (MeOH—H$_2$O, 95:5), 97.4% (MeOH).

3-Cyano-5,11-dihydro-8,9-methylenedioxy-5,11-dioxo[1,2-c]isochromene (76)

7-cyano-3-hydroxyphthalide (66, 1.55 g, 8.85 mmol) and 5,6-methylenedioxyphthalide (75, 1.58 g, 8.06 mmol) were dissolved in ethyl acetate (20 mL). Sodium (0.85 g, 34.8 mmol) was dissolved in methanol (35 mL) at 0° C. and the resulting solution added to the reaction mixture. The reaction mixture was stirred for 30 min at room temperature and then heated at reflux for 15 h. Concentrated hydrochloric acid (20 mL) was added and the solvent removed under vacuum. Benzene (100 mL) and para-toluenesulfonic acid (50 mg) were added, and the reaction mixture was connected to a Dean-Stark trap and heated at reflux for 16 h. Chloroform (100 mL) was added, the reaction mixture heated at reflux and immediately filtered. The solvent was removed under vacuum and the solid recrystallized from chloroform-methanol, 25:1, to remove unreacted phthalide. The compound was purified by silica gel column chromatography, eluting with chloroform-methanol, 50:1. The product was obtained as a yellow solid (133 mg, 10%): mp>350° C. Also, 0.81 g of the starting material 75 was recovered. IR (Film) 2233, 1692, 1417, 1313, 1152, 1029, 925, 861, 785, 665 cm$^{-1}$; $^1$H NMR (CDCl$_3$-MeOH-d$_4$, 300 MHz) δ 8.44 (s, 1H), 8.29 (d, J=8.1 Hz, 1H), 7.88 (dd, J=8.1 Hz, J=1.5 Hz, 1H), 7.05 (s, 1H), 6.94 (s, 1H), 6.09 (s, 2H); EIMS m/z (rel intensity) 317 (M$^+$, 100); HREIMS calcd for C$_{18}$H$_7$NO$_5$ 317.0324 (M$^+$). found 317.0327 (M$^+$).

3-Cyano-5,11-dihydro-6-[3-(dimethylamino)propyl]-5,11-dioxoindeno-[1,2-c]isoquinoline (77)

3-Cyano-5,11-dihydro-8,9-methylenedioxy-5,11-dioxo [1,2-c]isochromene (76, 91 mg, 0.28 mmol) was dissolved in tetrahydrofuran (25 mL). N$^1$,N$^1$-Dimethylpropane-1,3-diamine (71, 156 mg, 1.56 mmol) and molecular sieves were added and the reaction mixture stirred at room temperature for 8 h. The reaction mixture was then heated at reflux for 1 h. The molecular sieves were filtered off, the solvent removed in vacuo and the residue purified by recrystallization from chloroform-hexane. The desired compound was obtained as a purple solid (89 mg, 79%): mp 280-282° C. IR (Film) 2968, 2909, 2825, 2271, 1694, 1672, 1607, 1577, 1529, 1432, 1309, 1282, 1185, 1033, 852, 793 cm$^{-1}$; $^1$H NMR (500 MHz, CDCl$_3$-MeOH-d$_4$) δ 8.62 (d, J=8.5 Hz, 1H), 8.51 (s, 1H), 7.86 (d, J=8.5 Hz, 1H), 7.44 (s 1H), 7.08 (s, 1H), 6.08 (s, 1H), 4.45 (t, J=6.9 Hz, 2H), 2.46 (br s, 2H), 2.25 (s, 6H), 1.94 (m, 2H); $^{13}$C NMR (125 MHz, CDCl$_3$) δ 188.7, 162.2, 157.6, 152.0, 150.0, 135.2, 133.6, 131.3, 130.7, 123.8, 122.1, 118.1, 109.1, 106.6, 106.3, 105.4, 102.9, 56.4, 45.4, 43.5, 33.0, 26.8; ESIMS m/z (rel intensity) 401 (M$^+$, 100); HPLC purity: 100% (MeOH—H$_2$O, 90:10), 96.7% (MeOH—H$_2$O, 85:15).

6-(3-Bromopropyl)-9-methoxy-3-nitro-5H-indeno[1,2-c]isoquinoline-5,11(6H)-dione (80)

5-Nitrohomophthalic anhydride (47, 5.02 g, 24.2 mmol) was added to solution of 3-bromo-N-(4-methoxybenzylidene)propyl-1-amine (78, 6.21 g, 24.2 mmol) in chloroform (115 mL), and the reaction mixture was allowed to stir at room temperature for 1.5 h and then placed inside the freezer overnight. The precipitate was filtered and washed with chloroform (50 mL) and dried to provide intermediate 79 (5.13 g), which was used without further purification. Thionyl chloride (26 mL) was added to a suspension of 79 in benzene (200 mL) and the reaction mixture was heated at reflux until complete dissolution. The solvent was removed under vacuum and the residue diluted with nitrobenzene (225 mL) and chilled in an ice bath. Aluminum chloride (4.50 g, 33.8 mmol) was added and the reaction mixture was heated at 100° C. for 2 h. Cool water (200 mL) was added, the organic phase separated and the aqueous phase was extracted with CHCl$_3$ (3×70 mL). The combined organic layer was washed with a solution of NaHCO$_3$ (4.0 g) in water (75 mL). The solution was concentrated and hexanes were added until the precipitation of a red solid was observed. The solid was filtered, washed with hexanes (100 mL), and purified by flash silica gel column chromatography, eluting with chloroform-methanol, 12:1. The product was obtained as an orange solid (0.79 g, 11.2%): mp 282-284° C. IR (Film) 3097, 1809, 1745, 1685, 1604, 1510, 1337, 1231, 1127, 1082, 851 cm$^{-1}$; $^1$H NMR (300 MHz, CDCl$_3$) δ 9.17 (d, J=2.3 Hz, 1H), 8.81 (d, J=8.9 Hz, 1H), 8.47 (dd, J=9.0 Hz, J=2.3 Hz, 1H), 7.81 (d, J=8.5 Hz, 1H), 7.28 (d, J=2.5 Hz, 1H), 6.94 (dd, J=8.5 Hz, J=2.5 Hz, 1H), 4.51 (t, J=6.0 Hz, 2H), 3.84 (s, 3H), 3.75 (dd, J=7.5 Hz, J=6.6 Hz, 2H), 2.30 (br p, J=8.5 Hz, 2H); EIMS m/z (rel intensity) 442 (M$^+$, 100); HREIMS calcd for C$_{20}$H$_{15}$N$_2$O$_5$Br 442.0164 (M$^+$). found, 442.0158 (M$^+$).

3-Amino-6-(3-bromopropyl)-9-methoxy-5H-indeno[1,2-c]isoquinoline-5,11(6H)-dione (81)

6-(3-Bromopropyl)-9-methoxy-3-nitro-5H-indeno[1,2-c]isoquinoline-5,11(6H)-dione (80, 1.00 g, 2.26 mmol) was dissolved in tetrahydrofuran (60 mL), methanol (20 mL), and ethyl acetate (30 mL) and transferred to a Parr shaker flask. The reaction vessel was purged with argon for 10 min and then palladium-charcoal (10%, 20 mg) was added. The reaction mixture was shaken for 24 h under an atmosphere of hydrogen (60 psi). The solid was filtered off, the solvent removed under vacuum, and the compound purified by silica gel column chromatography, eluting with ethyl acetate. The product was obtained as a brown solid (0.55 g, 59%): mp 330° C. (dec). IR (Film) 3367, 1696, 1655, 1506, 1480, 1431, 1293, 1229, 1016, 834, 787, 665 cm$^{-1}$; $^1$H NMR (300 MHz, DMSO-d$_6$) δ 8.35 (d, J=8.6 Hz, 1H), 7.67-7.62 (m, 2H), 7.06 (d, J=2.5 Hz, 1H), 7.0.1-6.94 (m, 2H), 4.51 (t, J=6.0 Hz, 2H), 3.84 (s, 3H), 3.75 (dd, J=7.5 Hz, J=6.6 Hz, 2H), 2.30 (br p, J=8.5 Hz, 2H); EIMS m/z (rel intensity) 413 (M$^+$, 46), 333 ([M-HBr]$^+$, 100); HRESIMS m/z calcd for C$_{20}$H$_{17}$N$_2$O$_3$Br 413.0501 (MH$^+$). found, 413.0505 (MH$^+$).

6-(3-Bromopropyl)-3-iodo-9-methoxy-5H-indeno[1,2-c]isoquinoline-5,11(6H)-dione (82)

3-Amino-6-(3-bromopropyl)-9-methoxy-5H-indeno[1,2-c]isoquinoline-5,11(6H)-dione (81, 420 mg, 1.01 mmol) was dissolved in dioxane (10 mL). Concentrated hydrochloric acid (0.65 mL, 3.3 mmol) was added and the reaction mixture was stirred for 10 min and then cooled down to 0° C. A solution of sodium nitrite (114 mg, 1.65 mmol) in water (5 mL) was slowly added with stirring while the temperature was −20° C. The reaction mixture was stirred for 30 min and then slowly added to a solution of copper (I) iodide (200 mg) and potassium iodide (300 mg) in water (15 mL). The reaction mixture was stirred at room temperature for 8 h and then heated at reflux for 1 h. The reaction mixture was diluted with water (200 mL) and extracted with chloroform (3×100 mL). The combined organic extracts were washed with an aqueous solution of sodium thiosulfate (2×200 mL), aqueous sodium bicarbonate (2×200 mL), water (100 mL) and brine (100 mL). The organic solution was dried over sodium sulfate and the solvent removed under vacuum. The residue was purified by silica gel column chromatography, eluting with chloroform-methanol, 30:1. Compound 82 was obtained as a dark red solid (402 mg, 76%): mp 207-209° C. IR (Film) 2922, 1765, 1655, 1599, 1532, 1478, 1455, 1430, 1379, 1295, 1225, 1047, 969, 812, 788, 691, 666, 592 cm$^{-1}$; $^1$H NMR (CDCl$_3$, 500 MHz) δ 8.60 (d, J=1.5 Hz, 1H), 8.32 (d, J=8.6 Hz, 1H), 7.93 (dd, J=8.5 Hz, J=1.5 Hz, 1H), 7.64 (d, J=8.4 Hz, 1H), 7.15 (d, J=2.3 Hz, 1H), 6.82 (dd, J=8.3 Hz, J=2.4 Hz, 1H), 4.58 (t, J=7.2 Hz, 2H), 3.89 (s, 3H), 3.64 (t, J=6.2 Hz, 2H), 2.44 (t, J=7.2 Hz, 2H); $^{13}$C NMR (125 MHz, CDCl$_3$) δ 189.3, 162.5, 162.0, 156.6, 142.4, 137.6, 137.0, 131.4, 127.6, 124.7, 124.1, 123.9, 115.8, 111.1, 107.6, 91.2, 55.8, 44.2, 31.1, 30.2; ESIMS m/z (rel intensity) 523 (MH$^+$, 60), 403 [(MH$^+$—C$_3$H$_6$Br)$^+$, 100]; HRESIMS m/z calcd for C$_{20}$H$_{15}$NO$_3$IBr 523.9358 (MH$^+$). found, 523.9362 (MH$^+$).

6-(3-Azidopropyl)-3-iodo-9-methoxy-5H-indeno[1,2-c]isoquinoline-5,11(6H)-dione (83)

Sodium azide (0.59 g, 9.07 mmol) and 6-(3-bromopropyl)-3-iodo-9-methoxy-5H-indeno[1,2-c]isoquinoline-5,11(6H)-dione (82, 261 mg, 0.59 mmol) were diluted with DMSO (30 mL) and the mixture was heated at 90° C. for 12 h. The reaction mixture was diluted with CHCl$_3$ (100 mL), washed with water (100 mL) and sat aq NaCl (30 mL), and dried over sodium sulfate. The solution was concentrated to provide a crude solid that was purified by silica gel column chromatography, eluting with chloroform-methanol, 50:1, to afford an orange solid (0.16 g, 83%): mp 267-269° C. (dec). IR (KBr) 2090, 1688, 1662, 1598, 1532, 1478, 1424, 1298, 1164, 1014, 819, 791, 694 cm$^{-1}$; $^1$H NMR (300 MHz, CDCl$_3$) δ 8.61 (d, J=1.8 Hz, 1H), 8.34 (d, J=8.6 Hz, 1H), 7.92 (dd, J=8.6 Hz, J=1.8 Hz, 1H), 7.59 (d, J=8.4 Hz, 1H), 7.17 (d, J=2.5 Hz, 1H), 6.85 (dd, J=8.3 Hz, J=2.8 Hz, 1H), 4.53 (t, J=7.2 Hz, 2H), 3.89 (s, 3H), 3.63 (t, J=6.1 Hz, 2H), 2.11 (t, J=7.2 Hz, 2H); $^{13}$C NMR (125 MHz, CDCl$_3$) δ 188.9, 162.5, 161.8, 156.5, 142.2, 137.7, 136.9, 131.3, 127.6, 124.6, 123.9, 123.8, 115.8, 110.9, 107.4, 91.0, 55.7, 49.2, 42.7, 28.3; ESIMS m/z (rel intensity) 509 (MNa$^+$, 100); HRESIMS m/z calcd for $C_{20}H_{15}N_4O_3I$ 487.0267 (MH$^+$). found, 487.0271 (MH$^+$).

6-(3-Aminopropyl)-5,6-dihydro-9-methoxy-3-iodo-5,11-dioxo-11H-indeno[1,2-c]isoquinoline (84)

Triethylphosphite (0.2 mL) was added to a solution of 6-(3-azidopropyl)-3-iodo-9-methoxy-5H-indeno[1,2-c]isoquinoline-5,11(6H)-dione (83, 0.186 g, 0.459 mmol) in benzene (30 mL), and the reaction mixture was heated at reflux for 16 h. The reaction mixture was allowed to cool to room temperature, HCl in methanol (prepared from 0.5 mL of acetyl chloride in 9.5 mL of methanol) was added, and the reaction mixture was heated at reflux for 4 h. The reaction mixture was allowed to cool to room temperature and filtered to provide a red solid (0.159 g, 83%): mp 267-269° C. (dec). IR (KBr) 3399, 2937, 1692, 1658, 1600, 1532, 1478, 1429, 1298, 1228, 909, 823, 733 cm$^{-1}$; $^1$H NMR (300 MHz, CDCl$_3$) δ 8.65 (d, J=1.5 Hz, 1H), 8.37 (d, J=8.5 Hz, 1H), 7.94 (dd, J=8.6 Hz, J=1.6 Hz, 1H), 7.64 (d, J=8.4 Hz, 1H), 7.21 (d, J=2.4 Hz, 1H), 6.84 (dd, J=8.3 Hz, J=2.4 Hz, 1H), 4.58 (t, J=7.2 Hz, 2H), 3.89 (s, 3H), 2.89 (t, J=6.3 Hz, 2H), 2.00 (t, J=7.3 Hz, 2H); ESIMS m/z (rel intensity) 461 (MH$^+$, 100); HRESIMS m/z calcd for $C_{20}H_{17}N_2O_3I$ 461.0362 (MH$^+$). found, 461.0371 (MH$^+$); HPLC purity: 98.9% (MeOH—H$_2$O, 90:10), 96.7% (MeOH—H$_2$O, 80:20).

3-Iodo-9-methoxy-6-(3-(Dimethylamino)propyl)-5H-indeno[1,2-c]isoquinoline-5,11(6H)-dione (85)

3-Amino-6-(3-aminopropyl)-9-methoxy-5H-indeno[1,2-c]isoquinoline-5,11(6H)-dione (84, 111 mg, 1.93 mmol) was dissolved in methanol (10 mL) and acetic acid (5 mL). Aqueous formaldehyde (37%, 0.15 mL) was added and the reaction mixture was stirred at room temperature for 2 h. The reaction mixture was cooled to 0° C. and sodium cyanoborohydride (300 mg) was slowly added. The reaction mixture was stirred for 1 h at room temperature. Water (30 mL) was added and the reaction mixture extracted with chloroform (2×25 mL). The organic extracts were combined and washed with brine (30 mL). The solvent was removed in vacuo and the compound purified by silica gel column chromatography, eluting with chloroform. The product was obtained as a red solid (65 mg, 55%) mp>350° C. IR (Film) 3054, 2987, 1698, 1649, 1531, 1477, 1430, 1301, 1265, 740 cm$^{-1}$; $^1$H NMR (500 MHz, CDCl$_3$) δ 8.65 (d, J=1.8 Hz, 1H), 8.38 (d, J=8.6 Hz, 1H), 7.85 (dd, J=2.0, J=8.6 Hz, 1H), 7.67 (d, J=8.3 Hz, 1H), 7.21 (d, J=2.5 Hz, 1H), 6.83 (dd, J=2.5, J=8.4 Hz, 1H), 4.54 (t, J=8.1 Hz, 2H), 3.89 (s, 3H), 2.50 (d, J=6.3 Hz, 2H), 2.02 (m, 2H); $^{13}$C NMR (125 MHz, CDCl$_3$-MeOH-d$_4$) δ 189.5, 162.6, 162.2, 142.4, 137.7, 136.9, 131.6, 127.6, 124.6, 124.3, 123.8, 115.9, 111.2, 107.7, 91.0, 56.2, 55.7, 44.7, 43.0, 26.4; ESIMS m/z (rel intensity) 489 (MH$^+$, 100); HRESIMS m/z calcd for $C_{22}H_{21}N_2O_3I$ 489.0675 (MH$^+$). found, 489.0670 (MH$^+$); HPLC purity: 97.1% (MeOH—H$_2$O, 95:5); 97.5% (MeOH—H$_2$O, 85:15).

3-Amino-6-(3-chloropropyl)-5,6-dihydro-9-methoxy-5,11-dioxo-11H-indeno[1,2-c]isoquinoline (87)

6-(3-Chloropropyl)-5,6-dihydro-9-methoxy-3-nitro-5,11-dioxo-11H-indeno[1,2-c]isoquinoline (86) (0.220 g, 0.552 mmol) and 5% Pd/C (0.200 g) were diluted with THF (125 mL). The solution was degassed and allowed to stir at room temperature under a hydrogen atmosphere for 1 h. The solution was filtered, the filterpad was washed with chloroform (125 mL), and the filtrate was concentrated to provide a crude purple solid. The solid was purified by silica gel flash column chromatography, eluting with chloroform to provide a purple solid (0.080 g, 39%): mp 232-235° C. (dec). IR (KBr) 3357, 1644, 1544, 1510, 1272, 1052 cm$^{-1}$; $^1$H NMR (DMSO-d$_6$) δ 8.33 (d, J=8.6 Hz, 1H), 7.42 (dd, J=8.5 Hz, J=6.8 Hz, 1H), 7.32 (m, 2H), 7.14 (dd, J=6.7 Hz, J=1.0 Hz, 1H), 7.09 (dd, J=8.7 Hz, J=2.4 Hz, 1H), 5.74 (s, 2H), 4.68 (t, J=7.1 Hz, 2H), 3.97 (s, 3H), 3.73 (t, J=6.6 Hz, 2H), 2.21 (pent, J=7.1 Hz, 2H); ESIMS m/z (rel intensity) 369/371 (MH$^+$, 100/32). Anal. calcd for $C_{20}H_{17}ClN_2O_3$: C, 65.13; H, 4.65; N, 7.60. Found: C, 64.85; H, 4.74; N, 7.42.

3-Amino-6-(3-azidopropyl)-5,6-dihydro-9-methoxy-5,11-dioxo-11H-indeno[1,2-c]isoquinoline (88)

Sodium azide (0.063 g, 0.968 mmol) and 3-amino-6-(3-chloropropyl)-5,6-dihydro-9-methoxy-5,11-dioxo-11H-indeno[1,2-c]isoquinoline (87, 0.119 g, 0.323 mmol) were diluted with DMSO (25 mL) and the mixture was heated at 100° C. for 16 h. The reaction mixture was diluted with chloroform (50 mL), washed with water (3×25 mL), brine (25 mL), and dried over sodium sulfate. The solution was concentrated to provide a crude solid that was purified by silica gel column chromatography, eluting with a gradient of chloroform to 1% MeOH-chloroform, to provide a solid that was washed with diethyl ether to afford a purple solid (0.102 g, 84%): mp 220-223° C. IR (KBr) 3434, 3349, 2096, 1651, 1509, 1271 cm$^{-1}$; $^1$H NMR (DMSO-d$_6$) δ 8.34 (d, J=8.7 Hz, 1H), 7.42 (dd, J=8.5 Hz, J=6.7 Hz, 1H), 7.33 (m, 2H), 7.15 (dd, J=6.7 Hz, J=1.1 Hz, 1H), 7.09 (dd, J=8.7 Hz, J=2.5 Hz, 1H), 5.74 (s, 2H), 4.65 (m, 2H), 3.97 (s, 3H), 3.46 (t, J=6.7 Hz, 2H), 1.99 (m, 2H); ESIMS m/z (rel intensity) 376 (MH$^+$, 55). Anal. calcd for $C_{20}H_{17}N_5O_3$: C, 63.99; H, 4.56; N, 18.66. Found: C, 63.78; H, 4.38; N, 18.30.

3-Amino-6-(3-aminopropyl)-5,6-dihydro-9-methoxy-5,11-dioxo-11H-indeno[1,2-c]isoquinoline Dihydrochloride (89)

Triethyl phosphite (0.07 mL) was added to a solution of 3-amino-6-(3-azidopropyl)-5,6-dihydro-9-methoxy-5,11-dioxo-11H-indeno[1,2-c]isoquinoline (88, 0.061 g, 0.163 mmol) in benzene (20 mL) and the reaction mixture was heated at reflux for 16 h. The reaction mixture was allowed to cool to room temperature, 3 M HCl in methanol (10 mL) was added, and the reaction mixture was heated at reflux for 3 h. The reaction mixture was allowed to cool to room temperature, concentrated, and the precipitate was washed with chloroform (50 mL) and filtered to provide an orange solid (0.054 g, 78%): mp 246-248° C. (dec). IR (KBr) 3445, 2929, 1651, 1544, 1505, 1479, 1266 cm$^{-1}$; $^1$H NMR (DMSO-d$_6$) δ 8.51 (d, J=8.7 Hz, 1H), 8.03 (bs, 2H), 7.77 (d, J=2.2 Hz, 1H), 7.49 (m, 2H), 7.36 (d, J=7.6 Hz, 1H), 7.19 (dd, J=6.8 Hz, J=0.8 Hz, 1H), 4.61 (t, J=7.0 Hz, 2H), 4.01 (s, 3H), 2.86 (m, 2H), 2.09 (m, 2H); ESIMS m/z (rel intensity) 350 (MH$^+$, 90). Anal. calcd for $C_{20}H_{21}Cl_2N_3O_3 \cdot 1.0H_2O$: C, 54.55; H, 5.26; N, 9.54. Found: C, 54.87; H, 5.10; N, 9.21.

Molecular Modeling.

The Tdp1 crystal structure (PDB: 1RFF) was prepared by removing one of the monomers along with all crystallized waters, the polydeoxyribonucleotide 5'-D(*AP*GP*TP*T)-3', the Top1-derived peptide residues 720-727 (mutation L724Y), and all metal ions. The Lys265, Lys495 and His493 residues were protonated. Missing hydrogens were added as needed. GOLD docking was performed using the centroid x=8.0128, y=46.5888, z=-1.5534. The hydrogen bond length was set to 4 Å while the van der Waals parameter was set to 10 Å. The top ligand binding-pose (highest GOLD score) was selected and merged with the prepared protein. The ligand was surrounded by a sphere of 6 Å of radius and minimized by the conjugate gradient method using the MMFF94s force field and MMFF94 charges with Sybyl software. The calculation was terminated when the gradient reached a value of 0.05 kcal/(mol·Å).

Topoisomerase I-Mediated DNA Cleavage Reactions.

Top1 reactions were performed as recently described. Briefly, a 3'-[$^{32}$P]-end-labeled 117-bp DNA oligonucleotide (Integrated DNA Technologies) was incubated at 2 nM with recombinant Top1 in 20 μL of reaction buffer [10 mM Tris-HCl (pH 7.5), 50 mM KCl, 5 mM MgCl2, 0.1 mM EDTA, and 15 μg/mL BSA] at 25° C. for 20 min in the presence of various concentrations of compounds. The reactions were terminated by adding SDS (0.5% final concentration) followed by the addition of two volumes of loading dye (80% formamide, 10 mM sodium hydroxide, 1 mM sodium EDTA, 0.1% xylene cyanol, and 0.1% bromphenol blue). Reactions were subjected to 20% denaturing PAGE. Gels were dried and visualized by using a Typhoon 8600 and ImageQuant software (Molecular Dynamics).

Gel-based Assay Measuring the Inhibition of Recombinant Tdp1.

Tdp1 reactions were performed as recently described. Briefly, a 5'-[$^{32}$P]-labeled single-stranded DNA oligonucleotide containing a 3'-phosphotyrosine (N14Y) incubated with 5 pM recombinant Tdp1 in the absence or presence of inhibitor for 15 min at room temperature in a buffer containing 50 mM Tris HCl, pH 7.5, 80 mM KCl, 2 mM EDTA, 1 mM DTT, 40 μg/ml BSA and 0.01% Tween-20. Reactions were terminated by the addition of 1 volume of gel loading buffer [99.5% (v/v) formamide, 5 mM EDTA, 0.01% (w/v) xylene cyanol, and 0.01% (w/v) bromophenol blue]. Samples were subjected to a 16% denaturing PAGE and dried gels were exposed to a PhosphorImager screen (GE Healthcare). Gel images were scanned using a Typhoon 8600 (GE Healthcare) and densitometric analyses were performed using the ImageQuant software (GE Healthcare).

Surface Plasmon Resonance Analysis.

Binding experiments were performed as recently described. Briefly, Tdp1 was amine coupled to a CM5 sensor chip (GE Healthcare, Piscataway N.J.). In order to protect the amine groups with the active site from modification, 1 mM Tdp1 was incubated with 2 mM of a 14 base oligonucleotide containing at phosphate group at the 3' end (GATCTAAAA-GACTT) (SEQ ID NO: 1) in 10 mM sodium acetate pH 4.5 for 20 min. The CM5 chip surface was activated for 7 min with 0.1 M NHS and 0.4 M EDC at a flow rate of 20 mL/min and Tdp1-oligonucleotide mixture was injected until approximately 4000 RU's was attached. Activated amine groups were quenched with an injection of 1 M solution of ethanolamine pH 8.0 for 7 min. Any bound oligonucleotide was removed by washing the surface with 1 M NaCl. A reference surface was prepared in the same manner without coupling of Tdp1. Compound 70 was diluted into running buffer [10 mM Hepes, 150 mM NaCl, 0.01% tween 20 (v/v), 5% DMSO (v/v) pH 7.5] and injected over all flow cells at 30 mL/min at 25° C. Following compound injections, the surface was regenerated with a 30 second injection 1 M NaCl, a 30 s injection of 50% DMSO (v/v) and a 30 s running buffer injection. Each cycle of compound injection was followed by buffer cycle for referencing purposes. A DMSO calibration curve was included to correct for refractive index mismatches between the running buffer and compound dilution series.

What is claimed is:

1. A compound of the formula

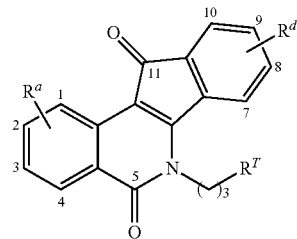

or a pharmaceutically acceptable salt thereof,
wherein:
$R^T$ is amino, $R^a$ is 3-carboxymethylamino and $R^d$ is hydrogen; or
$R^T$ is amino, $R^a$ is 3-amino and $R^d$ is 9-methoxy; or
$R^T$ is amino, $R^a$ is 3-iodo and $R^d$ is hydrogen; or
$R^T$ is dimethylamino, $R^a$ is 3-iodo and $R^d$ is 9-methoxy; or
$R^T$ is dimethylamino, $R^a$ is 3-cyano and $R^d$ is hydrogen.

2. A pharmaceutical composition comprising a compound of claim 1 and one or more carriers, diluents, or excipients, or a combination thereof.

3. A compound of the formula

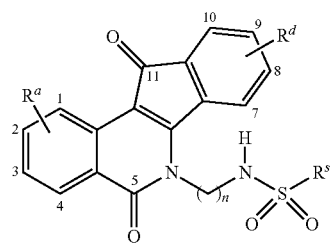

or a pharmaceutically acceptable salt thereof,
wherein:
n is 1, 2, 3, 4, 5, 6, 7, 8, 9, 11, or 12,
$R^a$ represents 1-4 substituents each of which is independently selected from the group consisting of hydrogen, halo, hydroxy, optionally substituted (1-4C)alkyl, optionally substituted (1-4C)alkoxy, cyano, nitro, optionally substituted alkylthio, optionally substituted alkylsulfonyl, carboxylic acid and derivatives thereof, and sulfonic acid and derivatives thereof;
or $R^a$ represents 2-4 substituents where 2 of said substituents are adjacent substituents and are taken together with the attached carbons to form an optionally substituted heterocycle, and where any remaining substituents are each independently selected from the group consisting of hydrogen, halo, hydroxy, optionally substituted (1-4C)alkyl, optionally substituted (1-4C)alkoxy, cyano, nitro, optionally substituted (1-4C)alkylthio, optionally substituted (1-4C)alkylsulfonyl, carboxylic acid and derivatives thereof, and sulfonic acid and derivatives thereof; and
$R_d$ represents 1-4 substituents each of which is independently selected from the group consisting of hydrogen, halo, hydroxy, optionally substituted (1-4C)alkyl, optionally substituted (1-4C)alkoxy, cyano, nitro, optionally substituted (1-4C)alkylthio, optionally substituted (1-4C)alkylsulfonyl, phenyl (which may bear one or more amino, hydroxyl, halo, thiol, (1-6C)alkyl or halo(1-6C)alkyl substituents), carboxylic acid and derivatives thereof, and sulfonic acid and derivatives thereof; or $R_d$ represents 2-4 substituents where 2 of said substituents are adjacent substituents and are taken together with the attached carbons to form an optionally substituted heterocycle, and where any remaining substituents are each independently selected from the group consisting of hydrogen, halo, hydroxy, optionally substituted (1-4C)alkyl, optionally substituted (1-4C)alkoxy, cyano, nitro, optionally substituted (1-4C)alkylthio, optionally substituted (1-4C)alkylsulfonyl, carboxylic acid and derivatives thereof, and sulfonic acid and derivatives thereof;
$R_S$ is (1-6C)alkyl, (3-7C)cycloalkyl or phenyl, which phenyl may bear one or more amino, hydroxyl, halo, thiol, (1-6C)alkyl or halo(1-6C)alkyl substituents.

4. A pharmaceutical composition comprising a compound of claim 3 and one or more carriers, diluents, or excipients, or a combination thereof.

5. A compound of the formula

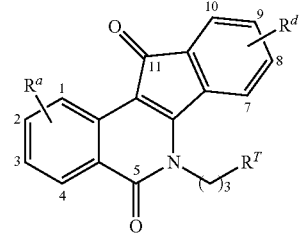

or a pharmaceutically acceptable salt thereof,
wherein:
$R^T$ is dimethylamino, $R_a$ is 3-cyano and $R_d$ is 8,9-methylenedioxy; or
$R^T$ is 4-morpholinyl, $R_a$ is 3-cyano and $R_d$ is hydrogen; or
$R^T$ is imidazolyl, $R_a$ is 3-cyano and $R_d$ is hydrogen.

6. A pharmaceutical composition comprising a compound of claim 5 and one or more carriers, diluents, or excipients, or a combination thereof.

* * * * *

SEQUENCE LISTING

```
<160> NUMBER OF SEQ ID NOS: 3

<210> SEQ ID NO 1
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 1
gatctaaaag actt                                                        14

<210> SEQ ID NO 2
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 2
gatctaaaag actt                                                        14

<210> SEQ ID NO 3
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 3
gatctaaaag actt                                                        14
```